(12) United States Patent
Giftakis et al.

(10) Patent No.: US 8,744,562 B2
(45) Date of Patent: Jun. 3, 2014

(54) METHOD FOR MONITORING OR TREATING NERVOUS SYSTEM DISORDERS

(75) Inventors: Jonathon E. Giftakis, Maple Grove, MN (US); Nina M. Graves, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 584 days.

(21) Appl. No.: 12/965,608

(22) Filed: Dec. 10, 2010

(65) Prior Publication Data

US 2011/0105913 A1 May 5, 2011

Related U.S. Application Data

(62) Division of application No. 11/311,393, filed on Dec. 19, 2005, now Pat. No. 8,041,419.

(60) Provisional application No. 60/636,929, filed on Dec. 17, 2004.

(51) Int. Cl.
*A61B 5/04* (2006.01)

(52) U.S. Cl.
USPC ........... 600/544; 600/545; 600/508; 600/509; 600/515

(58) Field of Classification Search
USPC ................. 600/483, 544, 545, 508, 529, 484
See application file for complete search history.

(56) References Cited

U.S. PATENT DOCUMENTS

| | | | |
|---|---|---|---|
| 4,374,382 A | 2/1983 | Markowitz | |
| 4,485,813 A | 12/1984 | Anderson | |
| 4,495,950 A | 1/1985 | Schneider | |
| 4,503,857 A | 3/1985 | Boute | |
| 4,556,063 A | 12/1985 | Thompson | |
| 4,567,892 A | 2/1986 | Plicchi | |
| 4,596,251 A | 6/1986 | Plicchi | |
| 4,702,254 A | 10/1987 | Zabara | |
| 4,862,144 A | 8/1989 | Tao | |
| 4,867,164 A | 9/1989 | Zabara | |
| 4,903,701 A | 2/1990 | Moore | |
| 4,987,897 A | 1/1991 | Funke | |
| 5,003,976 A | 4/1991 | Alt | |
| 5,025,807 A | 6/1991 | Zabara | |

(Continued)

FOREIGN PATENT DOCUMENTS

| | | |
|---|---|---|
| EP | 0512577 | 11/1992 |
| WO | 9726823 | 7/1997 |

(Continued)

OTHER PUBLICATIONS

Opherk et al., Heart rate and EKG changes in 102 seizures: analysis of influencing factors, Epilepsy Research, vol. 52, 2002, pp. 117-127.*

(Continued)

*Primary Examiner* — Michael Kahelin
*Assistant Examiner* — Tho Tran
(74) *Attorney, Agent, or Firm* — Fredrikson & Byron, P.A.

(57) ABSTRACT

A medical device system that includes a brain monitoring element, cardiac monitoring element and a processor. The processor is configured to receive a brain signal from the brain monitoring element and a cardiac signal from the cardiac monitoring element. The processor is further configured to compare the brain signal to the cardiac signal. A method of comparing a brain signal to a cardiac signal is also provided.

11 Claims, 50 Drawing Sheets

(56) References Cited

U.S. PATENT DOCUMENTS

| | | | |
|---|---|---|---|
| 5,029,082 A * | 7/1991 | Shen et al. | 600/512 |
| 5,052,388 A | 10/1991 | Sivula | |
| 5,113,859 A | 5/1992 | Funke | |
| 5,127,404 A | 7/1992 | Wyborny | |
| 5,168,759 A | 12/1992 | Bowman | |
| 5,203,326 A | 4/1993 | Collins | |
| 5,271,395 A | 12/1993 | Wahlstrand | |
| 5,312,451 A | 5/1994 | Limousin | |
| 5,314,430 A | 5/1994 | Bardy | |
| 5,336,244 A | 8/1994 | Weijand | |
| 5,354,316 A | 10/1994 | Keimel | |
| 5,354,318 A | 10/1994 | Taepke | |
| 5,409,009 A | 4/1995 | Olson | |
| 5,509,927 A | 4/1996 | Epstein | |
| 5,545,186 A | 8/1996 | Olson | |
| 5,554,177 A | 9/1996 | Kieval | |
| 5,560,368 A | 10/1996 | Berger | |
| 5,562,711 A | 10/1996 | Yerich | |
| 5,626,622 A | 5/1997 | Cooper | |
| 5,645,068 A | 7/1997 | Mezack | |
| 5,683,432 A | 11/1997 | Goedeke et al. | |
| 5,684,460 A | 11/1997 | Scanlon | |
| 5,713,923 A | 2/1998 | Ward | |
| 5,749,900 A | 5/1998 | Schroeppel | |
| 5,752,976 A | 5/1998 | Duffin | |
| 5,782,891 A | 7/1998 | Hassler | |
| 5,836,988 A | 11/1998 | Cooper | |
| 5,871,517 A | 2/1999 | Abrams | |
| 5,928,272 A | 7/1999 | Adkins | |
| 5,987,352 A | 11/1999 | Klein | |
| 5,995,868 A | 11/1999 | Dorfmeister | |
| 6,029,087 A | 2/2000 | Wohlgemuth | |
| 6,035,233 A | 3/2000 | Schroeppel | |
| 6,067,473 A | 5/2000 | Greeninger | |
| 6,083,248 A | 7/2000 | Thompson | |
| 6,115,630 A | 9/2000 | Stadler | |
| 6,128,526 A | 10/2000 | Stadler | |
| 6,134,474 A | 10/2000 | Fischell | |
| 6,155,267 A | 12/2000 | Nelson | |
| 6,185,459 B1 | 2/2001 | Mehra | |
| 6,200,265 B1 | 3/2001 | Walsh | |
| 6,263,237 B1 | 7/2001 | Rise | |
| 6,280,461 B1 | 8/2001 | Glegyak | |
| 6,337,997 B1 | 1/2002 | Rise | |
| 6,341,236 B1 | 1/2002 | Osorio | |
| 6,353,754 B1 | 3/2002 | Fischell | |
| 6,360,122 B1 | 3/2002 | Fischell | |
| 6,363,274 B1 | 3/2002 | Scalisi | |
| 6,366,813 B1 | 4/2002 | DiLorenzo | |
| 6,415,174 B1 | 7/2002 | Bebehani | |
| 6,427,086 B1 | 7/2002 | Fischell | |
| 6,463,328 B1 | 10/2002 | John | |
| 6,466,822 B1 | 10/2002 | Pless | |
| 6,473,639 B1 | 10/2002 | Fischell | |
| 6,480,743 B1 | 11/2002 | Kirkpatrick | |
| 6,496,175 B1 | 12/2002 | Fukuo | |
| 6,496,715 B1 | 12/2002 | Lee | |
| 6,505,067 B1 | 1/2003 | Lee | |
| 6,512,940 B1 | 1/2003 | Brabec | |
| 6,512,949 B1 | 1/2003 | Combs | |
| 6,522,915 B1 | 2/2003 | Ceballos | |
| 6,549,804 B1 | 4/2003 | Osorio | |
| 6,556,859 B1 | 4/2003 | Wohlgemuth | |
| 6,572,542 B1 | 6/2003 | Houben | |
| 6,587,727 B2 | 7/2003 | Osorio | |
| 6,622,036 B1 | 9/2003 | Suffin | |
| 6,647,292 B1 | 11/2003 | Bardy | |
| 6,650,938 B2 | 11/2003 | Boute | |
| 6,656,125 B2 | 12/2003 | Misczynski | |
| 6,671,555 B2 | 12/2003 | Gielen | |
| 6,671,556 B2 | 12/2003 | Osorio | |
| 6,719,701 B2 | 4/2004 | Lade | |
| 6,721,599 B2 | 4/2004 | de Vries | |
| 6,745,076 B2 | 6/2004 | Wohlgemuth | |
| 6,920,357 B2 | 7/2005 | Osorio | |
| 6,934,580 B1 | 8/2005 | Osorio | |
| 6,961,618 B2 | 11/2005 | Osorio | |
| 7,103,412 B1 | 9/2006 | Kroll | |
| 7,146,218 B2 | 12/2006 | Esteller | |
| 7,162,304 B1 | 1/2007 | Bradley | |
| 7,174,206 B2 | 2/2007 | Frei | |
| 7,177,674 B2 | 2/2007 | Echauz | |
| 7,207,948 B2 | 4/2007 | Coyle | |
| 7,242,983 B2 | 7/2007 | Frei | |
| 7,324,845 B2 | 1/2008 | Mietus | |
| 2001/0051819 A1 | 12/2001 | Fischell | |
| 2002/0072778 A1 | 6/2002 | Guck | |
| 2002/0099412 A1 | 7/2002 | Fischell | |
| 2002/0107553 A1 | 8/2002 | Hill | |
| 2002/0169485 A1 | 11/2002 | Pless | |
| 2003/0004548 A1 | 1/2003 | Warkentin | |
| 2003/0073917 A1 * | 4/2003 | Echauz et al. | 600/510 |
| 2003/0083716 A1 | 5/2003 | Nicolelis | |
| 2003/0149457 A1 | 8/2003 | Tcheng | |
| 2003/0195574 A1 | 10/2003 | Osorio | |
| 2003/0195588 A1 | 10/2003 | Fischell | |
| 2003/0236474 A1 | 12/2003 | Singh | |
| 2004/0006264 A1 | 1/2004 | Mojarradi | |
| 2004/0102816 A1 | 5/2004 | Mazar | |
| 2004/0116974 A1 | 6/2004 | Obel | |
| 2004/0133119 A1 | 7/2004 | Osorio | |
| 2004/0133120 A1 | 7/2004 | Frei | |
| 2004/0133248 A1 | 7/2004 | Frei | |
| 2004/0133390 A1 | 7/2004 | Osorio | |
| 2004/0138516 A1 | 7/2004 | Osorio | |
| 2004/0138517 A1 | 7/2004 | Osorio | |
| 2004/0138518 A1 | 7/2004 | Rise | |
| 2004/0138536 A1 | 7/2004 | Frei | |
| 2004/0138580 A1 | 7/2004 | Frei | |
| 2004/0138581 A1 | 7/2004 | Frei | |
| 2004/0138647 A1 | 7/2004 | Osorio | |
| 2004/0138711 A1 | 7/2004 | Osorio | |
| 2004/0138721 A1 | 7/2004 | Osorio | |
| 2004/0152958 A1 | 8/2004 | Frei | |
| 2004/0158119 A1 | 8/2004 | Osorio | |
| 2004/0176817 A1 | 9/2004 | Wahlstrand | |
| 2004/0181263 A1 | 9/2004 | Balzer | |
| 2004/0199482 A1 | 10/2004 | Wilson | |
| 2004/0215240 A1 | 10/2004 | Lovett | |
| 2004/0230105 A1 | 11/2004 | Geva | |
| 2004/0267152 A1 | 12/2004 | Pineda | |
| 2005/0010265 A1 | 1/2005 | Baru Fassio | |
| 2005/0081847 A1 | 4/2005 | Lee | |
| 2005/0115561 A1 | 6/2005 | Stahmann | |
| 2005/0197590 A1 | 9/2005 | Osorio | |
| 2005/0216071 A1 | 9/2005 | Devlin | |
| 2006/0058856 A1 | 3/2006 | Morrell | |
| 2006/0094970 A1 | 5/2006 | Drew | |
| 2006/0094972 A1 | 5/2006 | Drew | |
| 2006/0135877 A1 | 6/2006 | Giftakis | |
| 2006/0135881 A1 | 6/2006 | Giftakis | |
| 2006/0136006 A1 | 6/2006 | Giftakis | |
| 2006/0195144 A1 | 8/2006 | Giftakis | |
| 2006/0206159 A1 | 9/2006 | Moffitt | |
| 2006/0224067 A1 | 10/2006 | Giftakis | |
| 2006/0241725 A1 | 10/2006 | Libbus | |
| 2006/0265022 A1 * | 11/2006 | John et al. | 607/45 |
| 2007/0100392 A1 | 5/2007 | Maschino | |
| 2007/0161919 A1 | 7/2007 | DiLorenzo | |
| 2007/0238939 A1 | 10/2007 | Giftakis | |
| 2007/0239054 A1 | 10/2007 | Giftakis | |
| 2007/0239060 A1 | 10/2007 | Giftakis | |
| 2007/0239230 A1 | 10/2007 | Giftakis | |
| 2007/0260147 A1 | 11/2007 | Giftakis | |
| 2007/0260286 A1 | 11/2007 | Giftakis | |
| 2007/0260289 A1 | 11/2007 | Giftakis | |
| 2007/0265536 A1 | 11/2007 | Giftakis | |
| 2007/0265677 A1 | 11/2007 | Giftakis | |
| 2008/0033490 A1 | 2/2008 | Giftakis | |
| 2008/0269842 A1 | 10/2008 | Giftakis | |

(56) References Cited

U.S. PATENT DOCUMENTS

FOREIGN PATENT DOCUMENTS

| WO | 0234332 | 5/2002 |
|---|---|---|
| WO | 0236003 | 5/2002 |
| WO | 0249500 | 6/2002 |
| WO | 2004091720 | 10/2004 |

OTHER PUBLICATIONS

Leutmezer et al., Electrocardiographic changes at the onset of epileptic seizures, International League Against Epilepsy, vol. 44(3), 2003, pp. 348-354.*

Zijlmans et al., Heart rate changes and ECG abnormalities during epileptic seizures: prevalence and definition of an objective . clinical sign, International League Against Epilepsy, vol. 43(8), pp. 847-854, 2002.*

U.S. Appl. No. 11/766,886 Notice of Allowance mailed Sep. 23, 2011, 3 pages.

U.S. Appl. No. 11/380,462 Notice of Allowance mailed Sep. 27, 2011, 3 pgs.

U.S. Appl. No. 11/741,103 Notice of Allowance mailed Sep. 28, 2011, 3 pages.

U.S. Appl. No. 11/767,054 Notice of Allowance mailed Nov. 15, 2011, 3 pgs.

U.S. Appl. No. 11/741,111 Office Action mailed Dec. 7, 2011, 28 pgs.

U.S. Appl. No. 11/741,126 Office Action mailed Dec. 6, 2011, 24 pgs.

U.S. Appl. No. 11/741,119 Final Office Action mailed Dec. 22, 2011, 32 pages.

U.S. Appl. No. 11/796,576 Final Office Action mailed Jan. 6, 2012, 10 pages.

U.S. Appl. No. 11/796,575 Final Office Action mailed Mar. 18, 2011, 11 pages.

U.S. Appl. No. 11/741,119 Office Action mailed Mar. 28, 2011, 28 pages.

U.S. Appl. No. 11/796,576 Final Office Action mailed Mar. 30, 2011, 10 pages.

U.S. Appl. No. 11/767,054 Office Action mailed Jan. 4, 2011, 8 pages.

U.S. Appl. No. 11/766,886 Office Action mailed Apr. 11, 2011, 10 pgs.

U.S. Appl. No. 11/741,109 Final Office Action mailed Apr. 12, 2011, 8 pgs.

U.S. Appl. No. 11/380,462 Office Action mailed Apr. 13, 2011, 7 pgs.

U.S. Appl. No. 11/741,103 Office Action mailed Apr. 13, 2011, 10 pgs.

U.S. Appl. No. 11/796,577 Notice of Allowance mailed May 5, 2011, 13 pgs.

U.S. Appl. No. 11/767,054 Office Action mailed Jun. 15, 2011, 10 pgs.

U.S. Appl. No. 11/311,393 Notice of Allowance mailed Jun. 13, 2011, 4 pgs.

U.S. Appl. No. 11/311,200 Notice of Allowance mailed Jun. 13, 2011, 3 pages.

U.S. Appl. No. 11/741,109 Notice of Allowance mailed Jul. 5, 2011, 3 pages.

U.S. Appl. No. 11/796,576 Office Action mailed Jul. 8, 2011, 7 pages.

U.S. Appl. No. 11/796,382 Notice of Allowance mailed Mar. 2, 2011, 7 pages.

Frei MG, Osorio I. Left vagus nerve stimulation with the neurocybernetic prosthesis has complex effects on heart rate and on its variability in humans. Epilepsia. Aug. 2001;42(8):1007-1016. Presented in part at the American Epilepsy Society Annual Meetings San Francisco, CA, 1996, and San Diego, CA, 1998).

Sunderam S, Osorio I, Frei Mg, Watkins III JF. Stochastic modeling and prediction of experimental seizures in sprague-dawley rats. J Clin Neurophysiol. May 2001;18(3):275-282.

Osorio I, Harrison Maf, Frei MF, Lai YC. Observations on the application of the correlation dimension and correlation integral to the prediction of seizures. J Clin Neurophysiol. May 2001;18(3);269-274.

Ingram J, Sunderam S, Frei MG, Osorio, I. Autonomic regulation during complex partial seizures: A thermographic study. Abstract; Epilepsia. 41(S7);59. Proceedings of the 54th Annual Meeting of the American Epilepsy Society, Los Angeles, CA, Dec. 1-6, 2000.

Sunderam S, Watkins III JF, Frei MF, and Osorio I. A stochastic analysis of ictal-interictal transitions during experimental seizures: Seizure duration depends on the duration of preceding ictal and interictal states. Abstract; Epilepsia. 41(S7);49. Proceedings of the 54th Annual Meeting of the American Epilepsy Society, Los Angeles, CA, Dec. 1-6, 2000.

DiTeresi CA, Thompson M, Frei MG, Sunderam S, and Osorio I. Loss of function during partial seizures: a quantitative study in humans. Abstract; Epilepsia. 41(S7);237. Proceedings of the 54th Annual Meeting of the American Epilepsy Society, Los Angeles, CA, Dec. 1-6, 2000.

Nagaraddi V, Wilkinson SB, Osorio I. The effect of one hertz stimulation on kindled seizures in rats. Abstract; Proceeding of the 54th Annual Meeting of the American Epilepsy Society, Los Angeles, CA, Dec. 1-6, 2000.

Frei Mg, Davidchack R, Osorio I. Least squares acceleration filtering for estimating signal derivatives and Sharpness at extrema. IEEE. Aug. 1999; 46(8):971-977.

Osorio I, Frei MG, Wilkinson SB. Real time automated detection and quantitative analysis of seizures and short term predictions of clinical onset. Epilepsia. 1998;39(S16):615-627.

Thomas CV, Angel CA, Watkins JM, Frei MG, Bunag RD, Osorio I. Effects of vagal and sciatic stimulation on 3-MPA induced seizures in rats. Epilepsia. 1998;39(S6):29.

Frei MG, Haas SM, Ingram JL, Osorio I. Filter design methods for improved seizure detection. Epilepsia. 1998;39 (S6):108.

Powell J, Frei MG, Davidchak R, Watkins JM, Wilkinson SB, Osorio I. Ictal tachycardia does not closely correlate with electrographic onset of ictal ECoG frequency changes. Epilepsia. 1998;39(S6):112.

Frei MG, Davidchack R, Osorio I. Effects of vagal stimulation on human ECG. Epilepsia. 1998:39(S6):200.

Frei MG, Osorio I, Davidchack R. A reappraisal of the value of EKG in the detection of epileptic seizures. Abstract; Epilepsia. 1996:37(S5). Poster presentation, 50th Annual Meeting of the American Epilepsy Society, San Francisco, CA., Dec. 8, 1996.

Han P, Frei MG, Osorio I. Probable mechanisms of action of vagus nerve stimulation in humans with epilepsy: Is the heart a window into the brain? Abstract; Epilepsia. 1996:37(S5):83. Platform presentation, 50th Annual Meeting of the American Epilepsy Society, San Francisco, CA, Dec. 8, 1996.

Frei MG, Osorio I, Wilkinson SB. Quantitative analysis of inter-ictal vs. ictal ECoG signals. Abstract; Epilepsia. 1995:36 (S4):5. Poster presentation, 49th Annual Meeting of the American Epilepsy Society, Baltimore, MD, Dec. 4, 1995.

Osorio I, Frei MG, Lerner D, Wilkinson S. A method for accurate automated real time seizure detection. Abstract; Epilepsia. 1995:36(S4):4. Poster presentation, 49th Annual Meeting of the American Epilepsy Society, Baltimore, MD, Dec. 4, 1995.

Ingram J, Osorio I, Frei MG, Wilkinson SB, Troster A. Temporospatial behavior of seizures of temporal lobe origin. Abstract; Epilepsia. 1995:36(S4):9. Poster presentation, 49th Annual Meeting of the American Epilepsy Society, Baltimore, MD, Dec. 4, 1995.

Hayden R, Lerner D, Osorio I, Lai Yc, Frei MG.dimension does not distinguish ictal from interictal activity or noise. Abstract; Epilepsia. 1995:36(S4):5. Poster presentation, 49th Annual Meeting of the American Epilepsy Society, Baltimore, MD, Dec. 4, 1995.

Osorio I, Frei MG, Lerner D, Wilkinson SB. Automated rapid seizure detection in the human ECoG. Abstract in Proceedings of the IEEE Computer-Based Medical Systems, Lubbock, TX, Jun. 9-12, 1995.

Blum M, Floyd R, Vaughan P, Rivest R, Tarjan R. Linear Time Bounds for Median Computations. Abstract in *, Aug. 1971.

Hastad J. Median finding. Advanced Algorithms. Lecture 11: May 3, 1995.

Leutmezer, "Electrocardiographic Changes at Seizure Onset," Epilepsia, 2003, pp. 348-354, 44(3).

Rocamora, "Cardiac Asystole in Epilepsy: Clinical and Neurophysiologic Features," Epilepsia, 2003, pp. 179-185, 44 (2).

(56) References Cited

OTHER PUBLICATIONS

Tavernor, "Electrocardiograph QT Lengthening Associated with Epileptiform EEG Discharges—a Role in Sudden Unexplained Death in Epilepsy," Seizure, Mar. 1996, pp. 79-83, 5(1).
Devinsky, "Effects of Seizures on Autonomic and Cardiovascular Function," Epilepsy Currents, Mar./Apr. 2004, pp. 43-46, 4(2).
Donner, "Sudden Unexplained Death in Children with Epilepsy," Neurology, 2001, pp. 430-434, 57.
Nei, "EEG and ECG in Sudden Unexplained Death in Epilepsy," Epilepsia, 2004, pp. 338-345, 45(4).
Vaughn, "Monitoring Heart Period Variability changes During Seizures. II. Diversity and Trends", J. Epilepsy, 1996, p. 27-34, vol. 9.
Pacemaker Stops Epilepsy Deaths, Dec. 2004, BBC News World Edition.
Jones, Heart Rate Responses to Selective Stimulation of Cardiac Vagal C Fibres in Anaesthetized Cats, Rats and Rabbits, 1995, pp. 203-214, J. Physiol. 489.1, London.
Asconape et al., Early Experience with Vagus Nerve Stimulation for the Treatment of Epilepsy: Cardiac Complications, No. 6.058—Abstract from American Epilepsy Society, Epilepsia, 1998, vol. 39, Supp. 6.
Kamath, Neurocardiac responses to Vagoaferent Electrostimulation in Humans, 1992, pp. 1581-1687, PACE, vol. 15.
International Search and the Written Opinion, dated May 3, 2006 for PCT Application No. PCT/US2005/045656 8 pages).
International Search and the Written Opinion, dated May 3, 2006 for PCT Application No. PCT/US2005/045648 8 pages).
International Search and the Written Opinion, dated May 8, 2006 for PCT Application No. PCT/US2005/047628 8 pages).
International Search and the Written Opinion, dated May 8, 2006 for PCT Application No. PCT/US2005/045902 8 pages).
International Search and the Written Opinion, dated May 8, 2006 for PCT Application No. PCT/US2007/067625 13 pages).
U.S. Appl. No. 11/311,043 Non Final Office Action mailed Dec. 23, 2008, 8 pgs.
U.S. Appl. No. 11/380,462 Non Final Office Action mailed Apr. 8, 2009, 13 pgs.
U.S. Appl. No. 11/796,576 Non Final Office Action mailed Jun. 17, 2009, 8 pgs.
U.S. Appl. No. 11/311,043 Notice of Allowance mailed Aug. 10, 2009, 4 pgs.
U.S. Appl. No. 11/311,200 Non Final Office Action mailed Aug. 25, 2009, 7 pgs.
U.S. Appl. No. 11/796,382 Non Final Office Action mailed Nov. 23, 2009, 30 pgs.
U.S. Appl. No. 11/380,462 Final Office Action mailed Nov. 9, 2009, 12 pgs.
U.S. Appl. No. 11/311,200 Notice of Allowance mailed Dec. 5, 2009, 3 pgs.
U.S. Appl. No. 11/311,043 Notice of Allowance mailed Dec. 21, 2009, 1 pgs.
U.S. Appl. No. 11/796,576 Office Action mailed Jan. 8, 2010, 7 pgs.
U.S. Appl. No. 11/796,575 Office Action mailed Mar. 12, 2010, 8 pgs.
U.S. Appl. No. 11/796,577 Office Action mailed Mar. 9, 2010, 8 pgs.
U.S. Appl. No. 11/380,462 Office Action mailed Mar. 15, 2010, 12 pgs.
U.S. Appl. No. 11/311,043 Notice of Allowance mailed May 5, 2010, 4 pgs.
U.S. Appl. No. 11/311,200 Notice of Allowance mailed Apr. 20, 2010, 1 pgs.
U.S. Appl. No. 11/796,382 Office Action mailed May 20, 2010, 10 pages.
U.S. Appl. No. 11/311,456 Office Action mailed May 28, 2010, 11 pages.
U.S. Appl. No. 11/311,393 Office Action mailed Jun. 4, 2010, 10 pages.
U.S. Appl. No. 11/311,200 Office Communication mailed Jul. 26, 2010, 6 pgs.
U.S. Appl. No. 11/796,576 Office Action mailed Aug. 20, 2010, 7 pgs.
U.S. Appl. No. 11/796,575 Office Action mailed Aug. 31, 2010, 10 pgs.
U.S. Appl. No. 11/741,103 Office Action mailed Aug. 31, 2010, 10 pgs.
U.S. Appl. No. 11/766,886 Office Action mailed Aug. 31, 2010, 10 pgs.
U.S. Appl. No. 11/741,109 Office Action mailed Sep. 29, 2010, 10 pgs.
U.S. Appl. No. 11/311,393 Notice of Allowance mailed Oct. 1, 2010, 3 pgs.
U.S. Appl. No. 11/380,462 Final Office Action mailed Nov. 1, 2010, 13 pgs.
U.S. Appl. No. 11/311,456 Notice of Allowance mailed Oct. 20, 2010, 1 page.
U.S. Appl. No. 11/311,043 Notice of Allowance mailed Oct. 19, 2010, 4 pages.
U.S. Appl. No. 11/311,200 Notice of Allowance mailed Oct. 12, 2010, 4 pages.
U.S. Appl. No. 11/796,577 Final Office Action mailed Nov. 15, 2010, 9 pgs.
U.S. Appl. No. 11/796,382 Final Office Action mailed Sep. 15, 2010, 10 pages.
U.S. Appl. No. 10/997,540, filed Nov. 24, 2004 entitled "A Method and System for Logging Quantitative Seizure Information and Assessing Efficacy of Therapy Using Cardiac Signals".
U.S. Appl. No. 11/741,119 Advisory Action mailed Mar. 8, 2012, 3 pages.
U.S. Appl. No. 11/741,126 Final Office Action mailed May 23, 2012, 23 pgs.
Rugg-Gunn et al. "Cardiac arrhythmias in focal epilepsy: a prospective long-term study" Dec. 18, 2004, Lancet. vol. 364 pp. 2212-2219.
U.S. Appl. No. 11/741,111 Final Office Action mailed Jul. 20, 2012, 24 pgs.

* cited by examiner

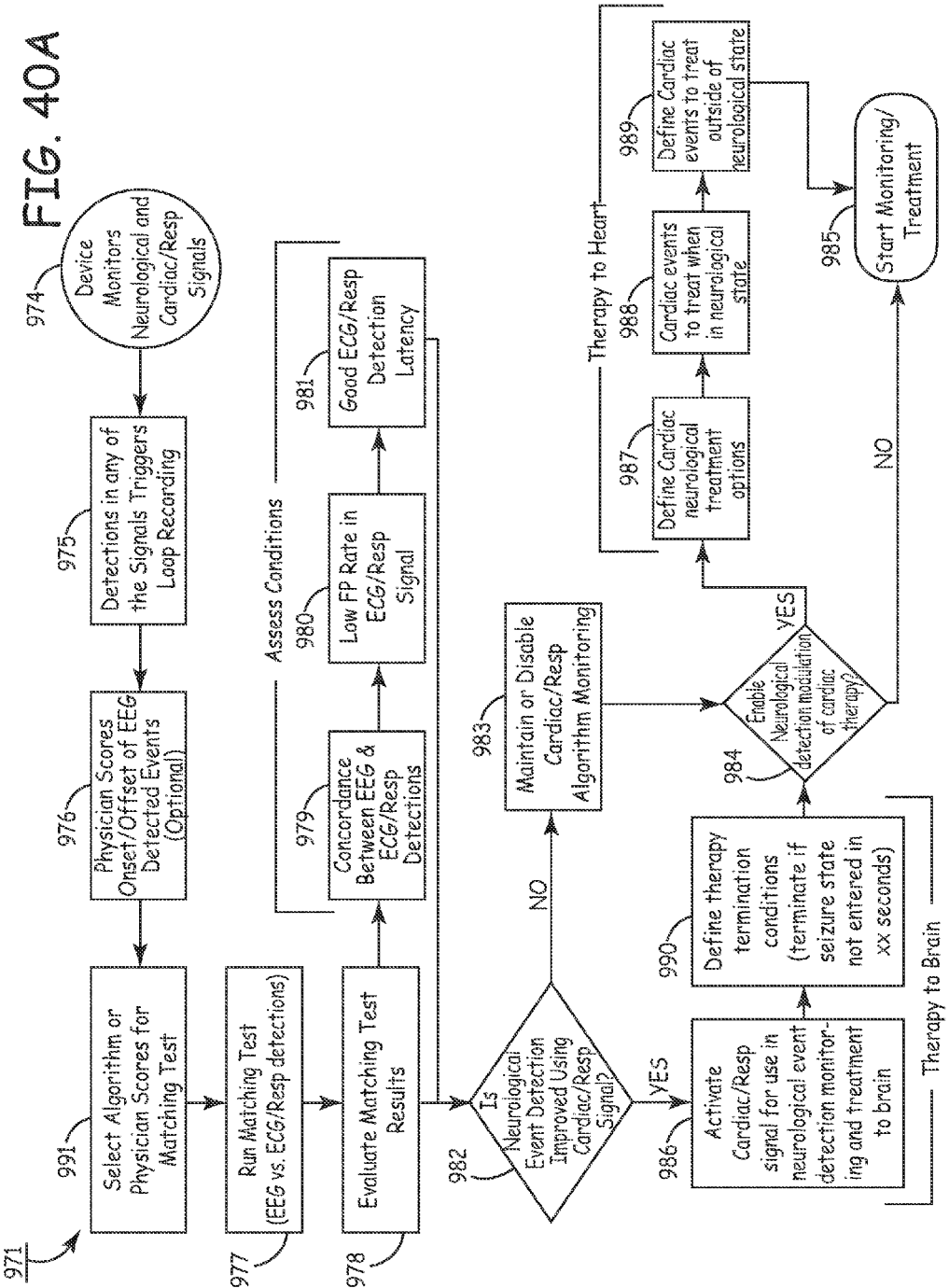

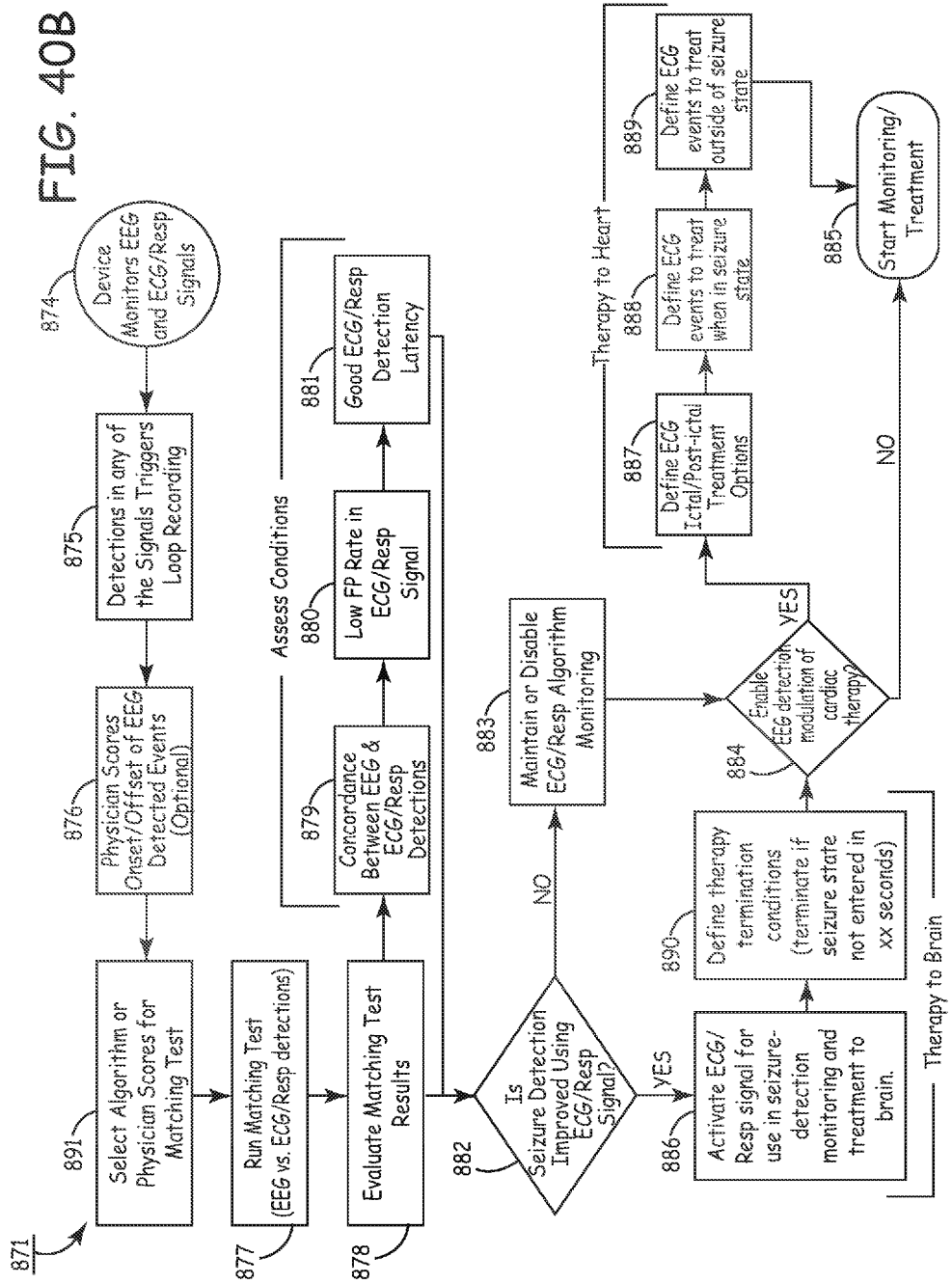

METHOD FOR MONITORING OR TREATING NERVOUS SYSTEM DISORDERS

RELATED APPLICATIONS

This application is a divisional of U.S. application Ser. No. 11/311,393, which itself claims priority to provisional U.S. application Ser. No. 60/636,929, filed Dec. 17, 2004, the contents both of which are hereby incorporated by reference in their respective entireties.

FIELD OF THE INVENTION

This invention relates generally to medical devices, and more particularly to the improved monitoring of cardiac and respiratory physiologic signals to detect and diagnose neurological events and to provide therapy to prevent or terminate neurological events.

BACKGROUND OF THE INVENTION

Nervous system disorders affect millions of people, causing death and a degradation of life. Nervous system disorders include disorders of the central nervous system, peripheral nervous system, and mental health and psychiatric disorders. Such disorders include, for example without limitation, epilepsy, Parkinson's disease, essential tremor, dystonia, and multiple sclerosis (MS). Additionally, nervous system disorders include mental health disorders and psychiatric disorders which also affect millions of individuals and include, but are not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (narcolepsy), eating disorders such as obesity, and anorexia. As an example, epilepsy is the most prevalent serious neurological disease across all ages. Epilepsy is a group of neurological conditions in which a person has or is predisposed to recurrent seizures. A seizure is a clinical manifestation resulting from excessive, hypersynchronous, abnormal electrical or neuronal activity in the brain. A neurological event is an activity that is indicative of a nervous system disorder. A seizure is a type of a neurological event. This electrical excitability of the brain may be likened to an intermittent electrical overload that manifests with sudden, recurrent, and transient changes of mental function, sensations, perceptions, or involuntary body movement. Because the seizures are unpredictable, epilepsy affects a person's employability, psychosocial life, and ability to operate vehicles or power equipment. It is a disorder that occurs in all age groups, socioeconomic classes, cultures, and countries.

There are various approaches to treating nervous system disorders. Treatment therapies can include any number of possible modalities alone or in combination including, for example, electrical stimulation, magnetic stimulation, drug infusion, or brain temperature control. Each of these treatment modalities may use open loop treatment where neither the timing of the therapy nor treatment parameters are automatically set or revised based on information coming from a sensed signal. Each of these treatment modalities may also be operated using closed-loop feedback control. Such closed-loop feedback control techniques may receive from a monitoring element a brain signal (such as EEG, ECoG, intracranial pressure, change in quantity of neurotransmitters) that carries information about a symptom or a condition of a nervous system disorder and is obtained from the head or brain of the patient.

For example, U.S. Pat. No. 5,995,868 discloses a system for the prediction, rapid detection, warning, prevention, or control of changes in activity states in the brain of a patient. Use of such a closed-loop feed back system for treatment of a nervous system disorder may provide significant advantages in that treatment can be delivered before the onset of the symptoms of the nervous system disorder.

Efficacy of treatment of nervous system disorders depends upon not only the therapy applied but also the timing of the application of the therapy. Therefore, the accuracy and timeliness of the detection algorithm and system affects the efficacy of the therapy. It is therefore desirable to develop better detection schemes and algorithms that are more accurate or are able to provide earlier detection.

One nervous system disorder that may be considered a subset of the epilepsy disease is sudden unexpected death in epilepsy, or SUDEP, is defined as sudden, unexpected, often unwitnessed, non-traumatic and non-drowning death in patients for which no cause has been found except for the individual having a history of seizures. Depending on the cohort studied, SUDEP is responsible for 2% to 18% of all deaths in patients with epilepsy, and the incidence may be up to 40 times higher in young adults with epilepsy than among persons without seizures.

Although the pathophysiological mechanisms leading to death are not fully understood, experimental, autopsy and clinical evidence implicate seizure related heart and pulmonary dysfunction or indicators. Pulmonary events may include obstructive sleep apnea (OSA), central apnea, and neurogenic pulmonary edema. Cardiac events may include cardiac arrhythmic abnormalities including sinus arrhythmia, sinus pause, premature atrial contraction (PAC), premature ventricular contraction (PVC), irregular rhythm (wandering pacemaker, multifocal atrial tachycardia, atrial fibrillation), asystole or paroxysmal tachycardia. Cardiac events may also include conduction abnormalities including AV-block (AVB) and bundle branch block (BBB) and repolarization abnormalities including T-wave inversion and ST-elevation or depression. Lastly, hypertension, hypotension and vaso-vagal syncope (VVS) are common in epilepsy patients.

Specific risk factors also play a part in sudden death in epilepsy—ie, age (young), gender (male), poor seizure control, nocturnal seizures, severity and quantity of seizures, poor compliance with medicants, alcohol or drug use, and stress.

Epileptic seizures are associated with autonomic neuronal dysfunction that result in a broad array of abnormalities of cardiac and pulmonary function. Different pathophysiological events may contribute to SUDEP in different patients, and the mechanism is probably multifactorial. Without intervention, respiratory events, including airway obstruction, central apnea and neurogenic pulmonary edema are probably terminal events. In addition, cardiac arrhythmia and anomalies, during the ictal and interictal periods, leading to arrest and acute cardiac failure also plays an important role in potentially terminal events. For example, the paper "Electrocardiographic Changes at Seizure Onset", Leutmezer, et al, Epilepsia 44(3): 348-354, 2003 describes cardiovascular anomalies, such as heart rate variability (HRV), tachycardia and bradycardia, that may precede, occur simultaneous or lag behind EEG seizure onset. "Cardiac Asystole in Epilepsy: Clinical and Neurophysiologic Features", Rocamora, et al, Epilepsia 44(2): 179-185, 2003 reports that cardiac asystole is "provoked" by the seizure. "Electrocardiograph QT Lengthening Associated with Epileptiform EEG Discharges—a Role in Sudden Unexplained Death in Epilepsy", Tavernor, et al, Seizure 5(1): 79-83, March 1996 reports QT lengthening during seizures in SUDEP patients versus control. "Effects of Seizures on Autonomic and Cardiovascular Function", Devinsky Epilepsy Currents 4(2): 43-46, March/April 2004 describes ST segment depression and T-wave inversion, AVB, VPC and BBB during or immediately after a seizure. "Sudden Unexplained Death in Children with Epilepsy", Donner, et al, Neurology 57: 430-434, 2001 reports that bradycardia is frequently preceded by hypoventilation or apnea suggesting that heart rate changes during seizures may be a result of cardiorespiratory reflexes. Lastly, "EEG and ECG in Sudden Unexplained Death in Epilepsy", Nei, et al, Epilepsia 45(4) 338-345, 2004 reports on sinus tachycardia during or after seizures.

Obstructive sleep apnea is often associated with epilepsy and SUDEP at risk patients. OSA is typically treated with continuous positive airway pressure (CPAP), oral appliances, surgery, positional therapy or weight loss. These often are not totally successful or device (CPAP or appliance) compliance is low.

With the above broad and, often conflicting, array of neuro cardiopulmonary physiological anomalies, manifestations and indicators, a flexible multi-programmable device, or array of flexible multi-programmable devices, is desired to allow for better diagnosis, monitoring and treatment of nervous system disorders.

SUMMARY OF THE INVENTION

In one embodiment of the invention, a medical device system is provided that includes a brain monitoring element, cardiac monitoring element and a processor. The processor is configured to receive a brain signal from the brain monitoring element and a cardiac signal from the cardiac monitoring element. The processor is further configured to compare the brain signal to the cardiac signal. Many embodiments of such a comparison are provided. A method of comparing a brain signal to a cardiac signal is also provided.

BRIEF DESCRIPTION OF THE DRAWINGS

Core Monitor

Full Monitor

Figure 5:
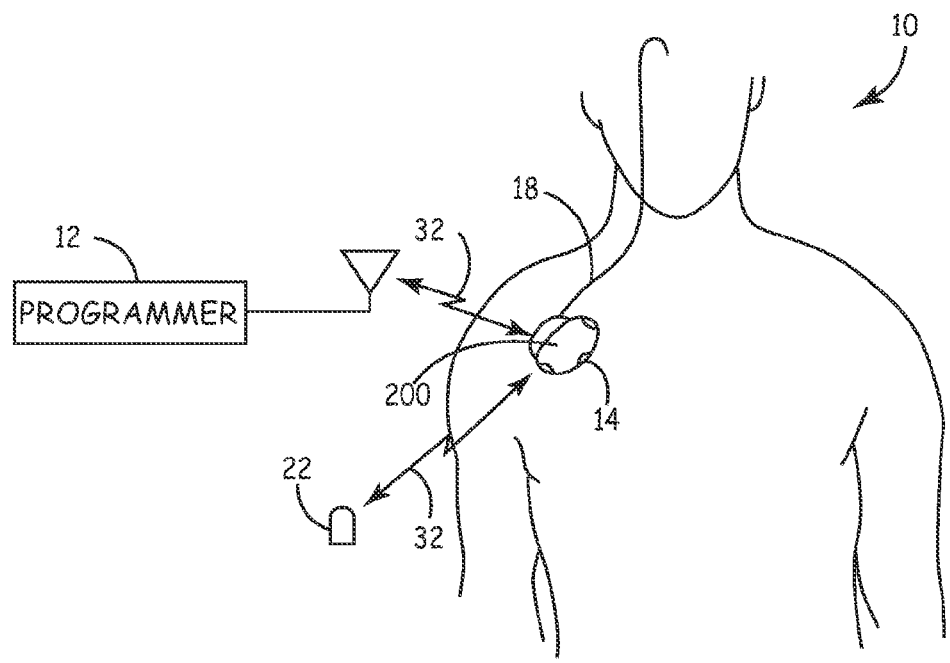

FIG. 5 is a simplified schematic view of an alternative embodiment thoracic leadless and cranial leaded medical device implanted in a patient that monitors cardiac, respiratory and brain parameters relating to nervous system disorder.

Figure 6:
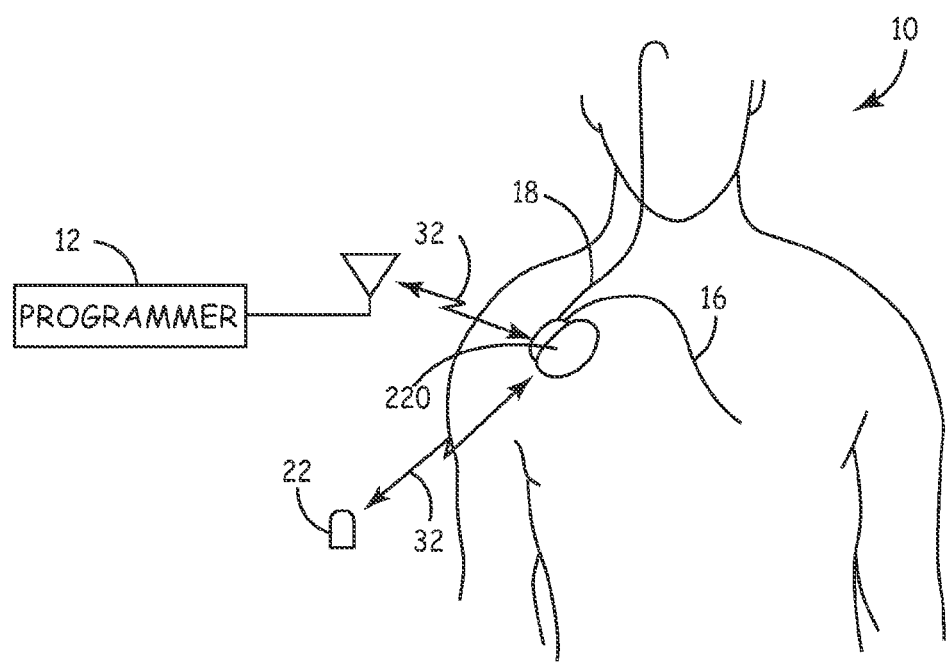

FIG. 6 is a simplified schematic view of an alternative embodiment cardiac and cranial leaded medical device implanted in a patient that monitors cardiac, respiratory and brain parameters relating to nervous system disorder.

Figure 7:
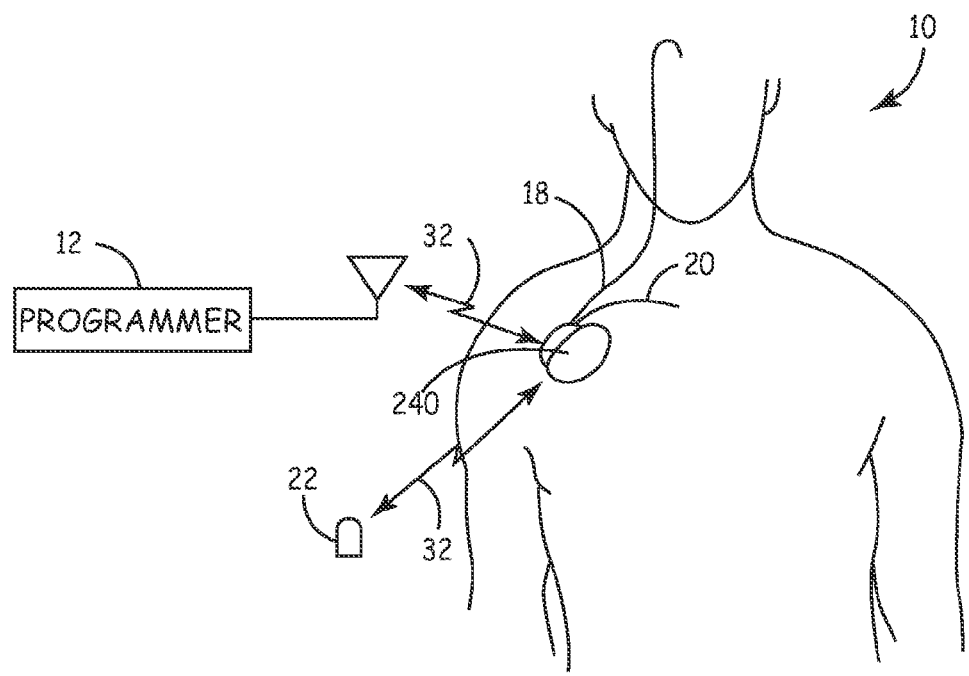

FIG. 7 is a simplified schematic view of an alternative embodiment sensor stub and cranial leaded medical device implanted in a patient that monitors cardiac, respiratory and brain parameters relating to nervous system disorder.

Figure 8:
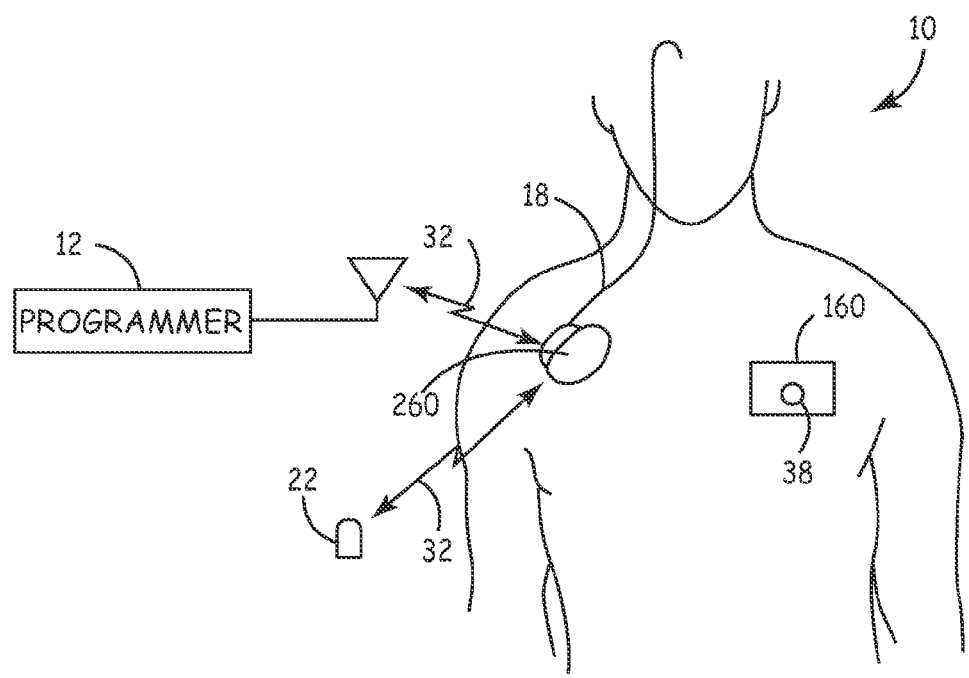

FIG. 8 is a simplified schematic view of an alternative embodiment external patch and cranial leaded medical device implanted in a patient that monitors cardiac, respiratory and brain parameters relating to nervous system disorder.

Figure 9:
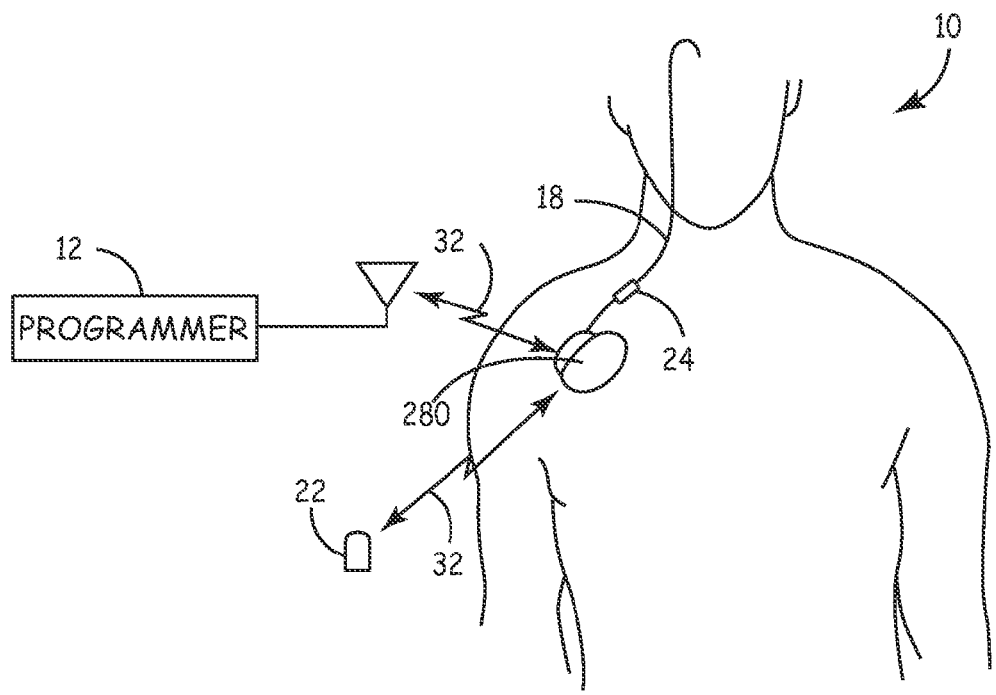

FIG. 9 is a simplified schematic view of an alternative embodiment integrated brain lead medical device implanted in a patient that monitors cardiac, respiratory and brain parameters relating to nervous system disorder.

Figure 10:
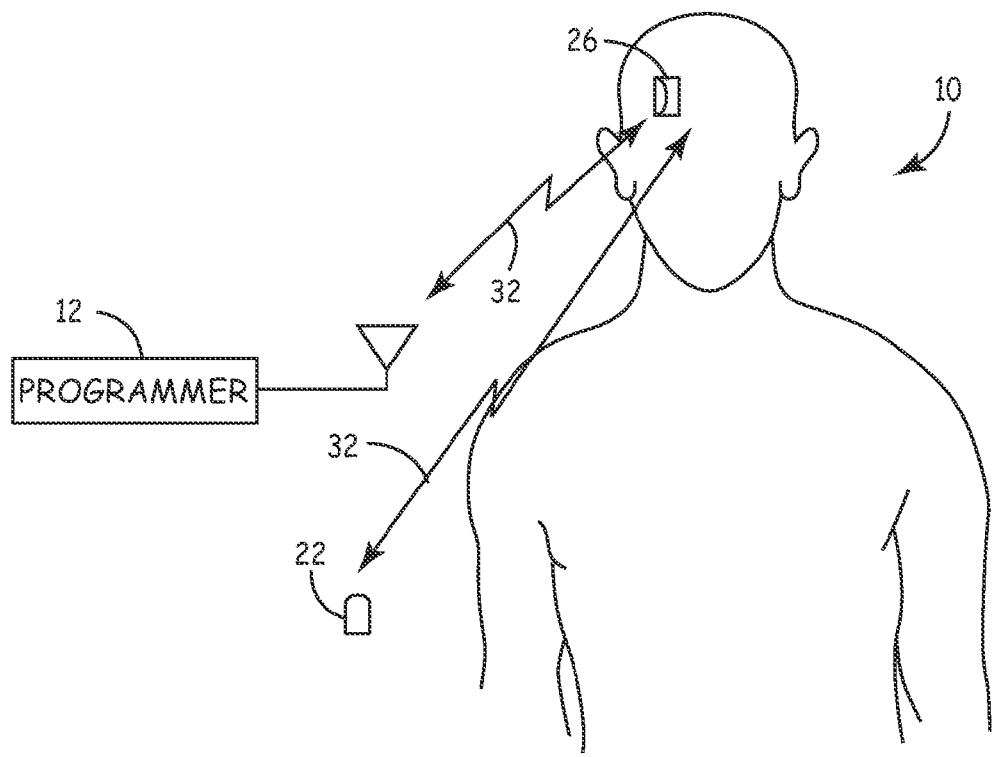

FIG. 10 is a simplified schematic view of an alternative embodiment cranial implant medical device implanted in a patient that monitors cardiac and brain parameters relating to nervous system disorder.

Monitor+Treatment (Brain)

Figure 11:
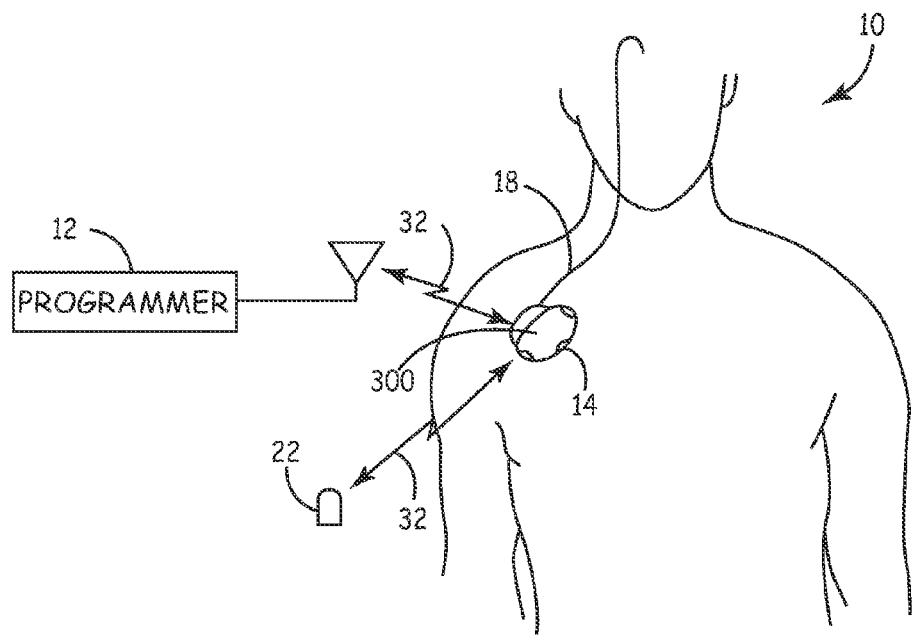

FIG. 11 is a simplified schematic view of an alternative embodiment thoracic leadless and cranial leaded medical device implanted in a patient that monitors cardiac, respiratory and brain parameters relating to nervous system disorders and provides brain treatment.

Figure 12A:
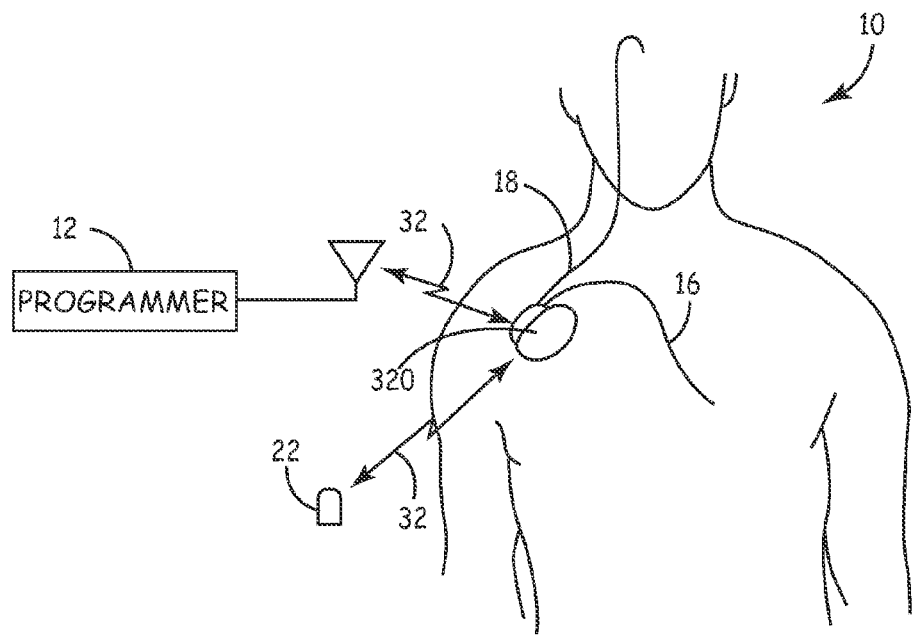

FIG. 12A is a simplified schematic view of an alternative embodiment cardiac and cranial leaded medical device implanted in a patient that monitors cardiac, respiratory and brain parameters relating to nervous system disorders and provides brain treatment.

Figure 12B:
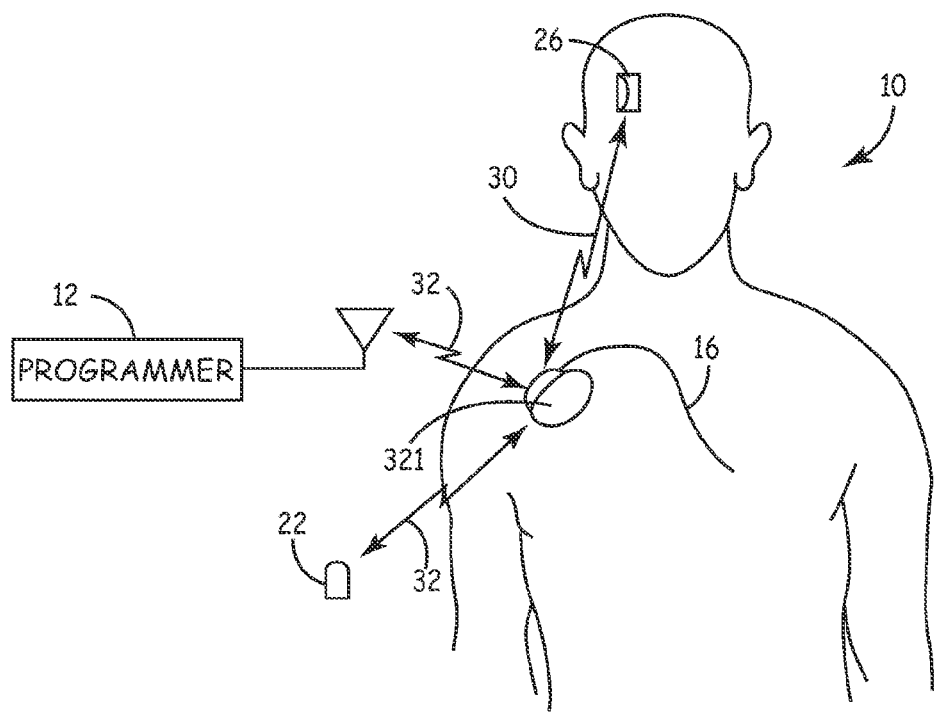

FIG. 12B is a simplified schematic view of an alternative embodiment cardiac and cranial leaded medical device implanted in a patient that monitors cardiac, respiratory and brain parameters relating to nervous system disorders and provides brain treatment.

Figure 13:
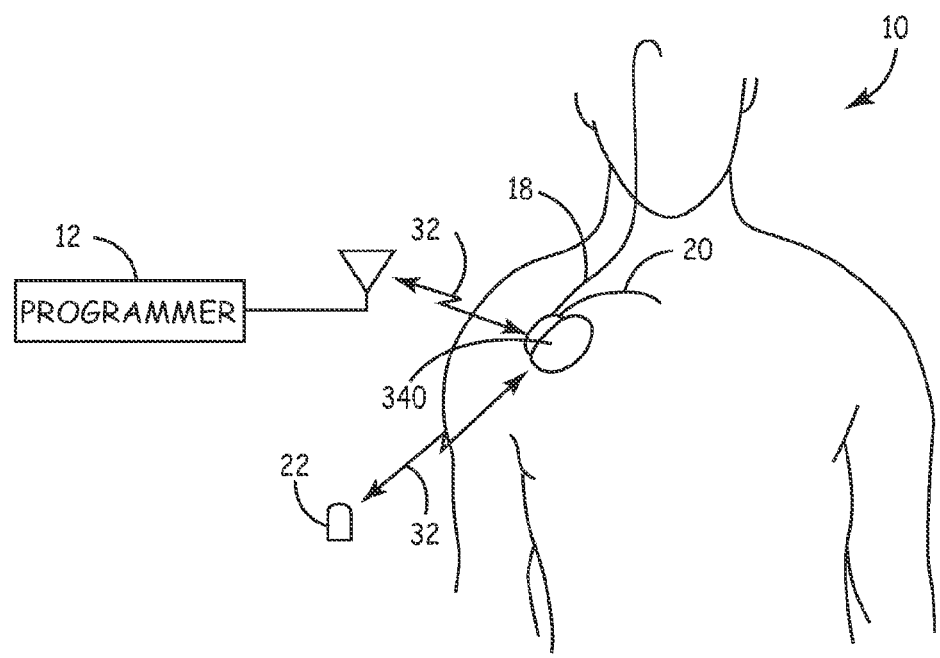

FIG. 13 is a simplified schematic view of an alternative embodiment sensor stub and cranial leaded medical device implanted in a patient that monitors cardiac, respiratory and brain parameters relating to nervous system disorders and provides brain treatment.

Figure 14:
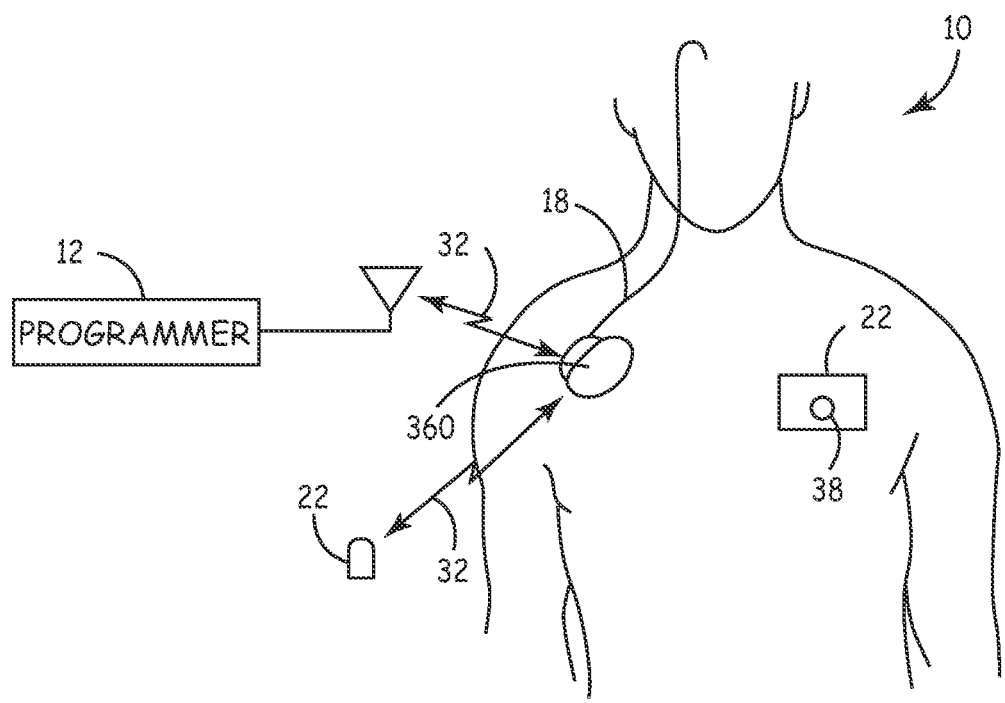

FIG. 14 is a simplified schematic view of an alternative embodiment external patch and cranial leaded medical device implanted in a patient that monitors cardiac, respiratory and brain parameters relating to nervous system disorders and provides brain treatment.

Figure 15:
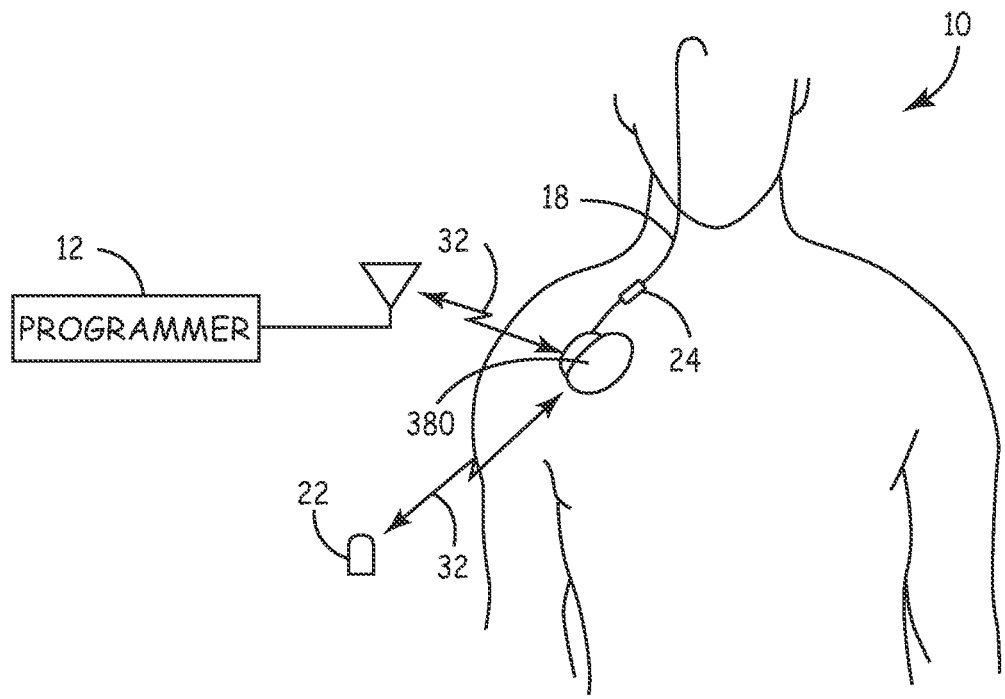

FIG. 15 is a simplified schematic view of an alternative embodiment integrated brain lead medical device implanted in a patient that monitors cardiac, respiratory and brain parameters relating to nervous system disorders and provides brain treatment.

Figure 20:
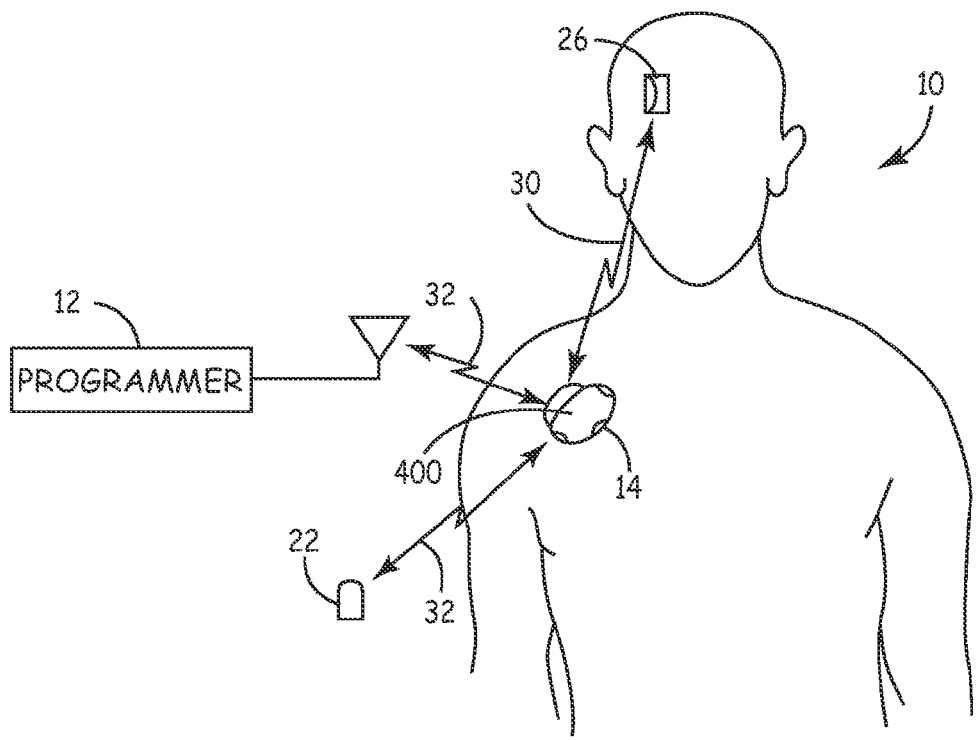

FIG. 20 is a simplified schematic view of an alternative embodiment thoracic leadless device to cranial implant via wireless connect medical device implanted in a patient that monitors cardiac, respiratory and brain parameters relating to nervous system disorders and provides brain treatment.

Figure 21:
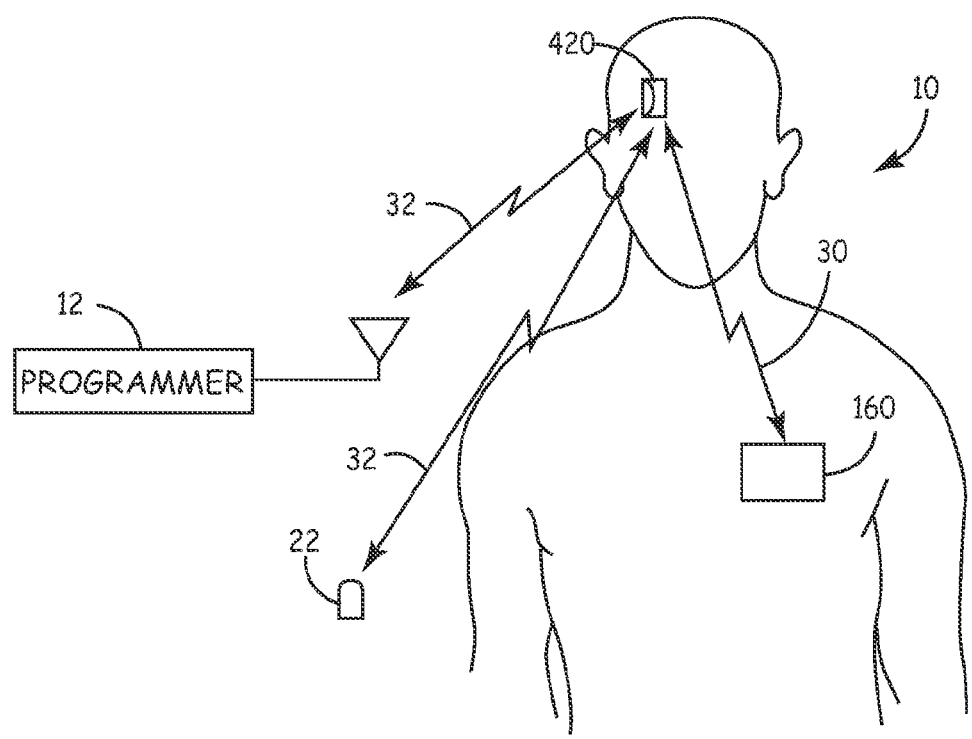

FIG. 21 is a simplified schematic view of an alternative embodiment external patch to cranial implant via wireless connect medical device implanted in a patient that monitors cardiac, respiratory and brain parameters relating to nervous system disorders and provides brain treatment.

Monitor+Treatment (Brain+Respiration)

Figure 16A:
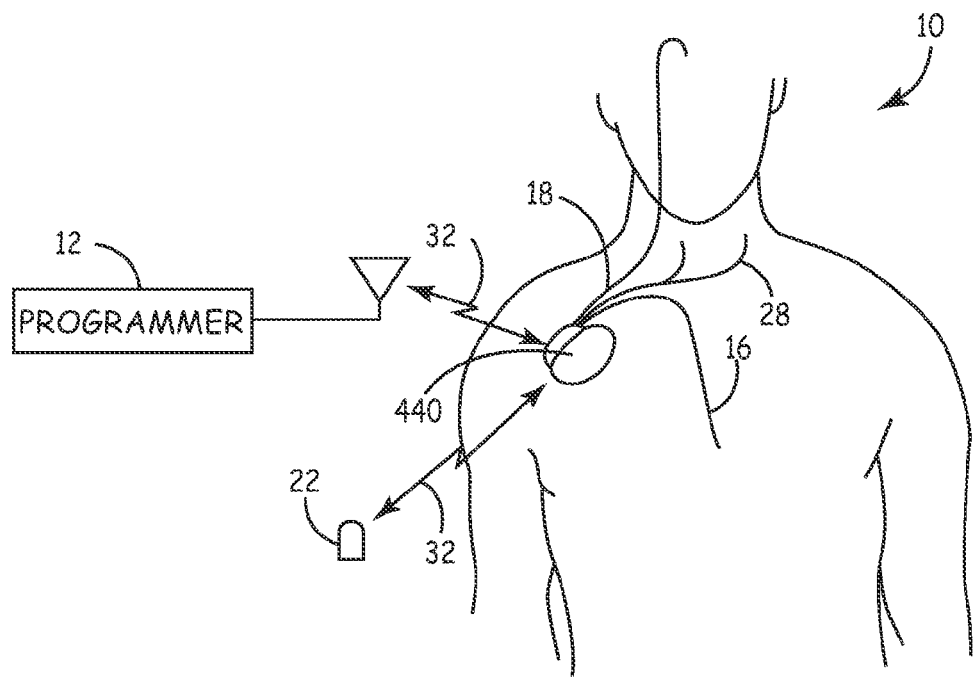

FIG. 16A is a simplified schematic view of an alternative embodiment cardiac, brain and phrenic nerve leaded medical device implanted in a patient that monitors cardiac, respiratory and brain parameters relating to nervous system disorders and provides brain and respiration treatment.

Figure 16B:
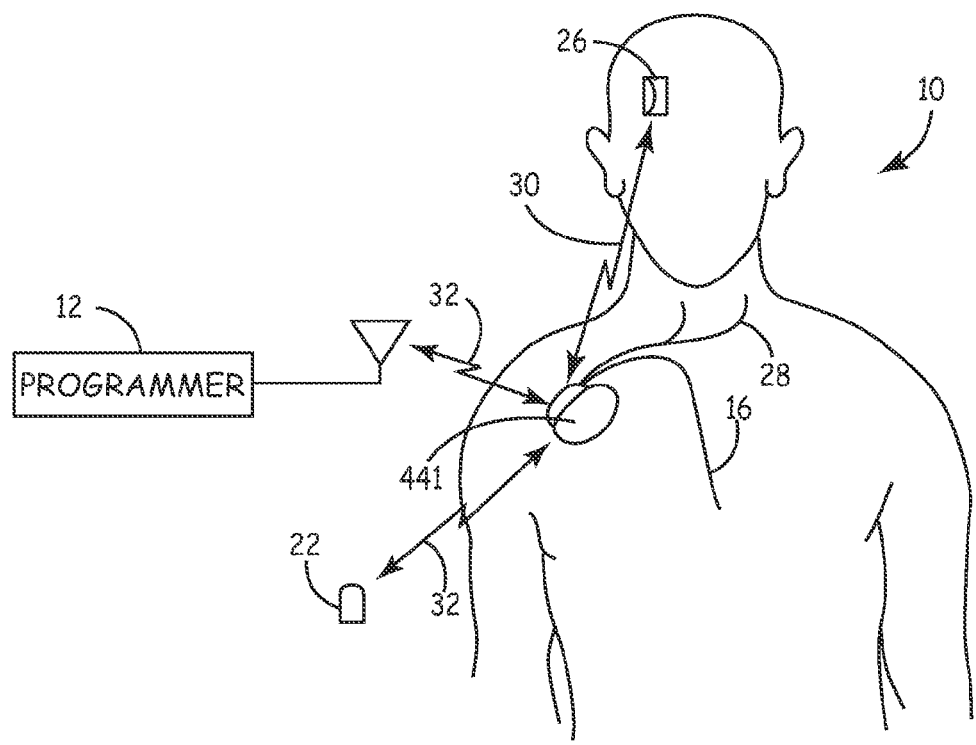

FIG. 16B is a simplified schematic view of an alternative embodiment cardiac, brain and phrenic nerve leaded medical device implanted in a patient that monitors cardiac, respiratory and brain parameters relating to nervous system disorders and provides brain and respiration treatment.

Figure 17:
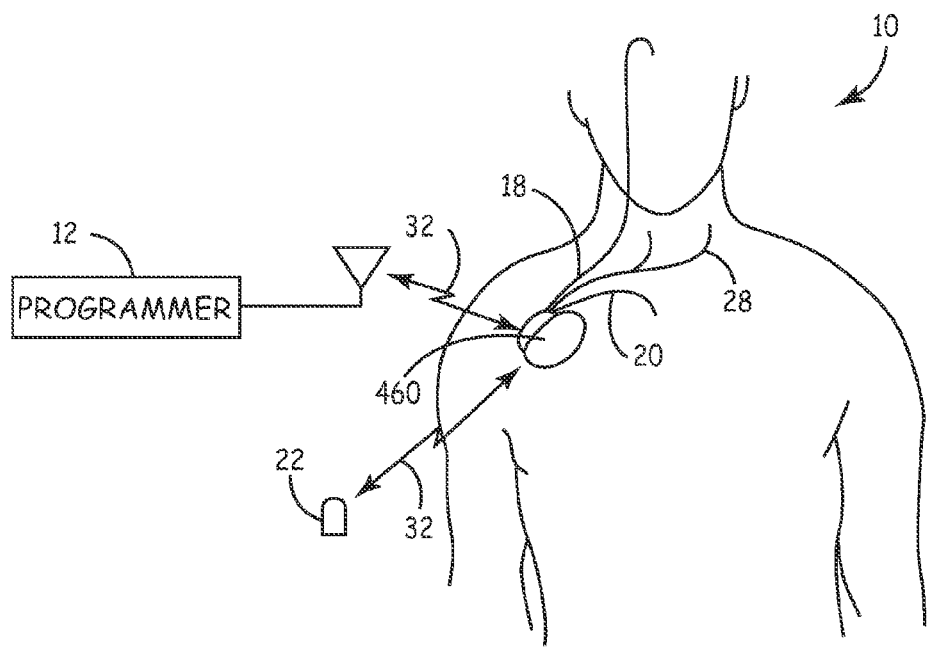

FIG. 17 is a simplified schematic view of an alternative embodiment sensor stub, brain and phrenic nerve leaded medical device implanted in a patient that monitors cardiac, respiratory and brain parameters relating to nervous system disorders and provides brain and respiration treatment.

Figure 18:
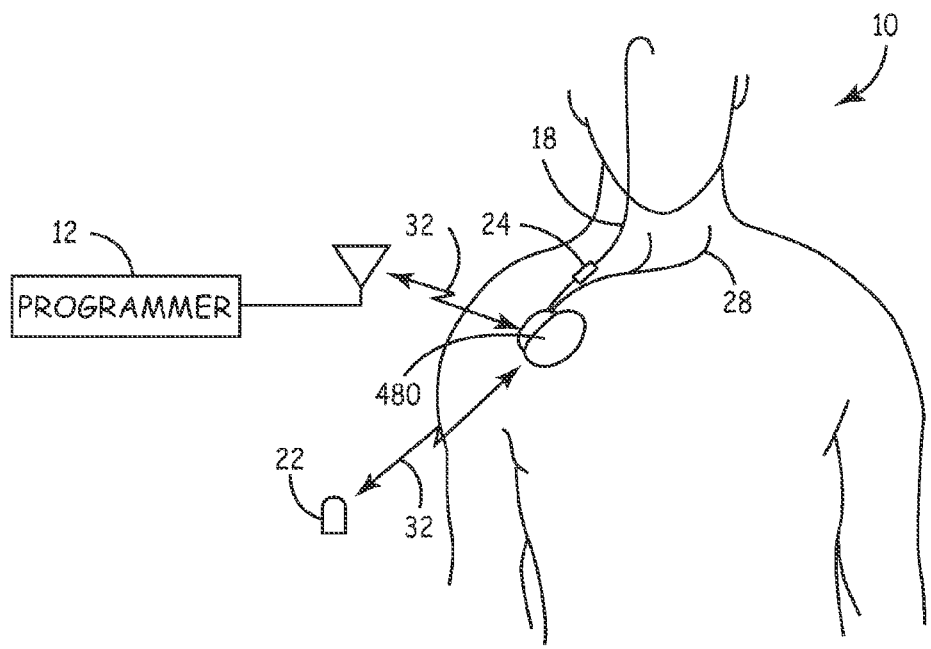

FIG. 18 is a simplified schematic view of an alternative embodiment integrated brain and phrenic nerve leaded medical device implanted in a patient that monitors cardiac, respiratory and brain parameters relating to nervous system disorders and provides brain and respiration treatment.

Figure 19:
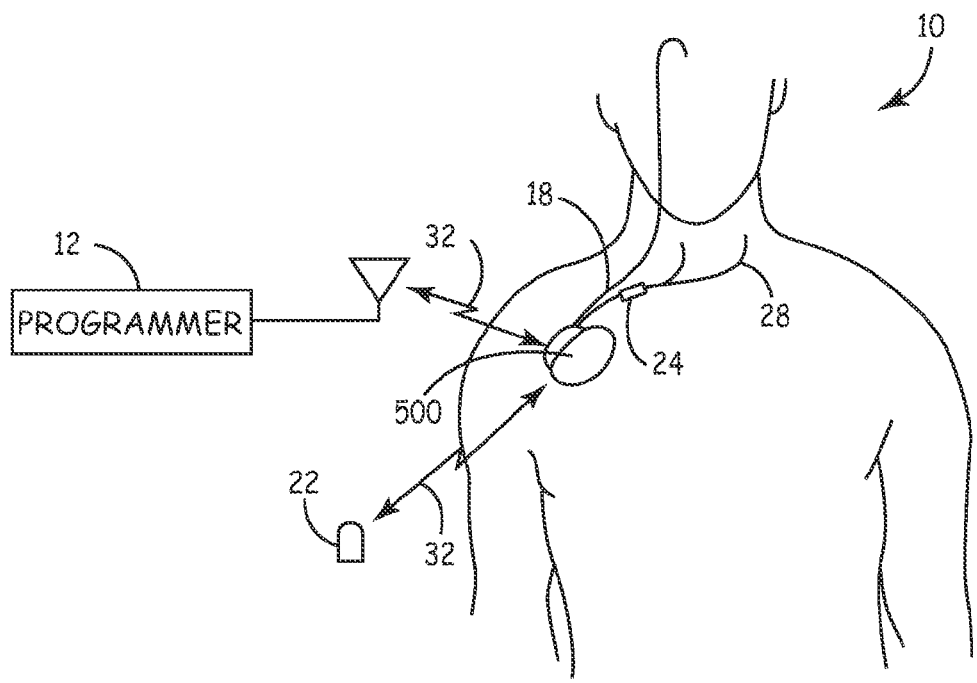

FIG. 19 is a simplified schematic view of an alternative embodiment brain and integrated respiration lead medical device implanted in a patient that monitors cardiac, respiratory and brain parameters relating to nervous system disorders and provides brain and respiration treatment.

Monitor+Treatment (Brain+Cardiac)

Figure 24A:
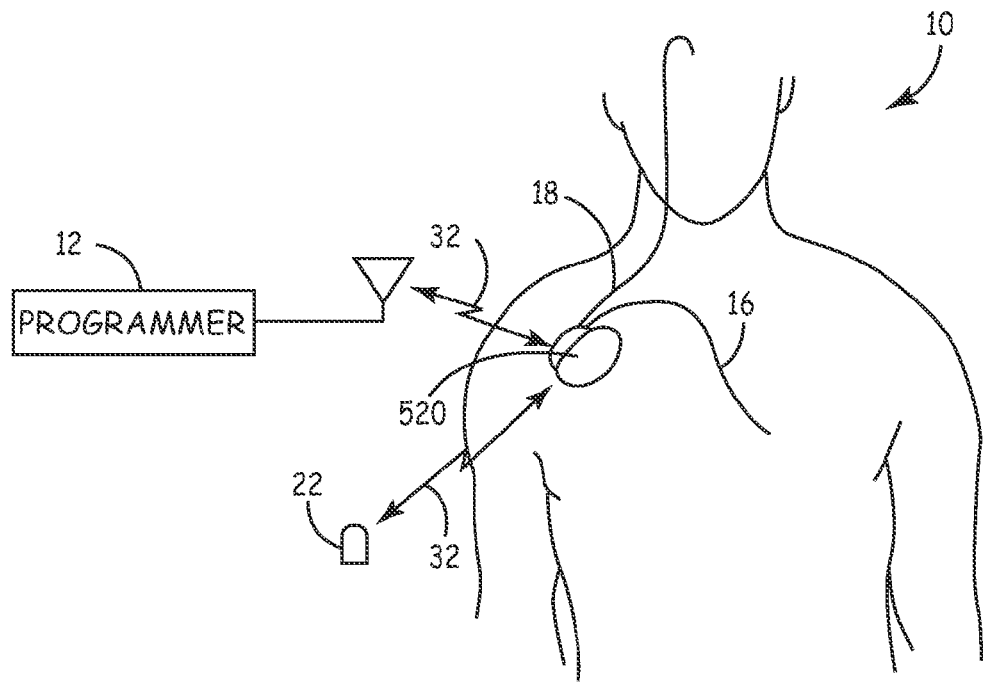

FIG. 24A is a simplified schematic view of an alternative embodiment cardiac and brain leaded medical device implanted in a patient that monitors cardiac, respiratory and brain parameters relating to nervous system disorders and provides brain and cardiac treatment.

Figure 24B:
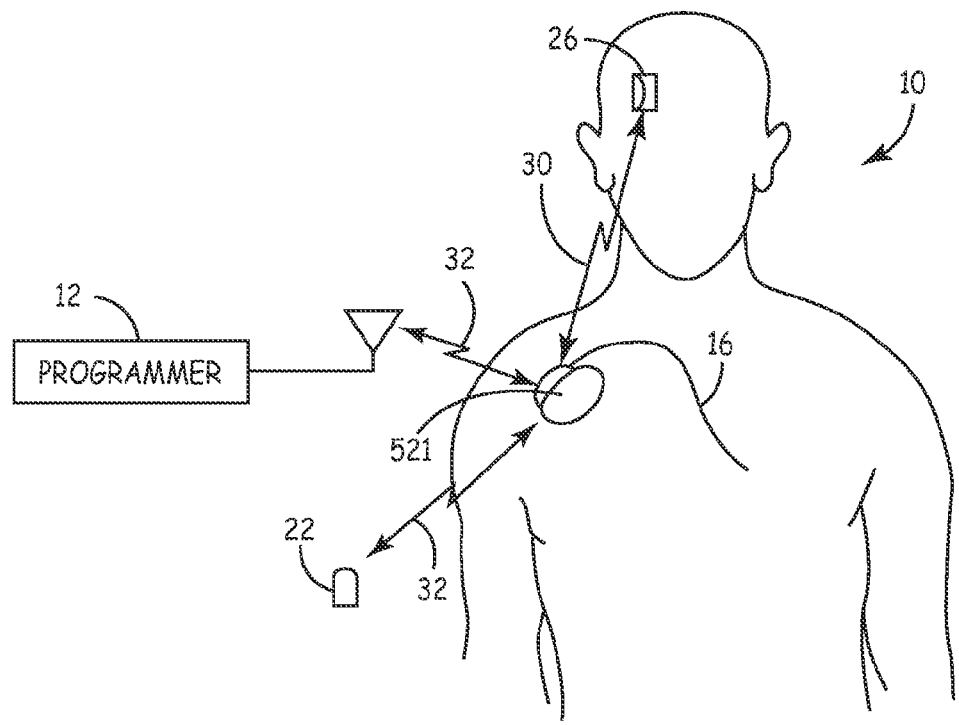

FIG. 24B is a simplified schematic view of an alternative embodiment cardiac and brain leaded medical device implanted in a patient that monitors cardiac, respiratory and brain parameters relating to nervous system disorders and provides brain and cardiac treatment.

Figure 22:
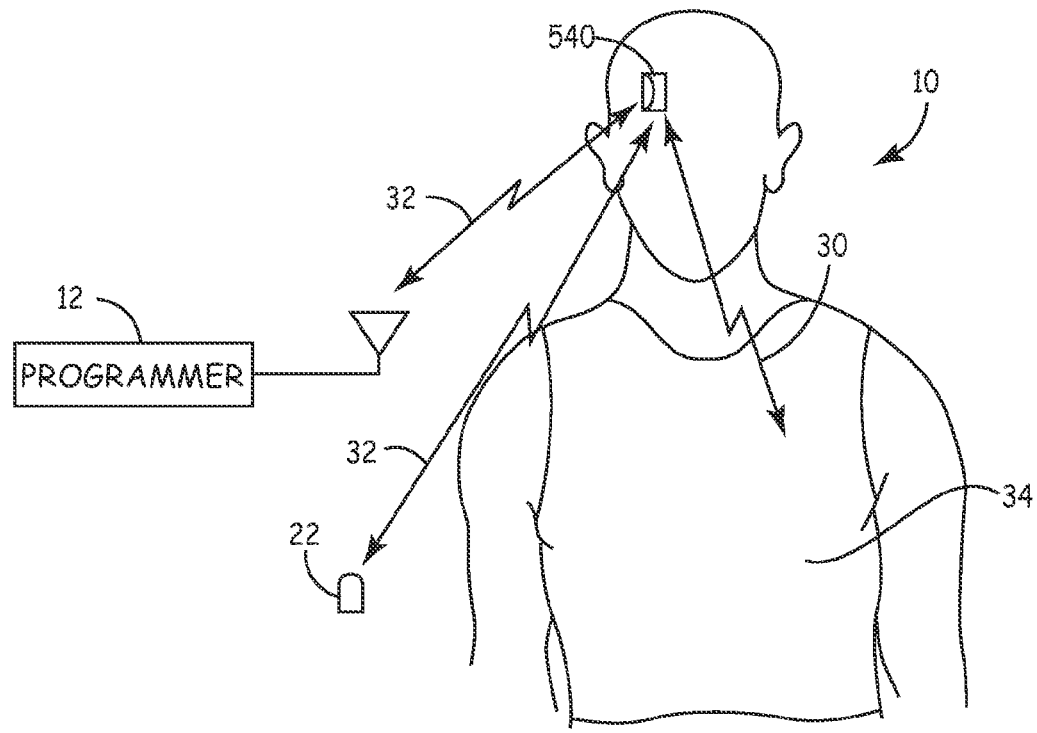

FIG. 22 is a simplified schematic view of an alternative embodiment cranial implant to defibrillator vest via wireless connect medical device used by a patient that monitors cardiac, respiratory and brain parameters relating to nervous system disorders and provides brain and cardiac treatment.

Figure 23:
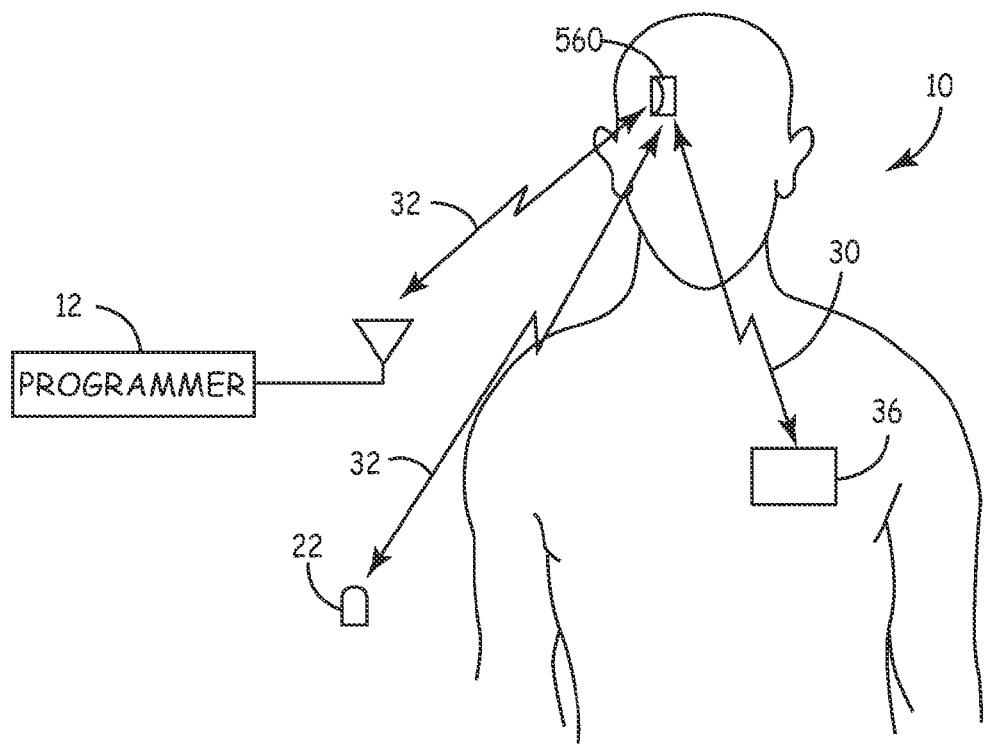

FIG. 23 is a simplified schematic view of an alternative embodiment cranial implant to leadless defibrillator (lifeboat) via wireless connect medical device used by a patient that monitors cardiac, respiratory and brain parameters relating to nervous system disorders and provides brain and cardiac treatment.

Monitor+Treatment (Brain+Respiration+Cardiac)

Figure 25A:
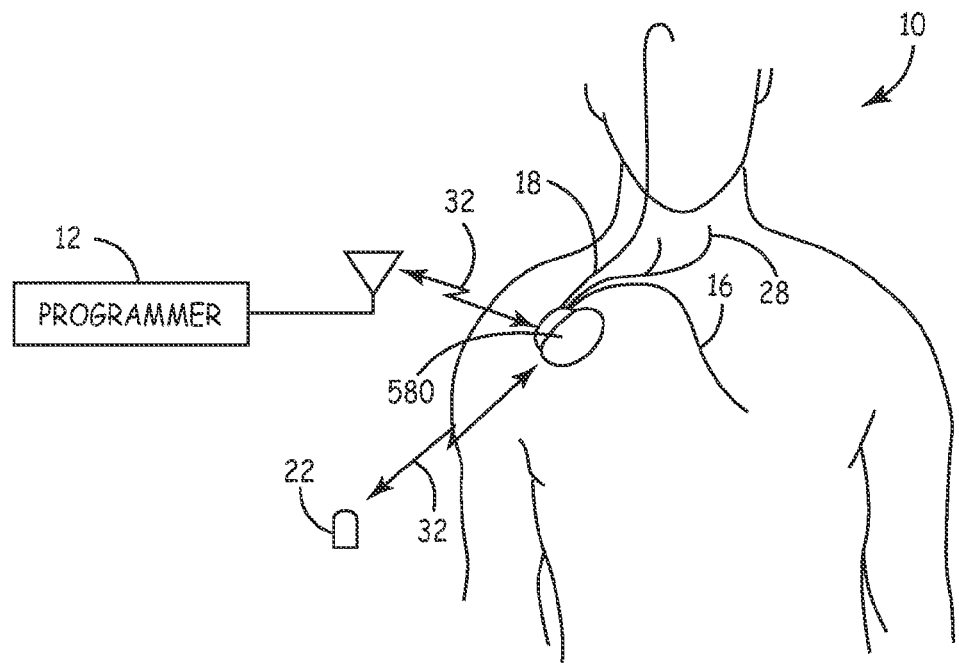

FIG. 25A is a simplified schematic view of an alternative embodiment cardiac, cranial and phrenic nerve leaded medical device implanted in a patient that monitors cardiac, respiratory and brain parameters relating to nervous system disorders and provides brain and respiration and cardiac treatment.

Figure 25B:
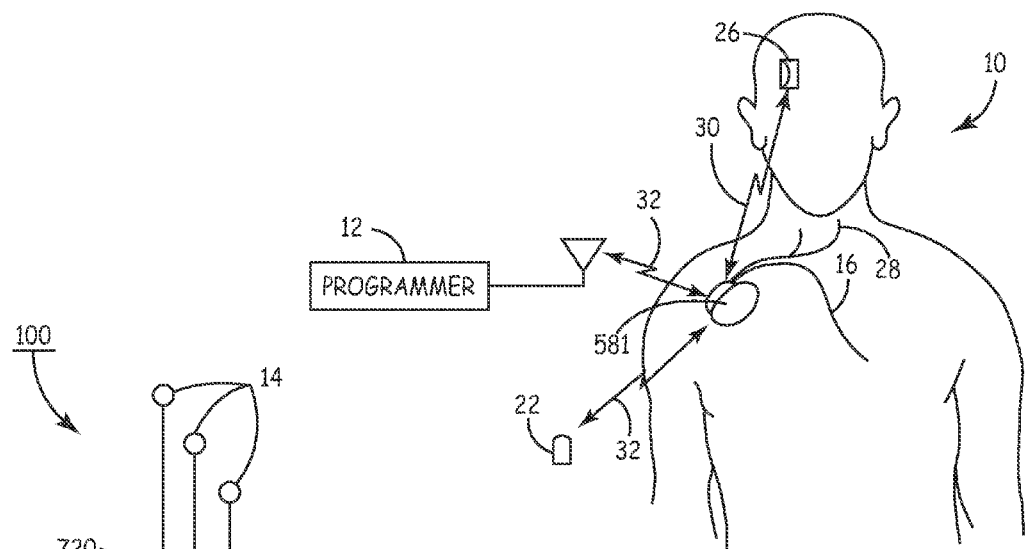

FIG. 25B is a simplified schematic view of an alternative embodiment cardiac, cranial and phrenic nerve leaded medical device implanted in a patient that monitors cardiac, respiratory and brain parameters relating to nervous system disorder and provides brain and respiration and cardiac treatment.

Detailed Design

Figure 1:
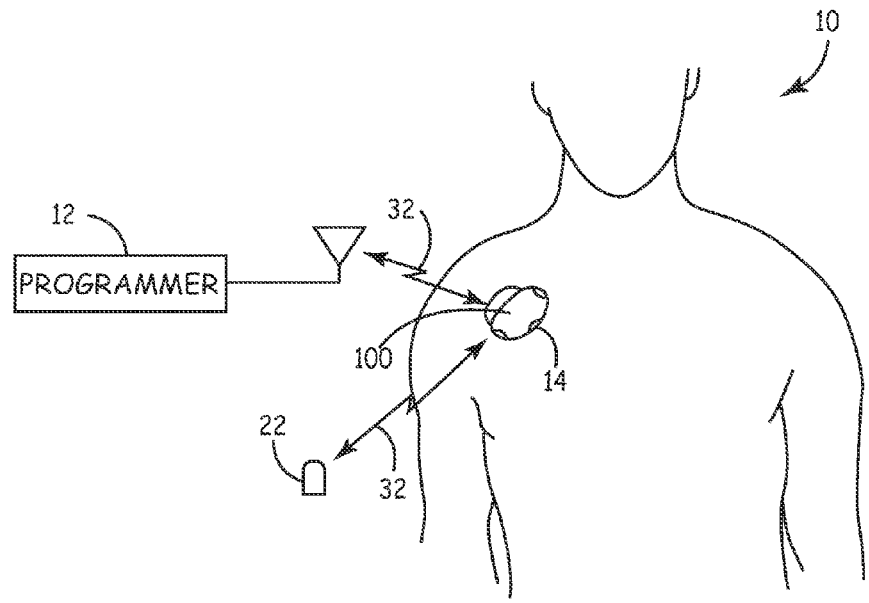
FIG. 1 is a simplified schematic view of a thoracic cavity leadless medical device implanted in a patient that monitors cardiac and respiratory parameters relating to a nervous system disorder.
Figure 26:
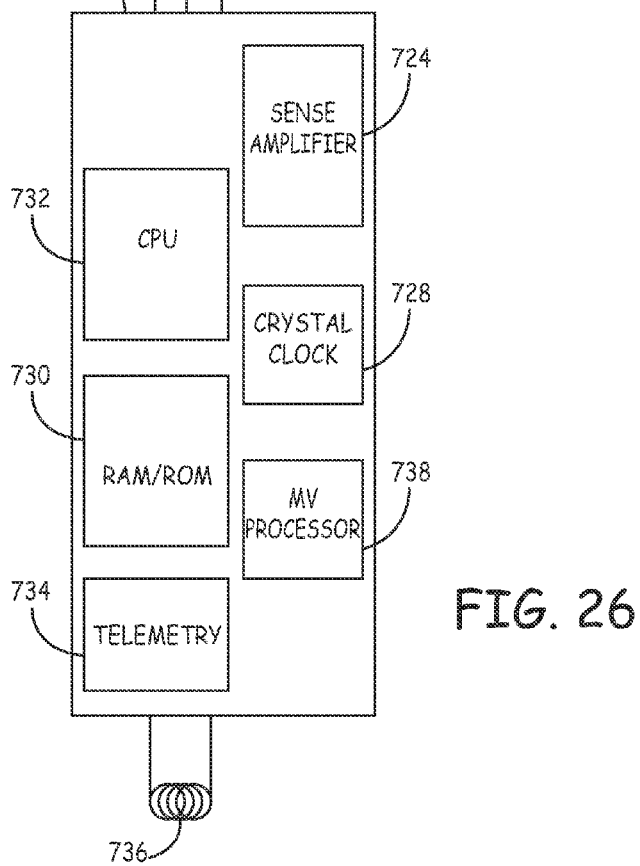

FIG. 26 is a simplified block diagram of a core monitor as shown in FIG. 1 above.

Figure 27:
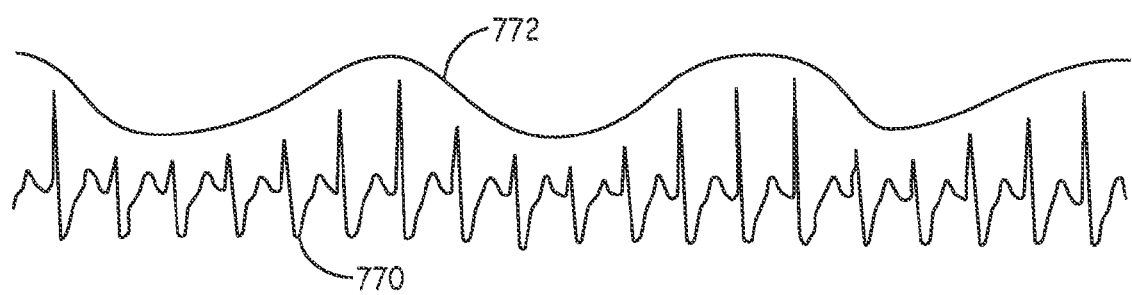

FIG. 27 is a graphical representation of the signals sensed by core monitor as shown in FIG. 1 above.

Figure 2:
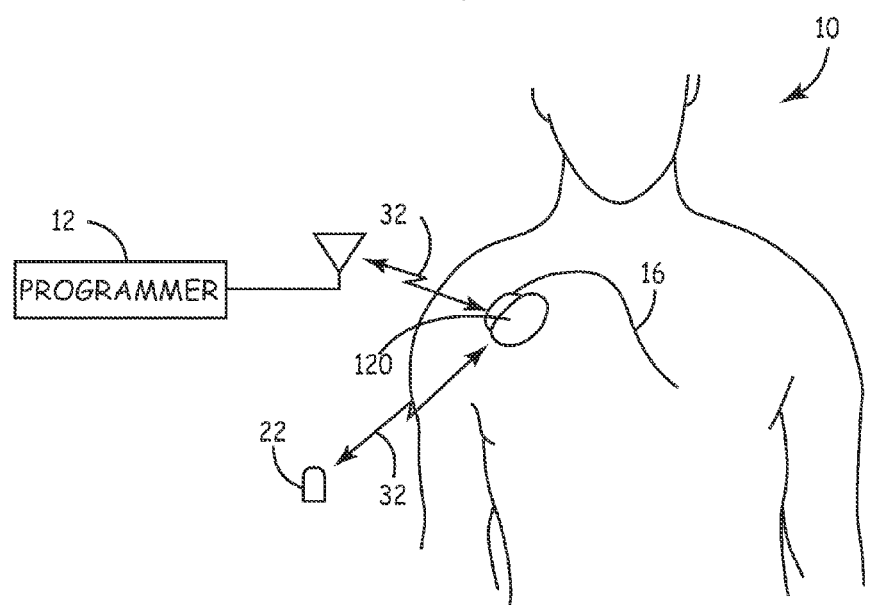
FIG. 2 is a simplified schematic view of an alternative embodiment cardiac leaded medical device implanted in a patient that monitors cardiac and respiratory parameters relating to nervous system disorder.
Figure 28:
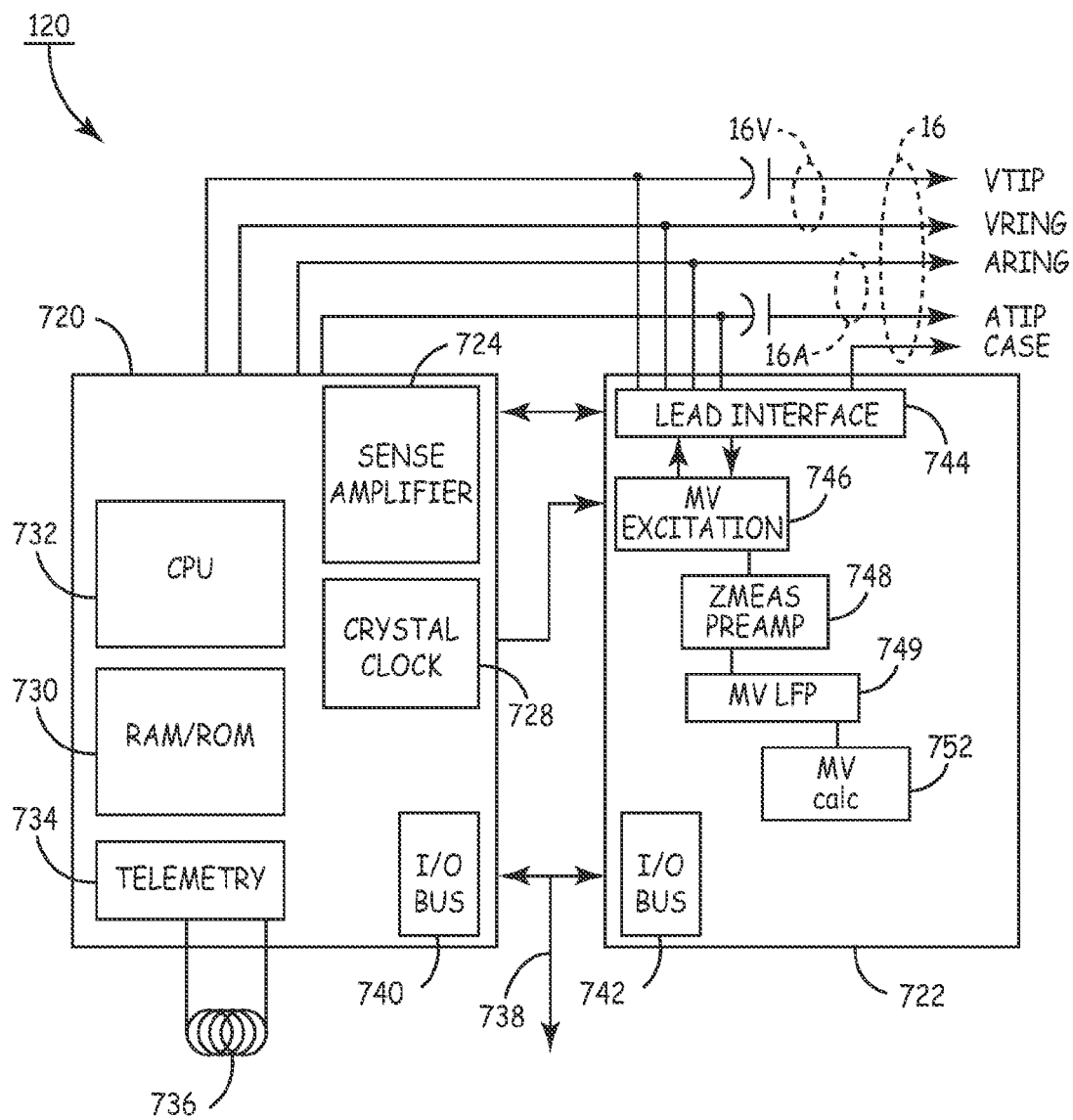

FIG. 28 is a simplified block diagram of a core monitor as shown in FIG. 2 above.

Figure 3:
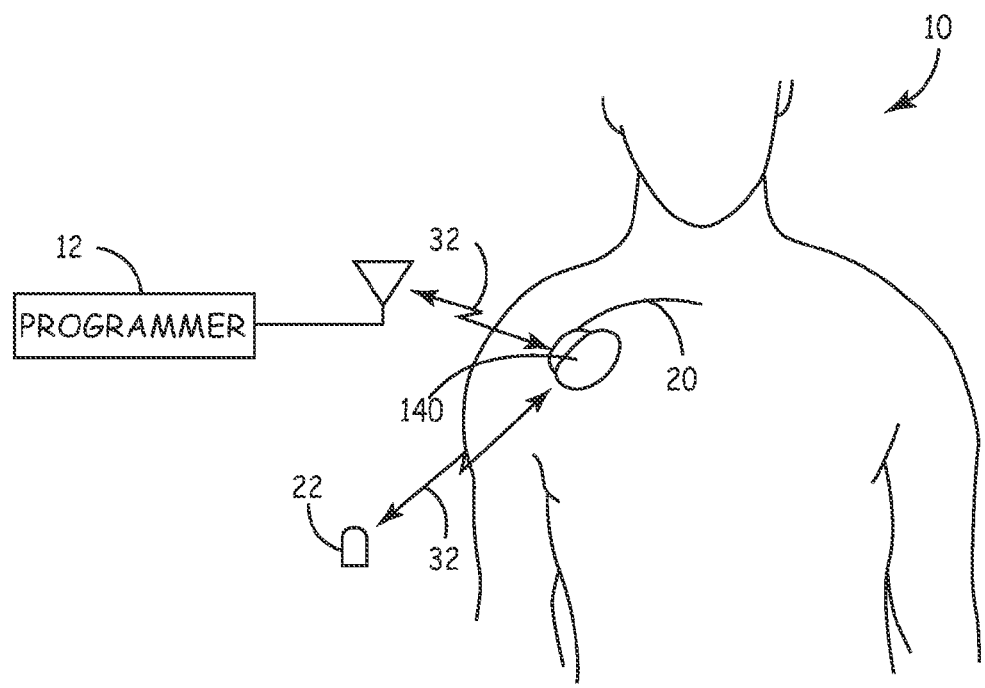
FIG. 3 is a simplified schematic view of an alternative embodiment sensor stub medical device implanted in a patient that monitors cardiac and respiratory parameters relating to nervous system disorder.
Figure 29:
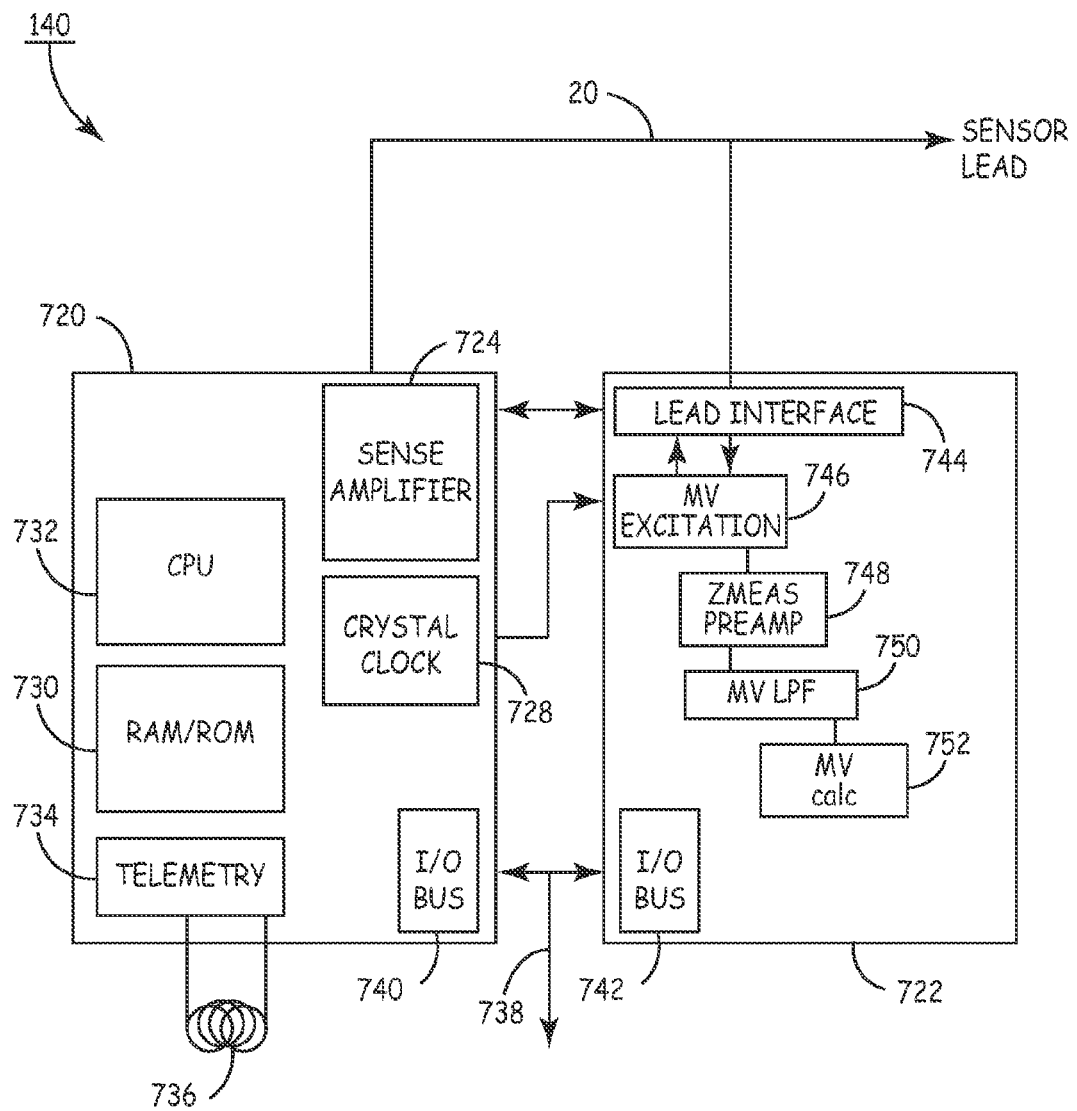

FIG. 29 is a simplified block diagram of a core monitor as shown in FIG. 3 above.

Figure 4:
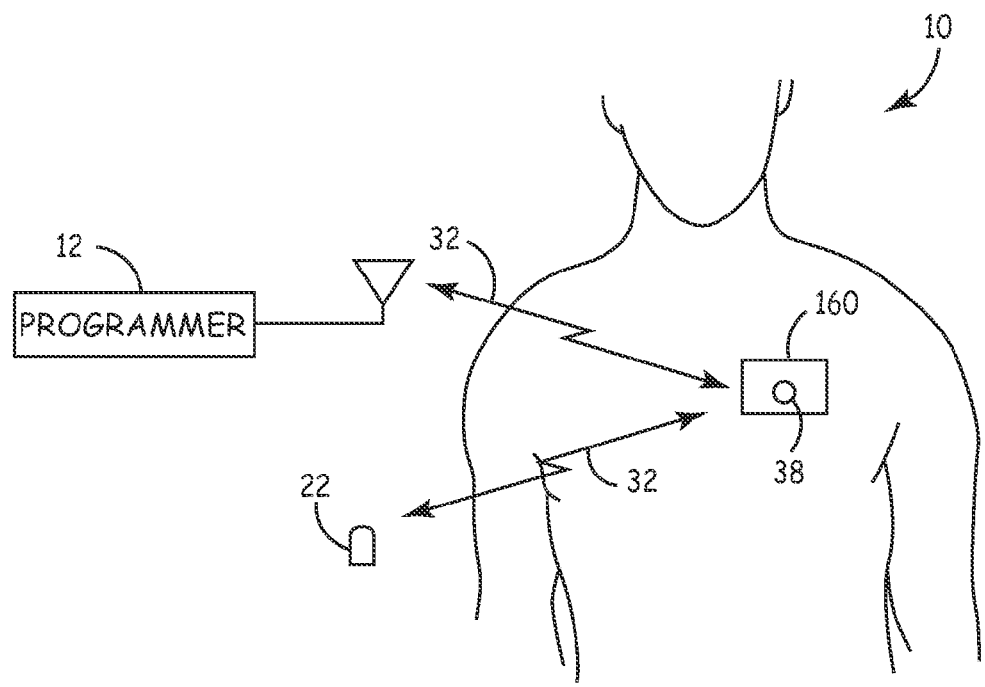
FIG. 4 is a simplified schematic view of an alternative embodiment external patch medical device used by a patient that monitors cardiac and respiratory parameters relating to nervous system disorder.
Figure 30:
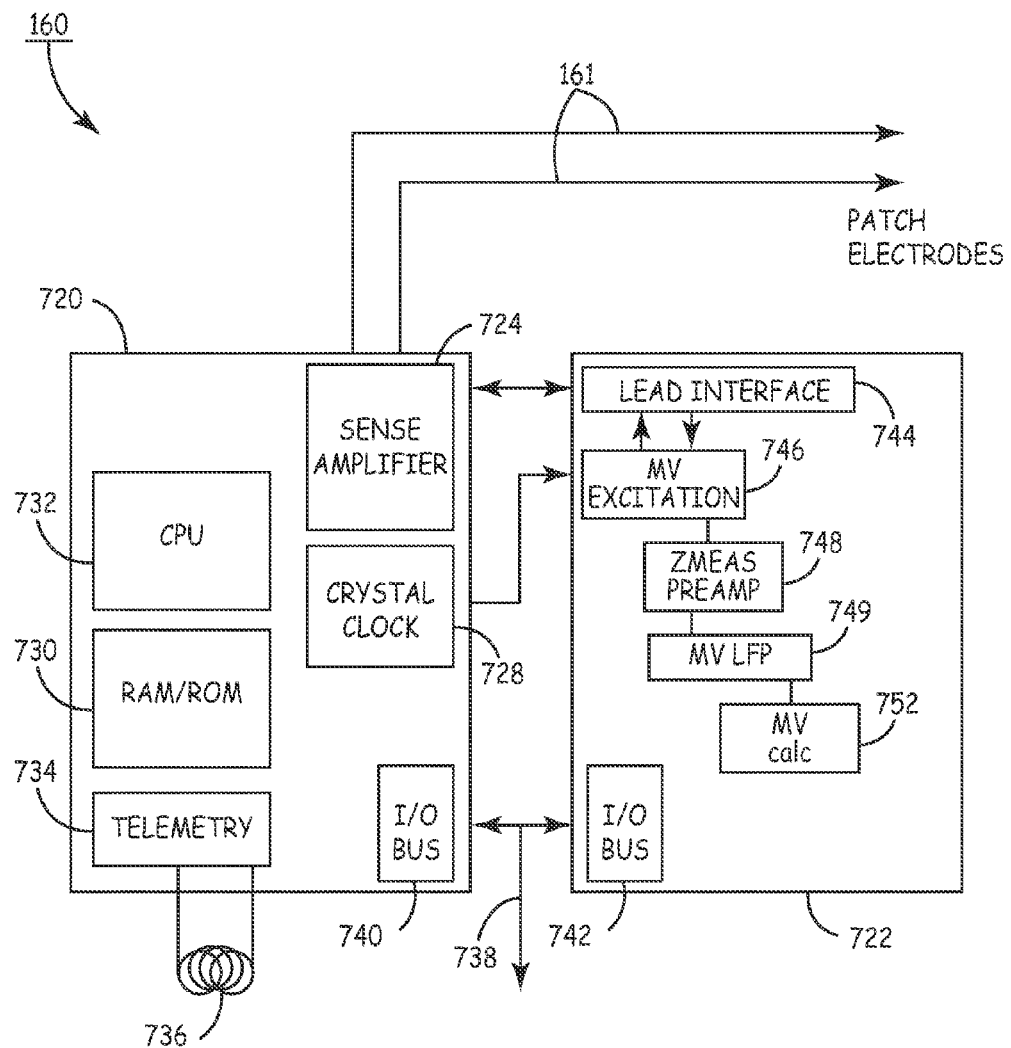

FIG. 30 is a simplified block diagram of a core monitor as shown in FIG. 4 above.

Figure 31:
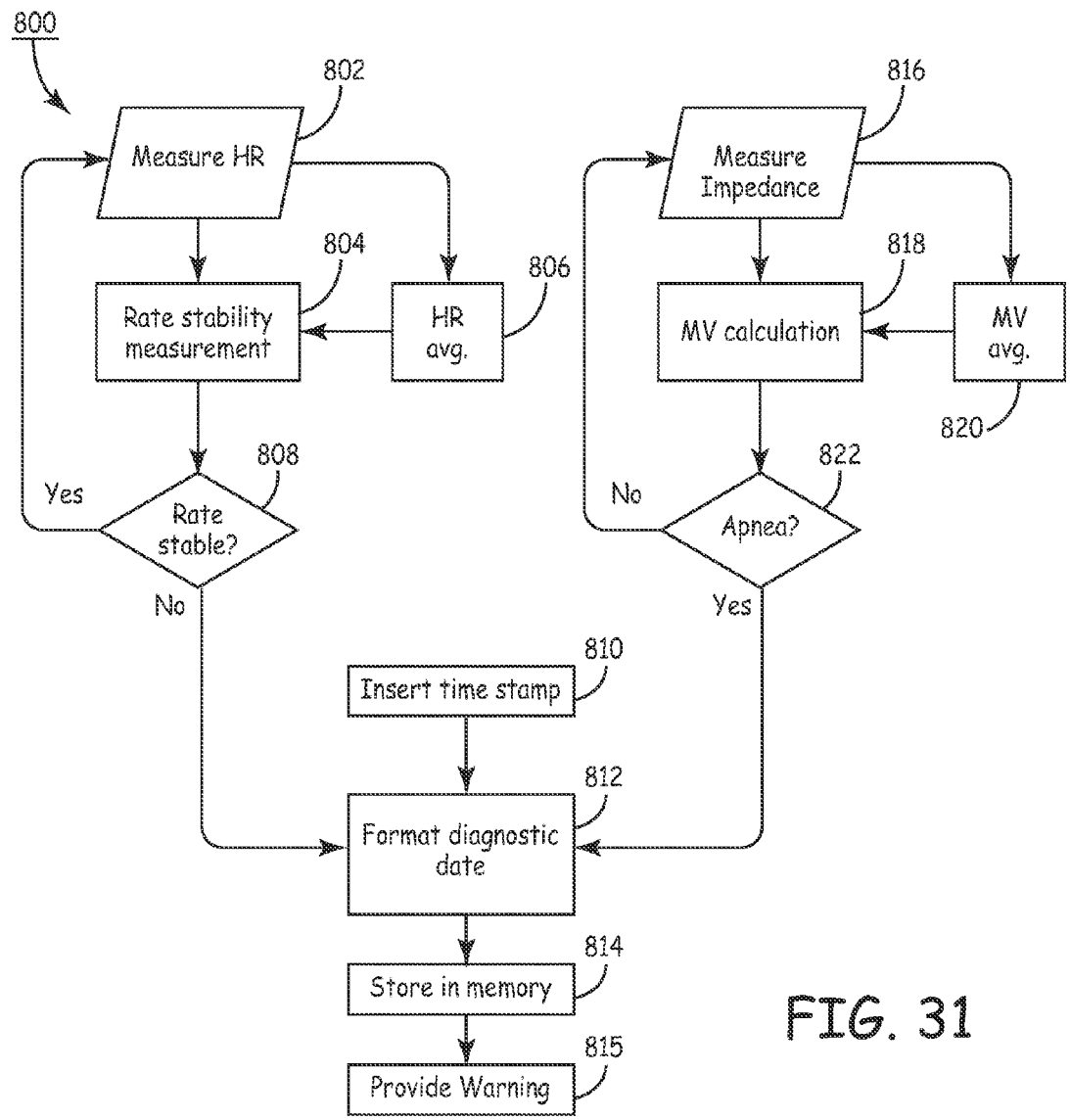

FIG. 31 is a flow diagram showing operation of a core monitor as shown in FIG. 1-4 above.

Figure 32:
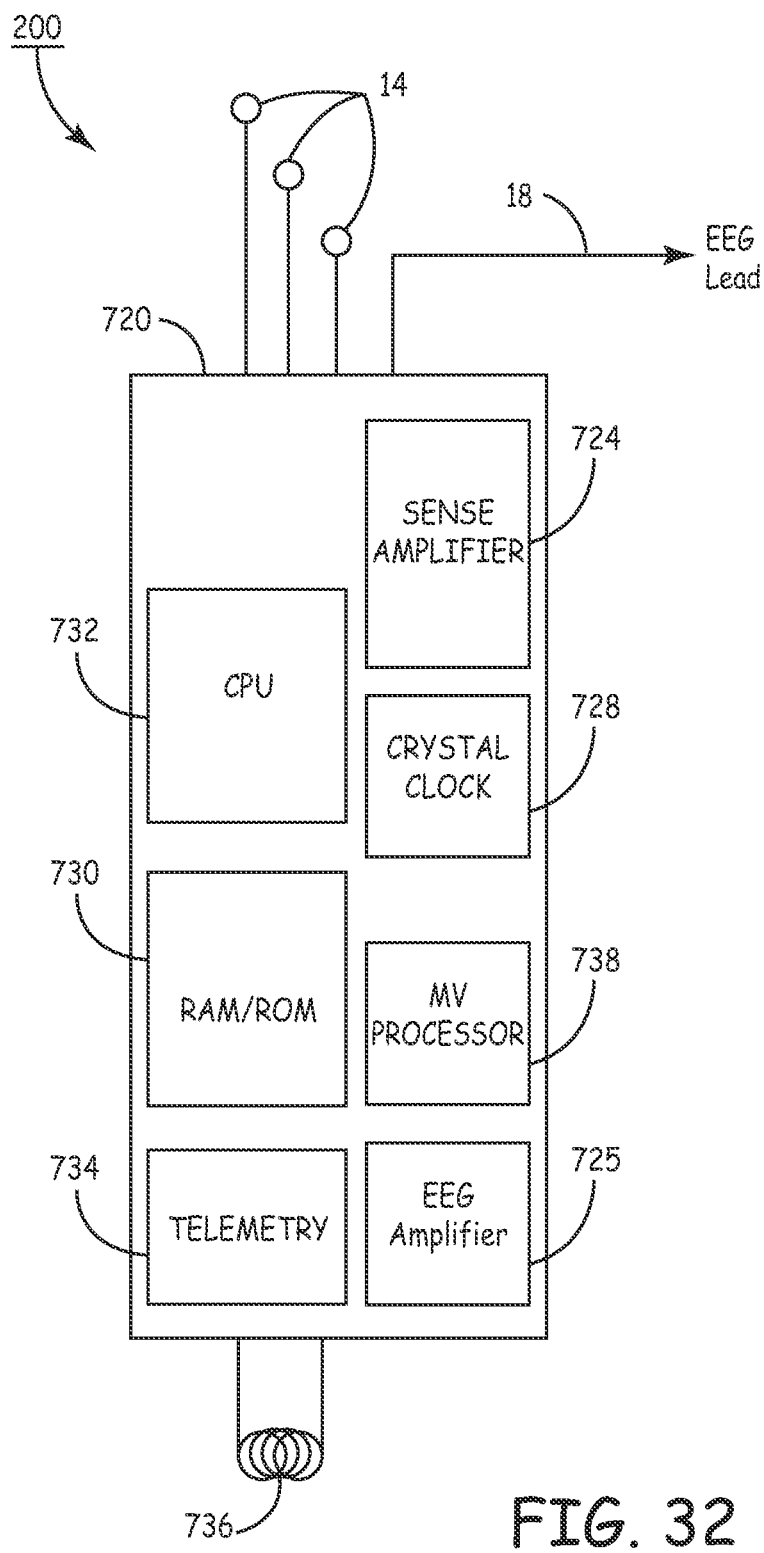

FIG. 32 is a simplified block diagram of a full monitor as shown in FIG. 5 above.

Figure 33:
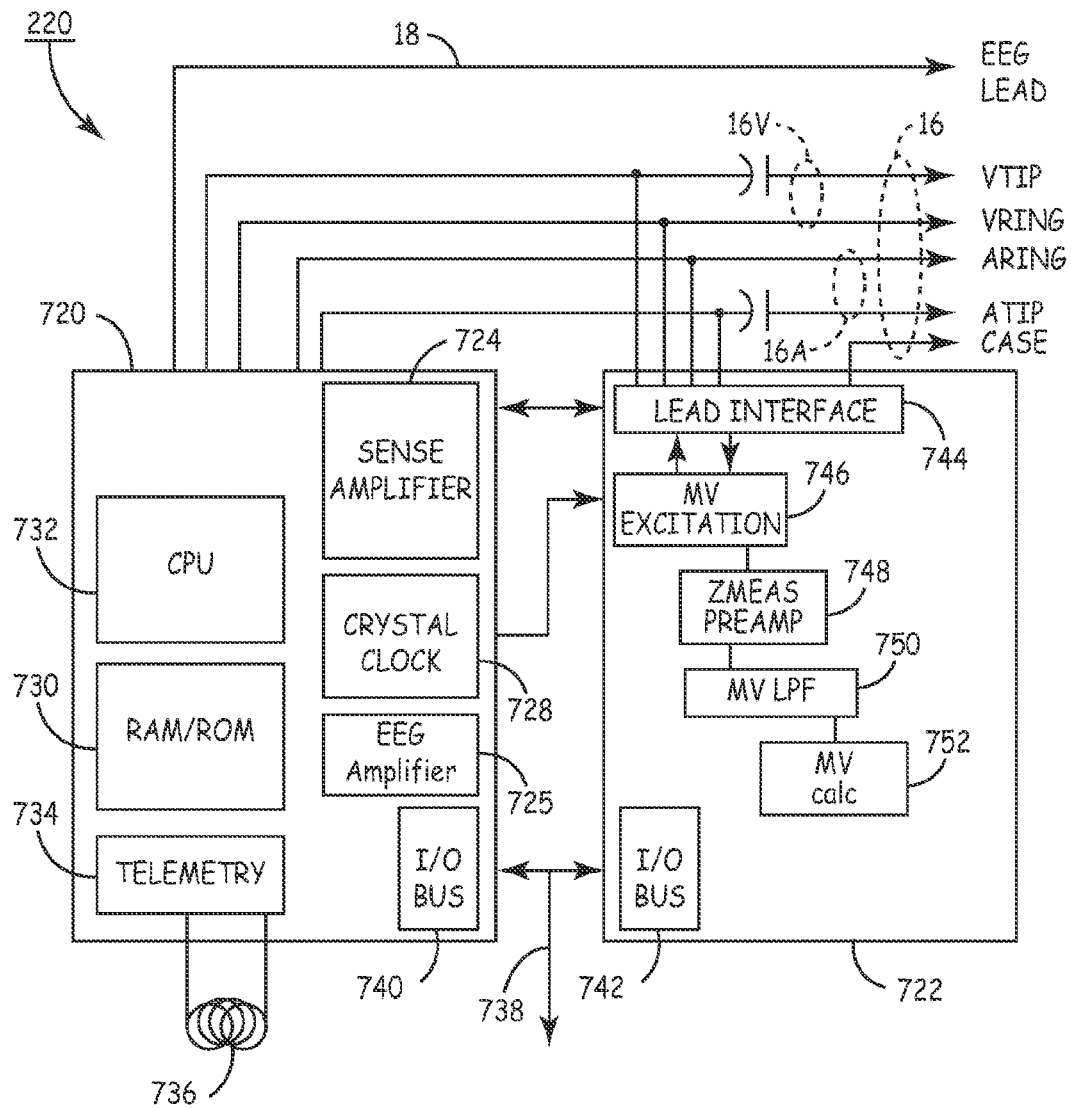

FIG. 33 is a simplified block diagram of a full monitor as shown in FIG. 6 above.

Figure 34:
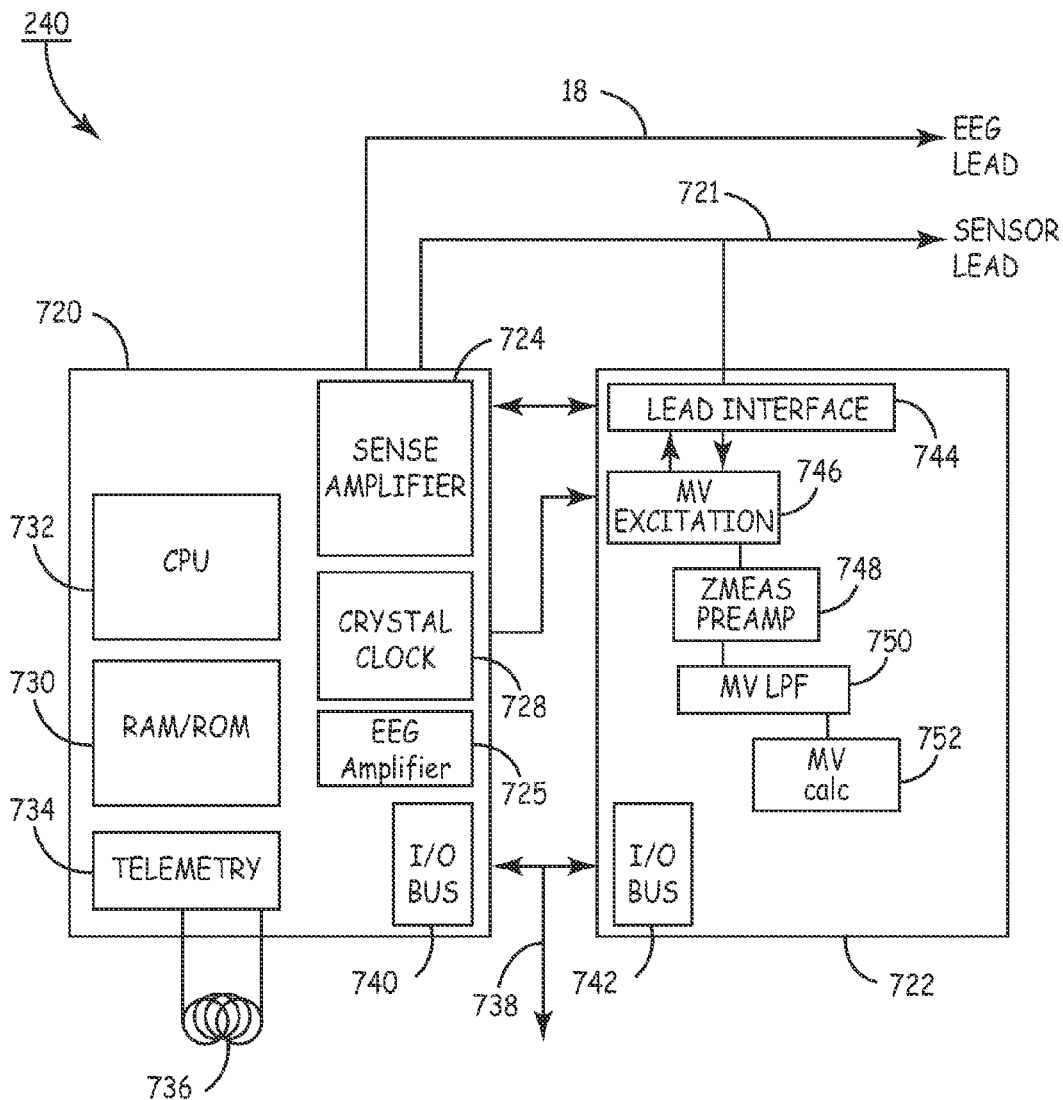

FIG. 34 is a simplified block diagram of a full monitor as shown in FIGS. 7 and 9 above.

Figure 35:
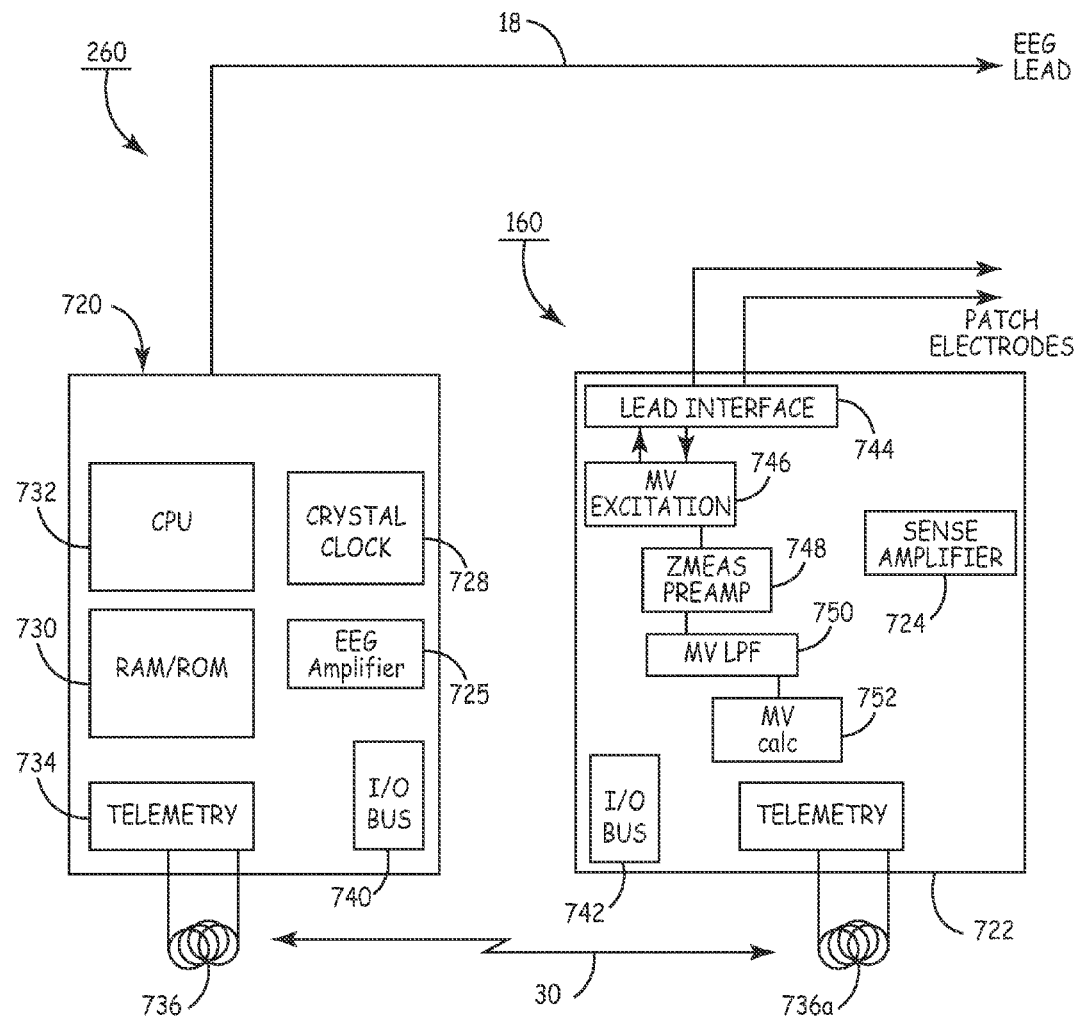

FIG. 35 is a simplified block diagram of a full monitor as shown in FIG. 8 above.

Figure 36:
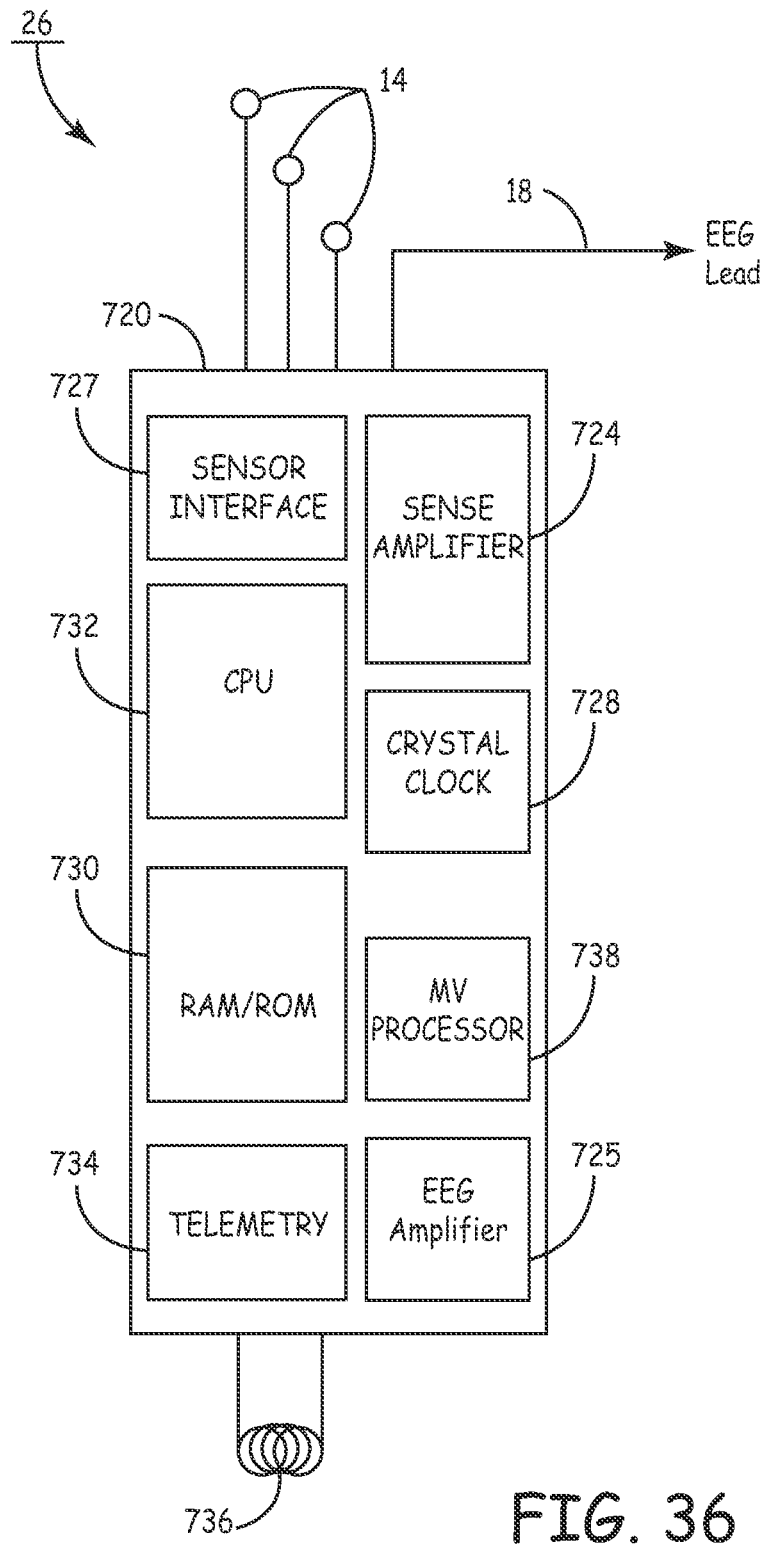

FIG. 36 is a simplified block diagram of a full monitor as shown in FIG. 10 above.

Figure 37:
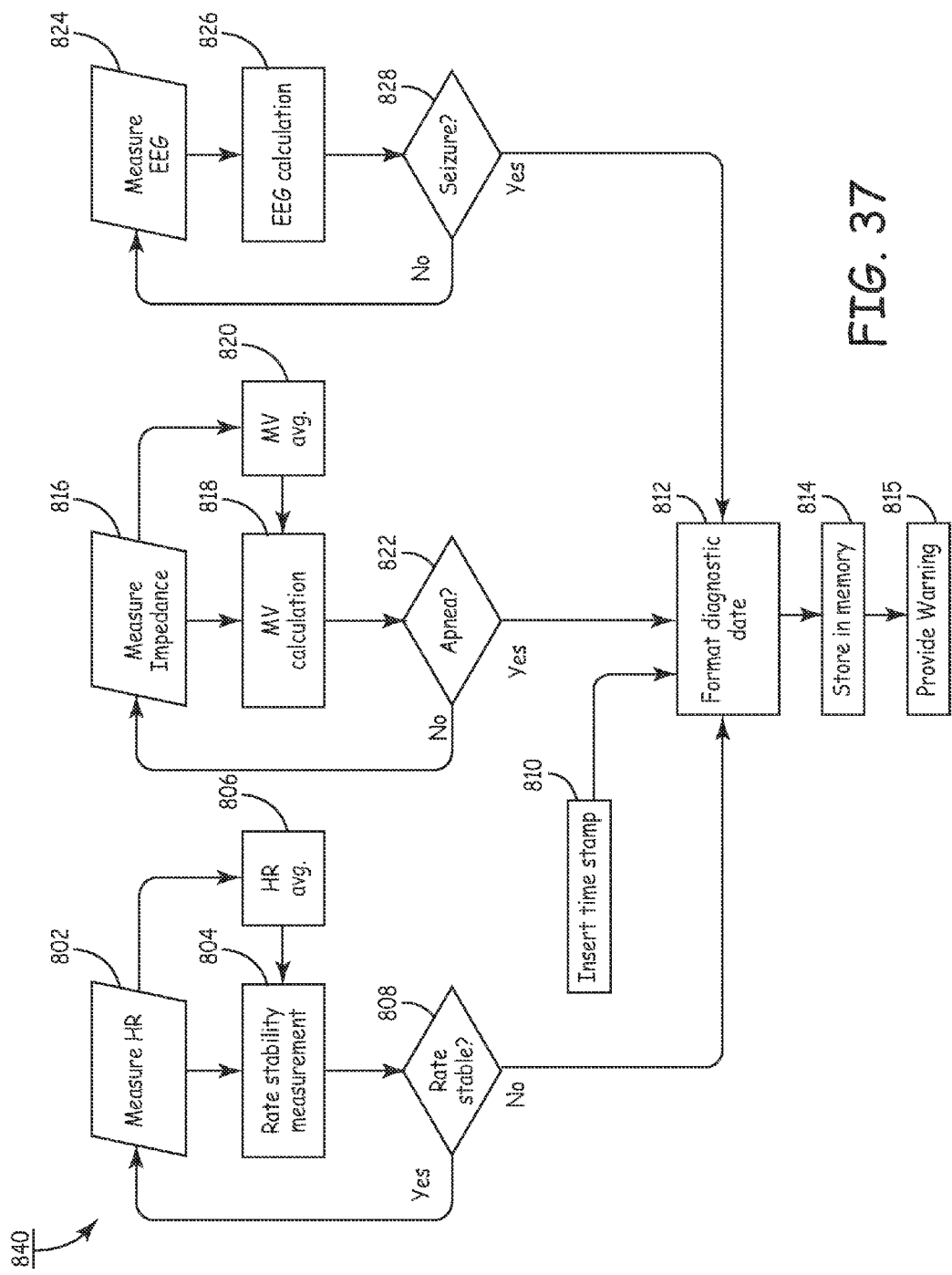

FIG. 37 is a flow diagram showing operation of a full monitor as shown in FIG. 5-10 above.

Figure 38:
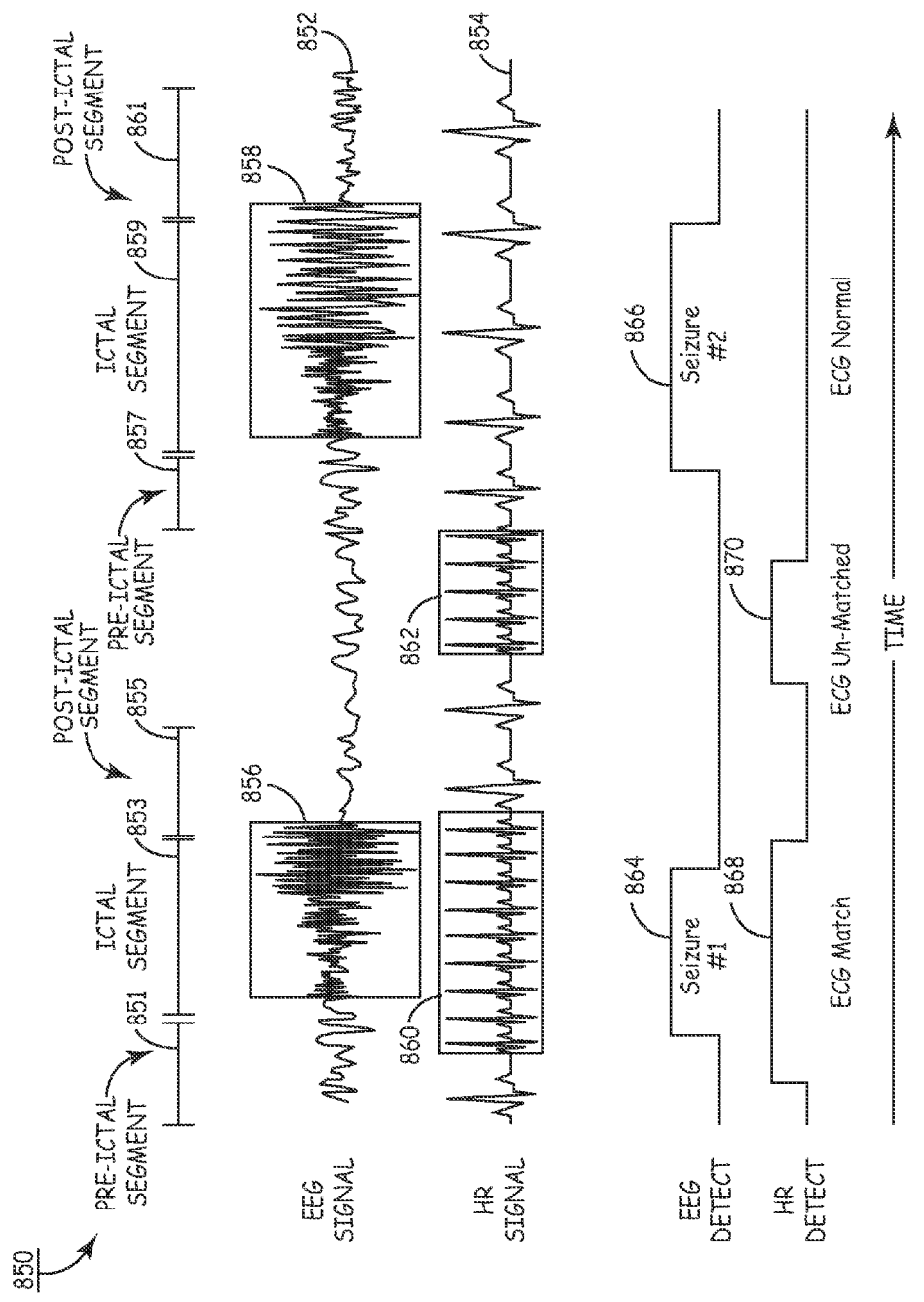

FIG. 38 is a diagram of exemplary physiologic data from a patient with a full monitor as shown in relation to FIG. 5-10 above.

Figure 39:
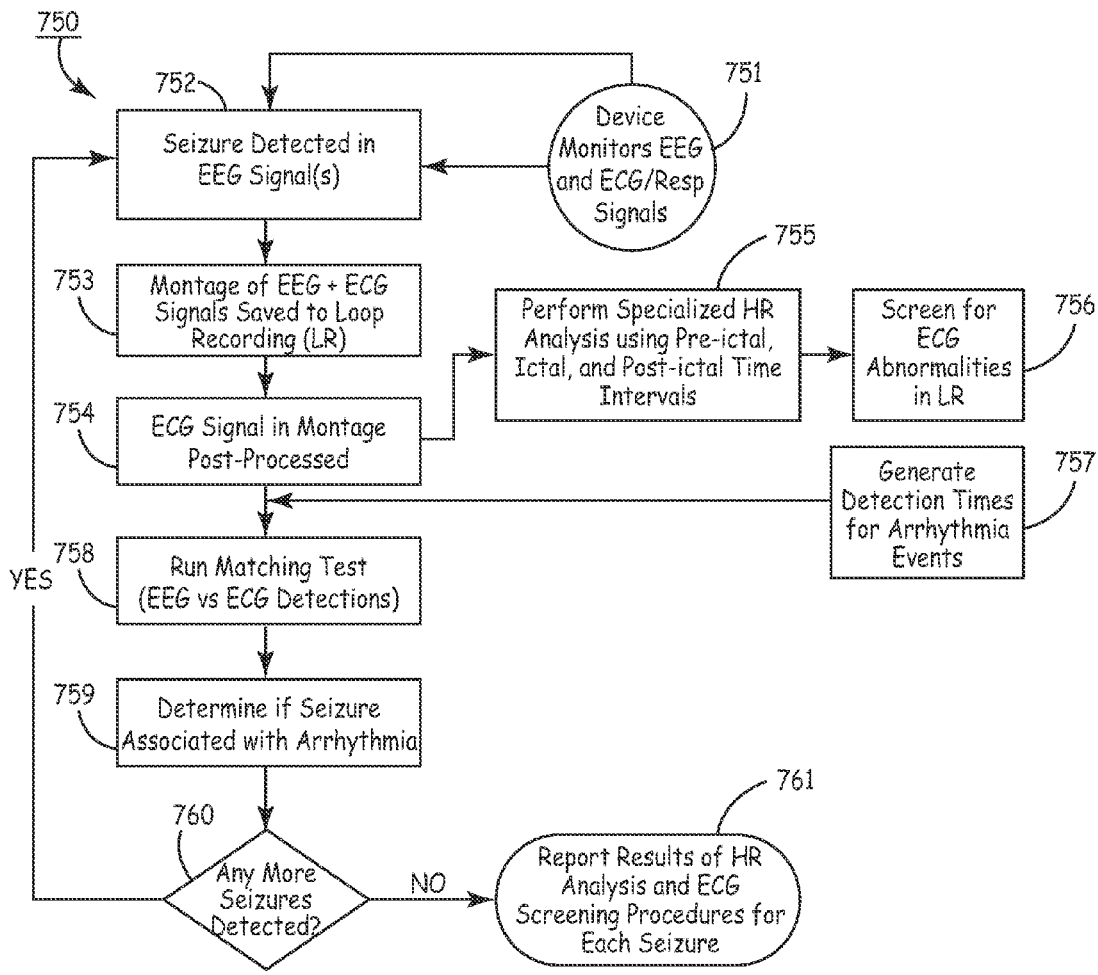

FIG. 39 shows a process for identifying ECG and respiratory abnormalities recorded during detected seizures in a full monitor as shown in relation to FIG. 5-10 above.

FIG. 40A shows a process for enabling the cardiac or respiratory detectors for neurological event detection in a full monitor as shown in relation to FIG. 5-10 above and detection/treatment as described in FIG. 41-51 below.

FIG. 40B shows a process for enabling the ECG or respiratory detectors for seizure detection in a full monitor as shown in relation to FIG. 5-10 above and detection/treatment as described in FIG. 41-51 below.

Figure 41:
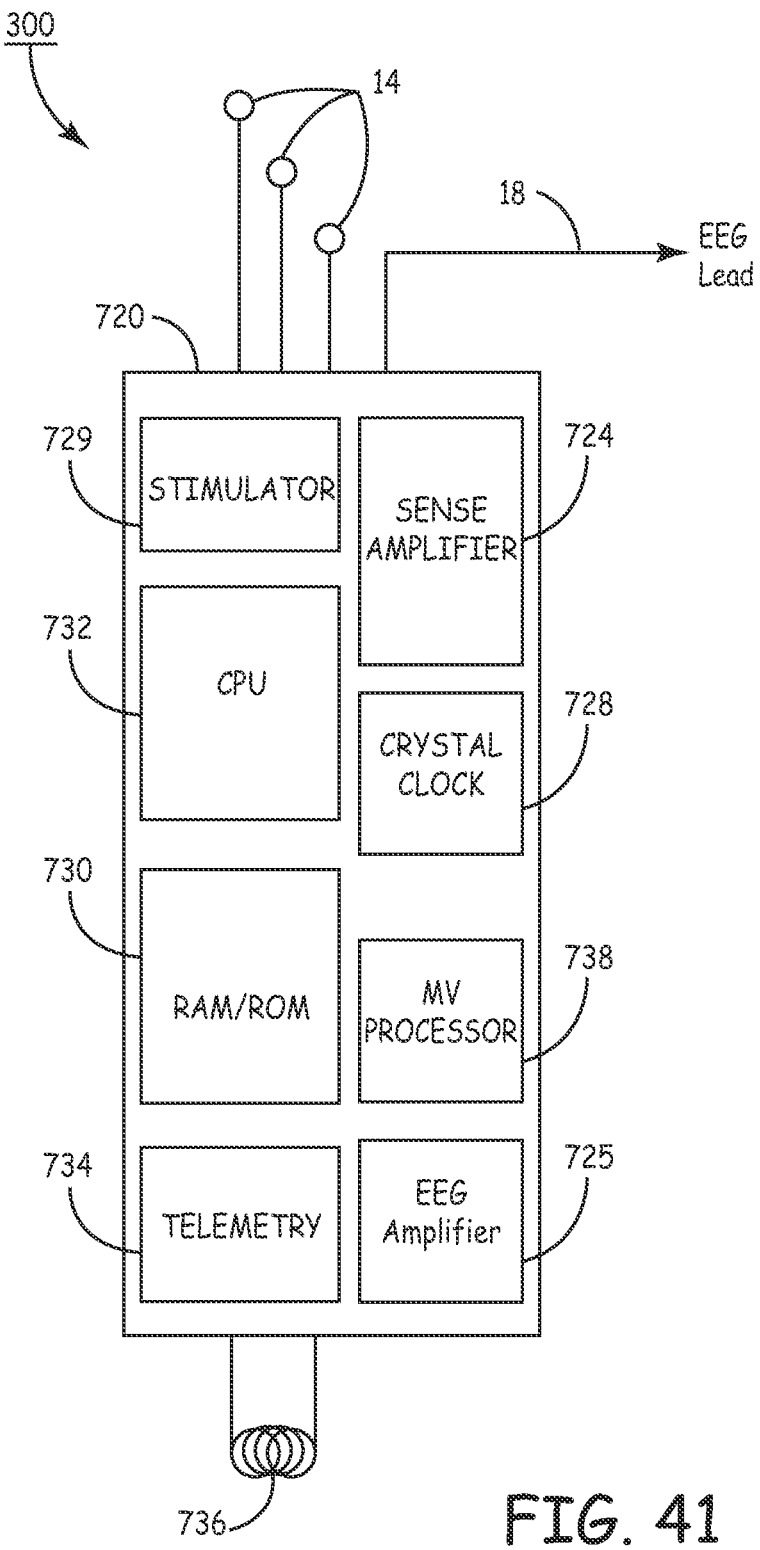

FIG. 41 is a simplified block diagram of a full monitor with brain stimulation therapy as shown in FIG. 11 above.

Figure 42:
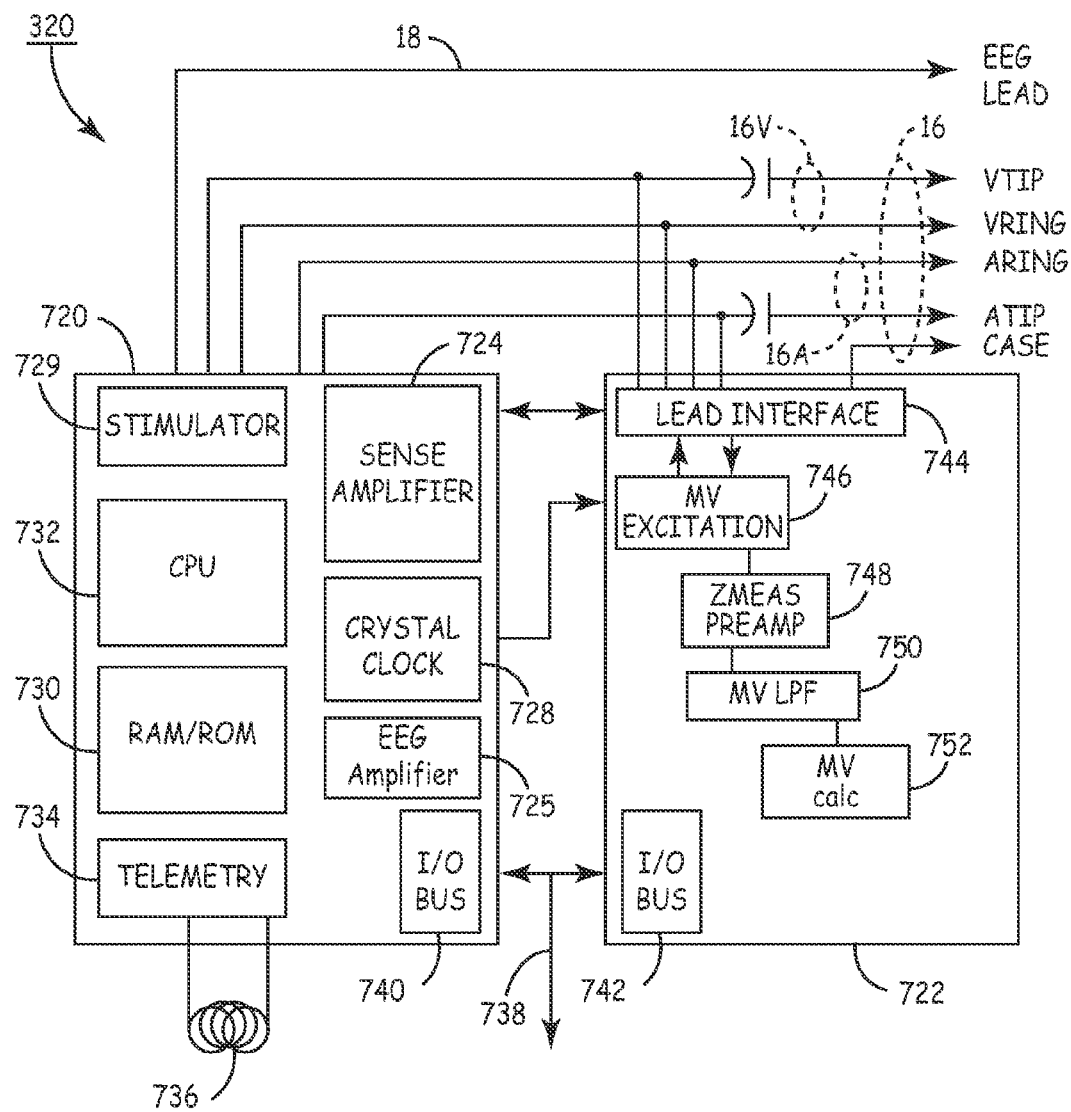

FIG. 42 is a simplified block diagram of a full monitor with brain stimulation therapy as shown in FIG. 12A above.

Figure 43:
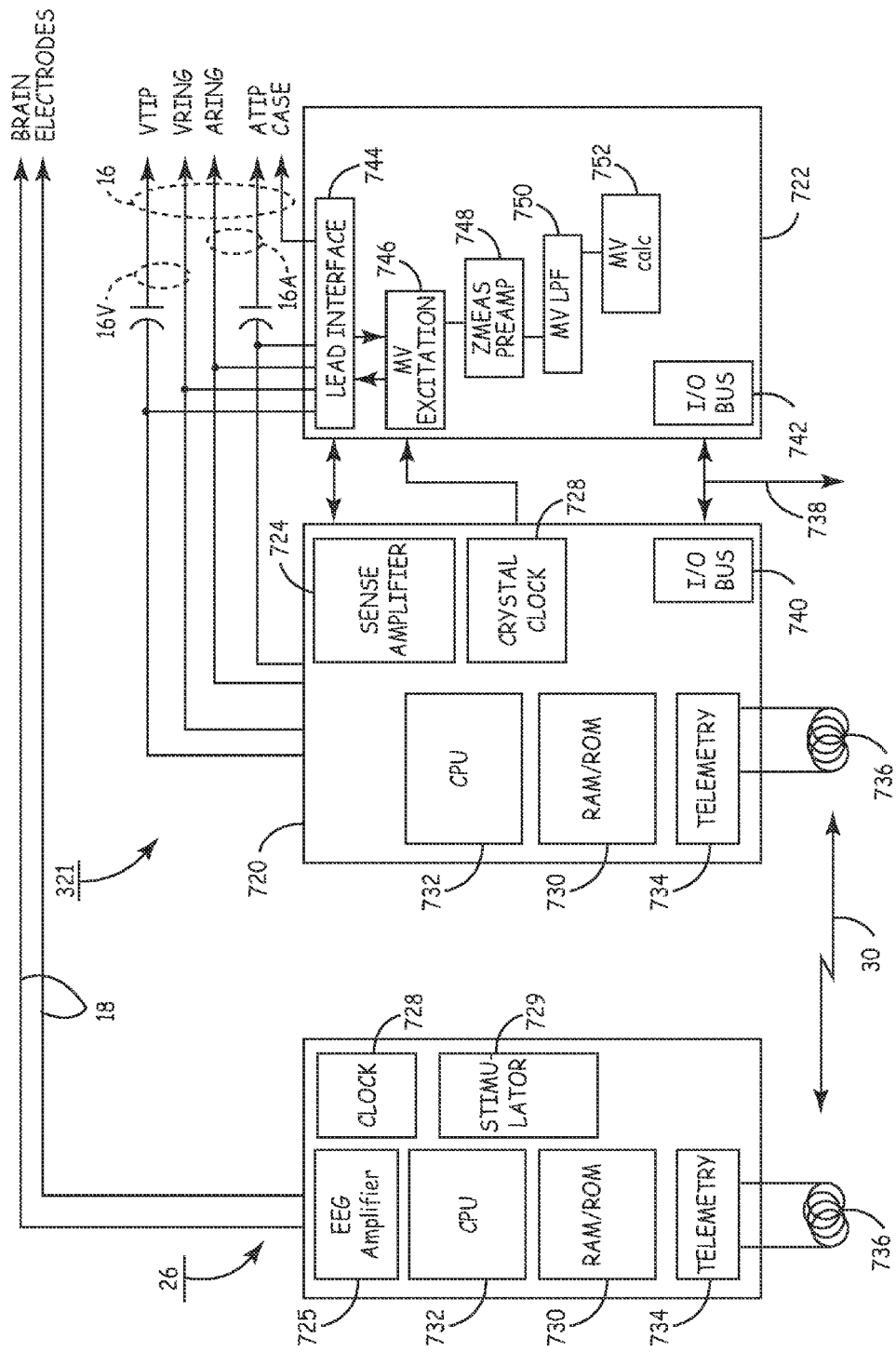

FIG. 43 is a simplified block diagram of a full monitor with brain stimulation therapy as shown in FIG. 12B above.

Figure 44:
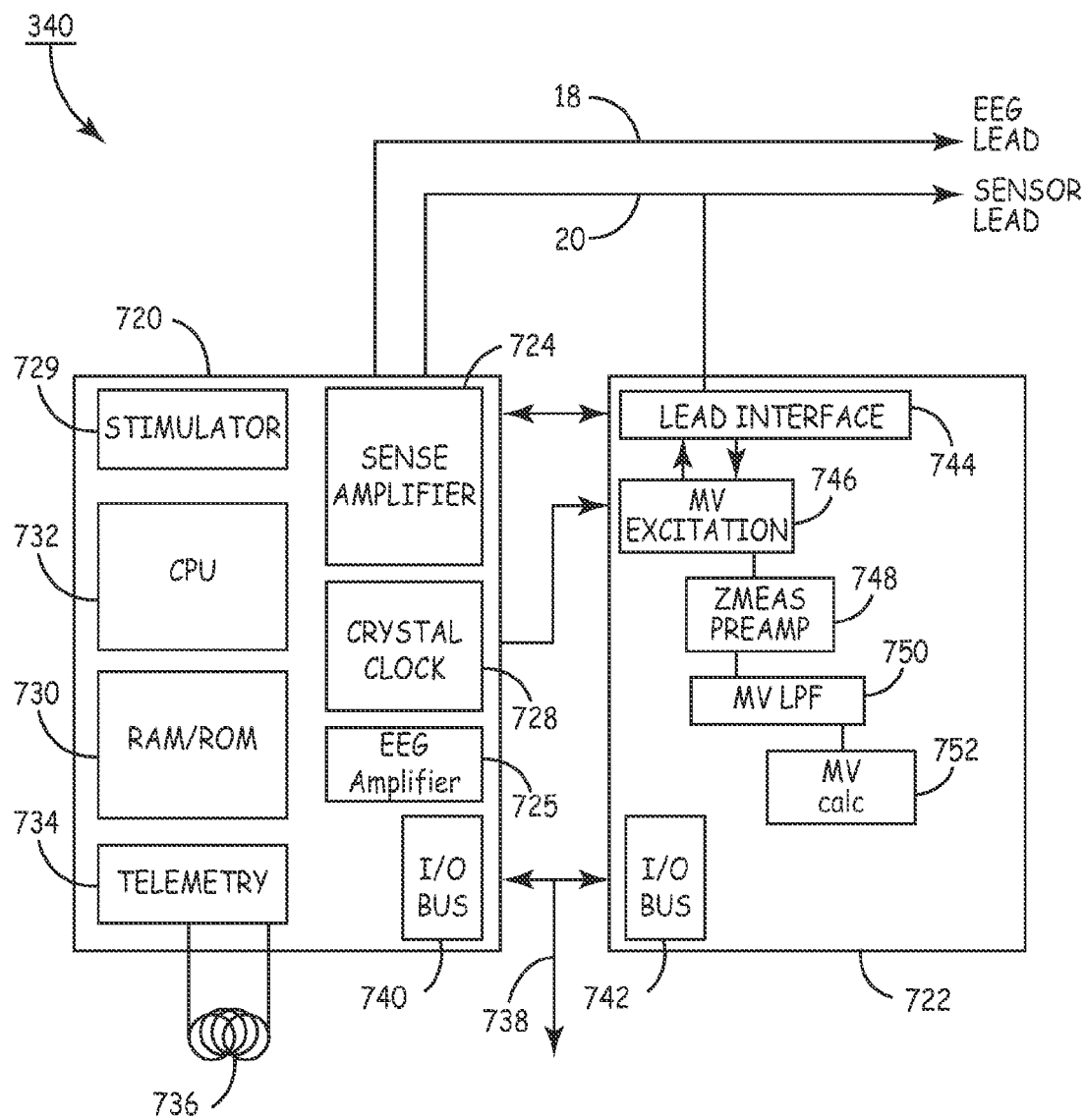

FIG. 44 is a simplified block diagram of a full monitor with brain stimulation therapy as shown in FIGS. 13 and 15 above.

Figure 45:
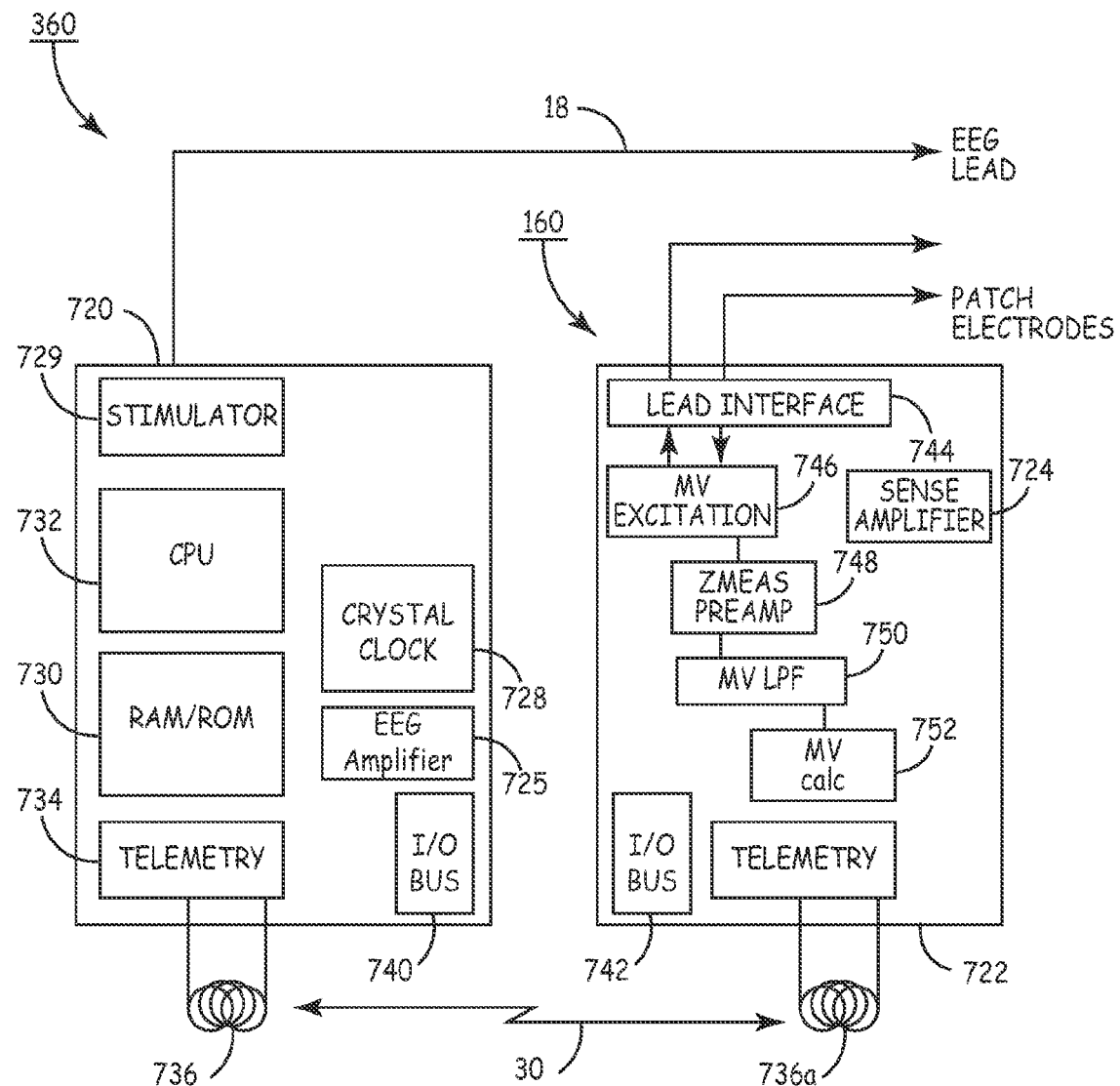

FIG. 45 is a simplified block diagram of a full monitor with brain stimulation therapy as shown in FIG. 14 above.

Figure 46:
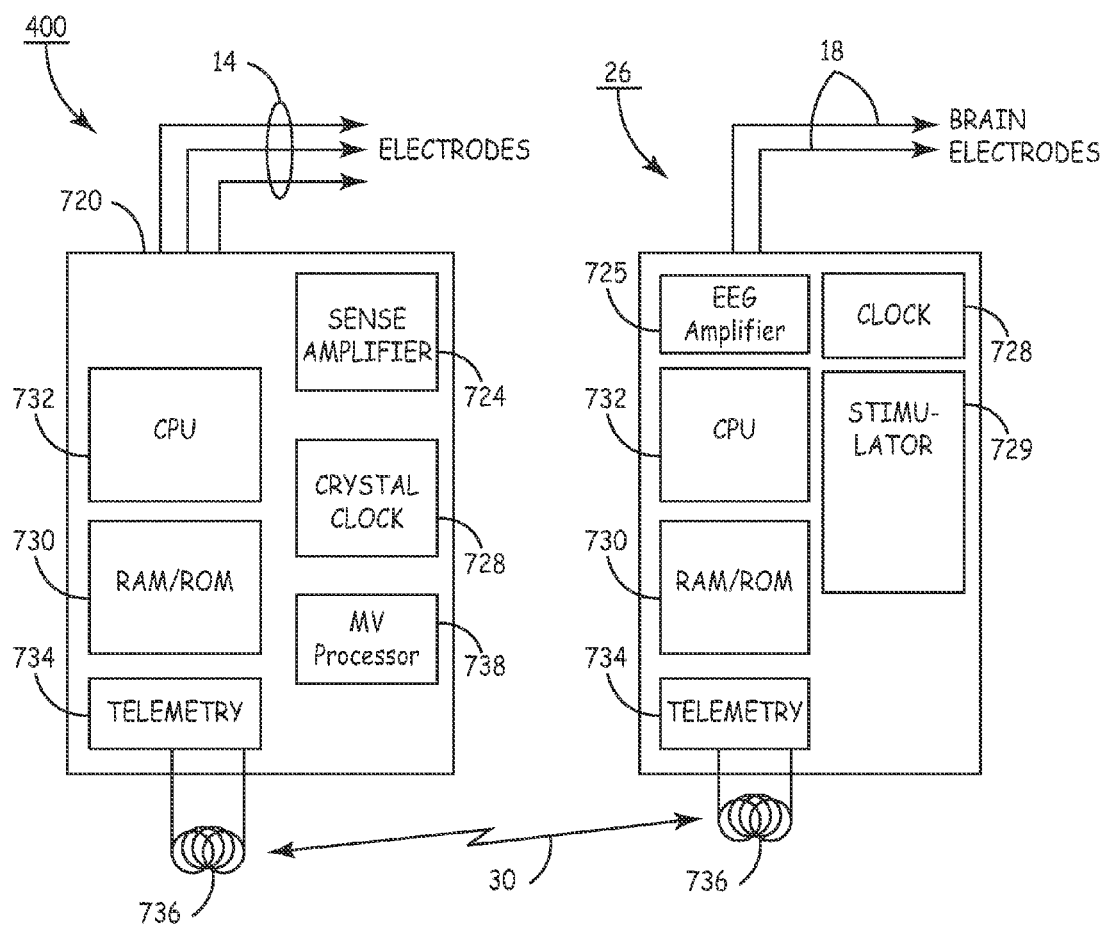

FIG. 46 is a simplified block diagram of a full monitor with brain stimulation therapy as shown in FIG. 20 above.

Figure 47:
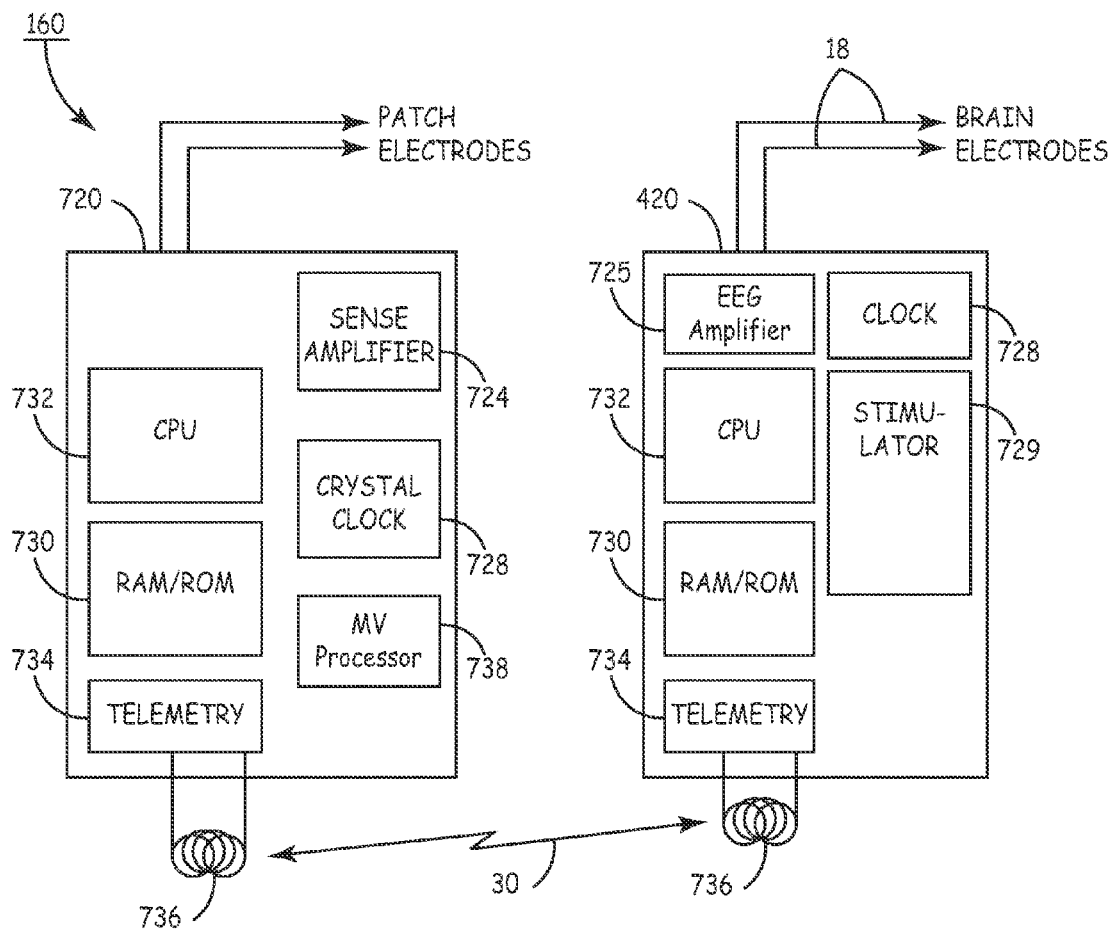

FIG. 47 is a simplified block diagram of a full monitor with brain stimulation therapy as shown in FIG. 21 above.

Figure 48:
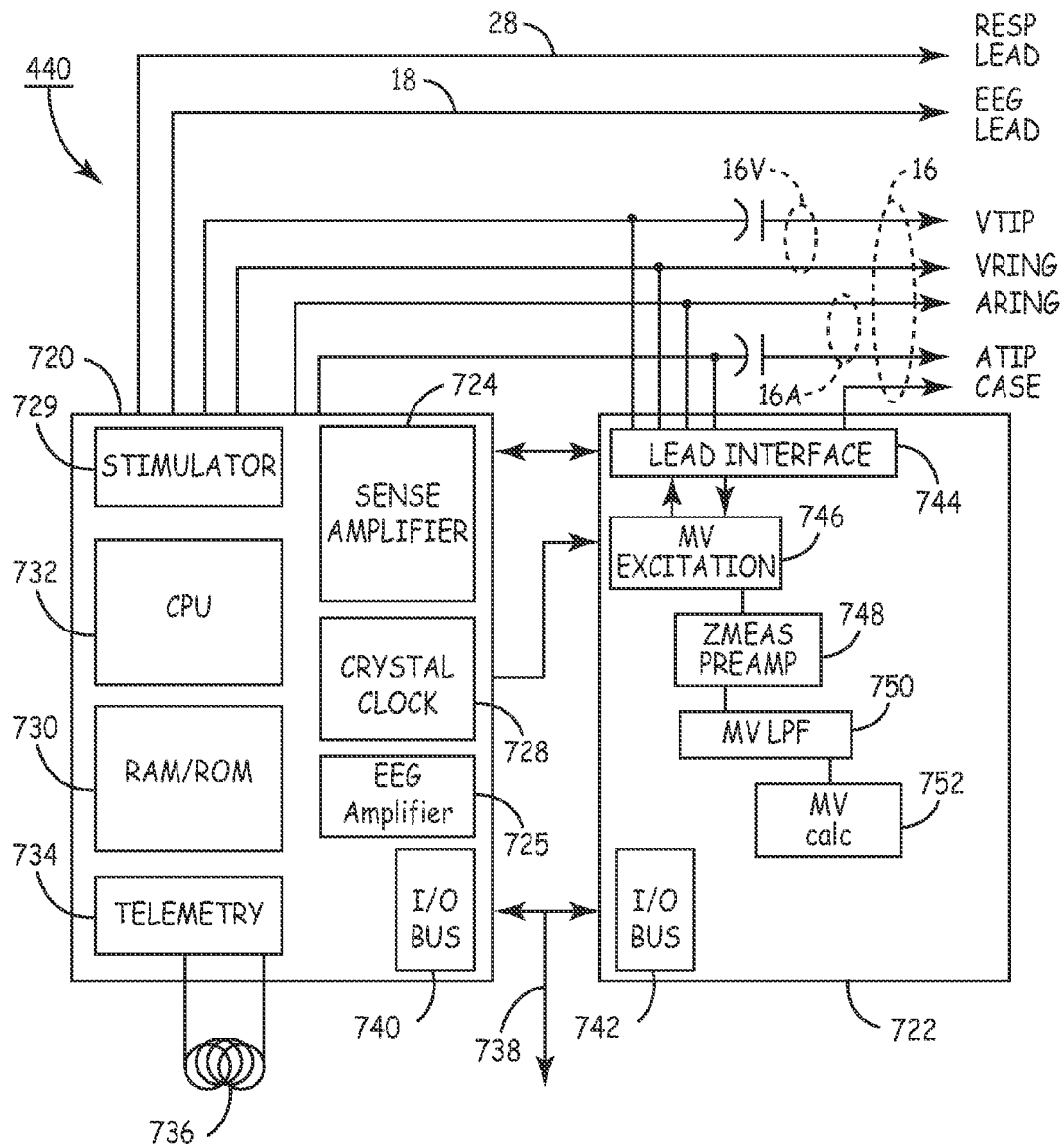

FIG. 48 is a simplified block diagram of a full monitor with brain and respiration stimulation therapy as shown in FIG. 16A above.

Figure 49:
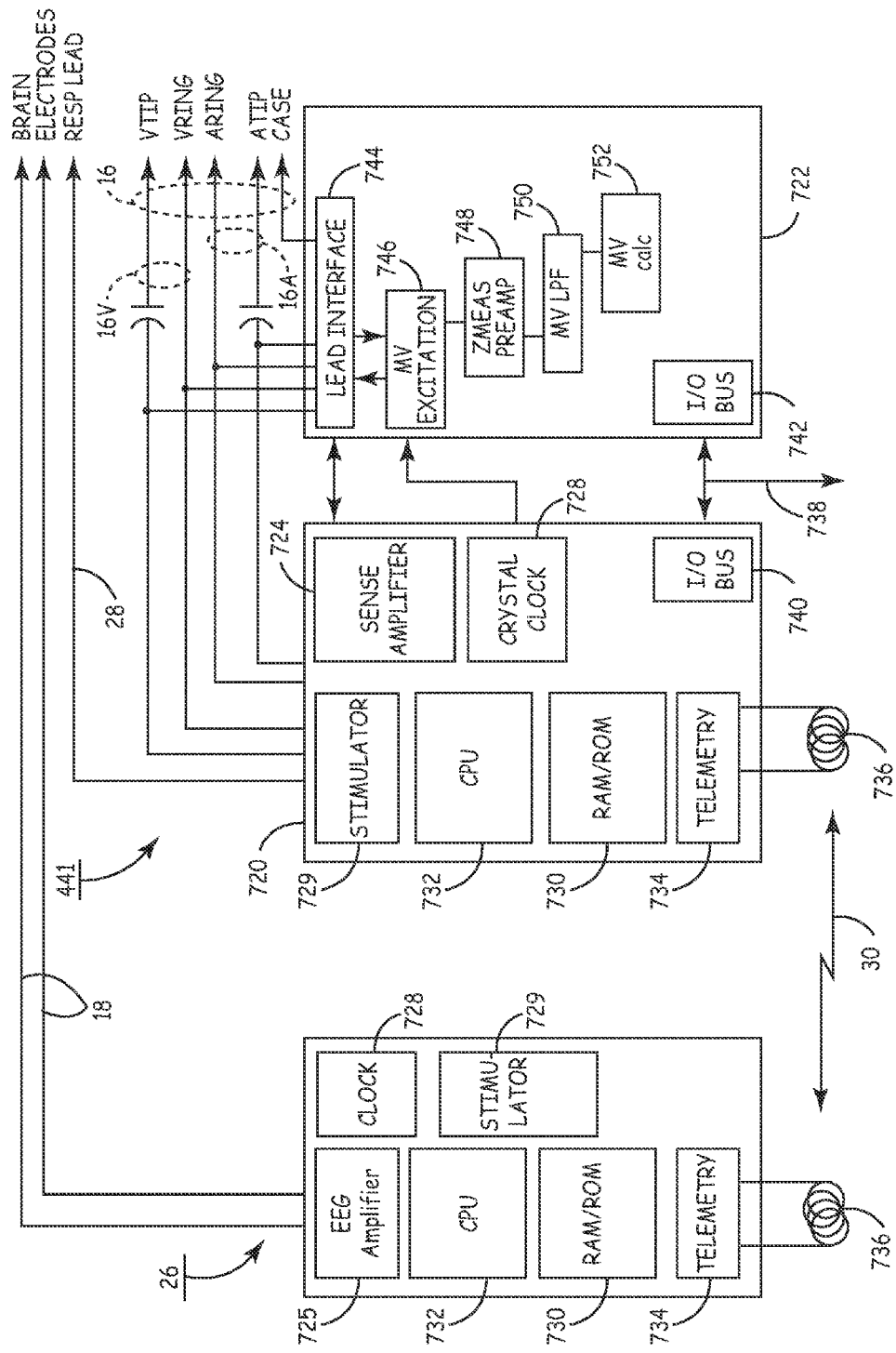

FIG. 49 is a simplified block diagram of a full monitor with brain and respiration stimulation therapy as shown in FIG. 16B above.

Figure 50:
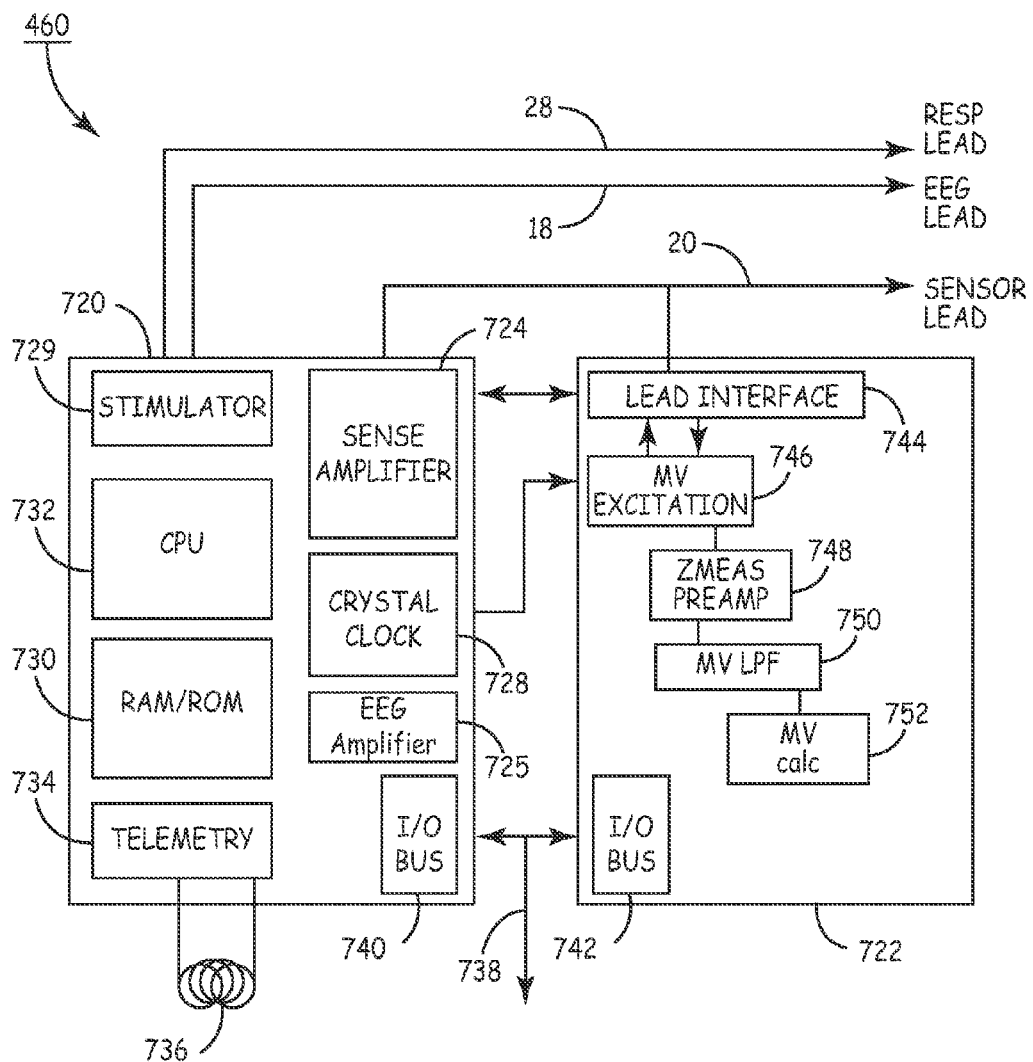

FIG. 50 is a simplified block diagram of a full monitor with brain and respiration stimulation therapy as shown in FIGS. 17, 18 and 19 above.

Figure 51:
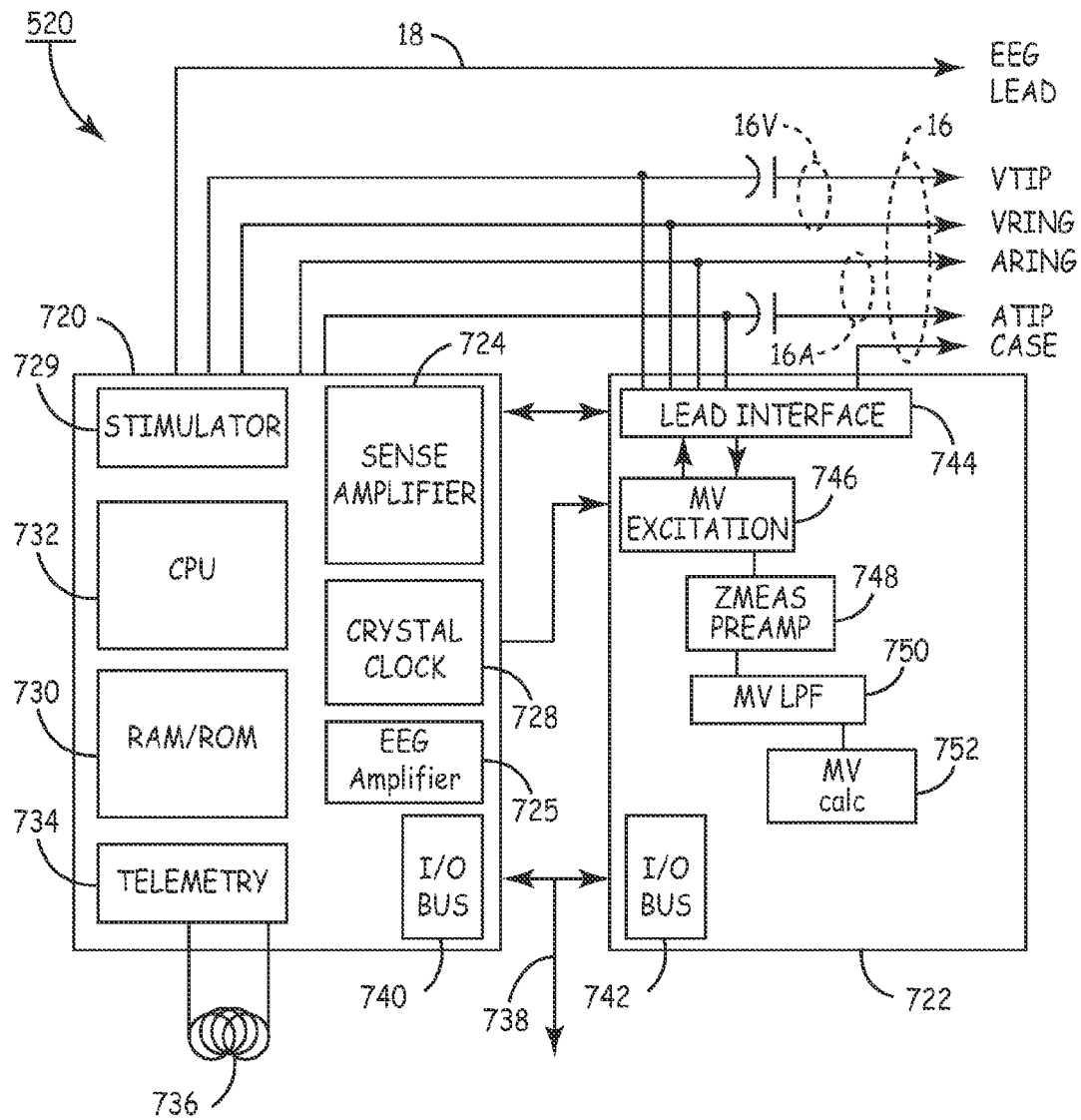

FIG. 51 is a simplified block diagram of a full monitor with brain and cardiac stimulation therapy as shown in FIG. 24A above.

Figure 52:
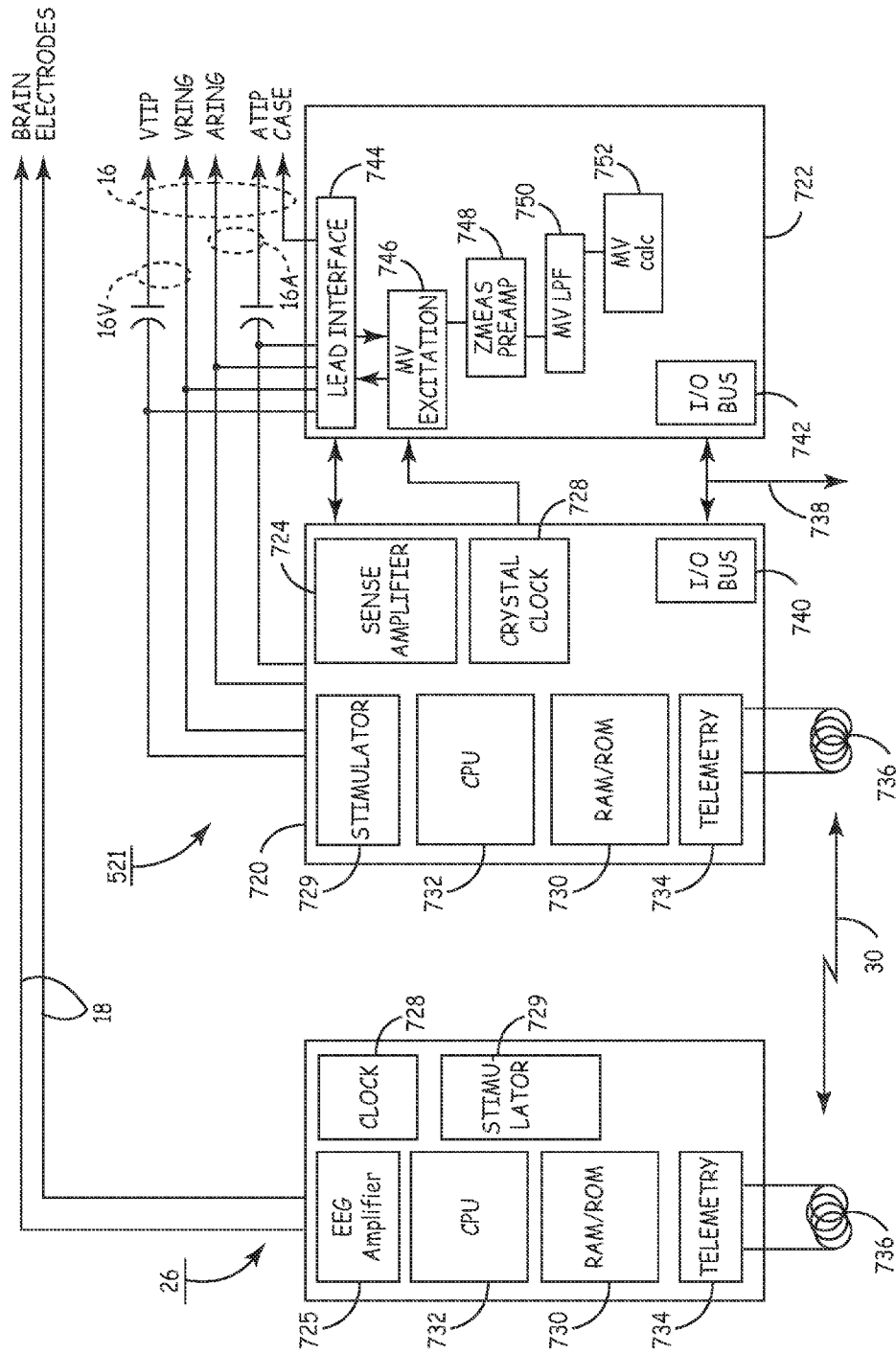

FIG. 52 is a simplified block diagram of a full monitor with brain and cardiac stimulation therapy as shown in FIG. 24B above.

Figure 53:
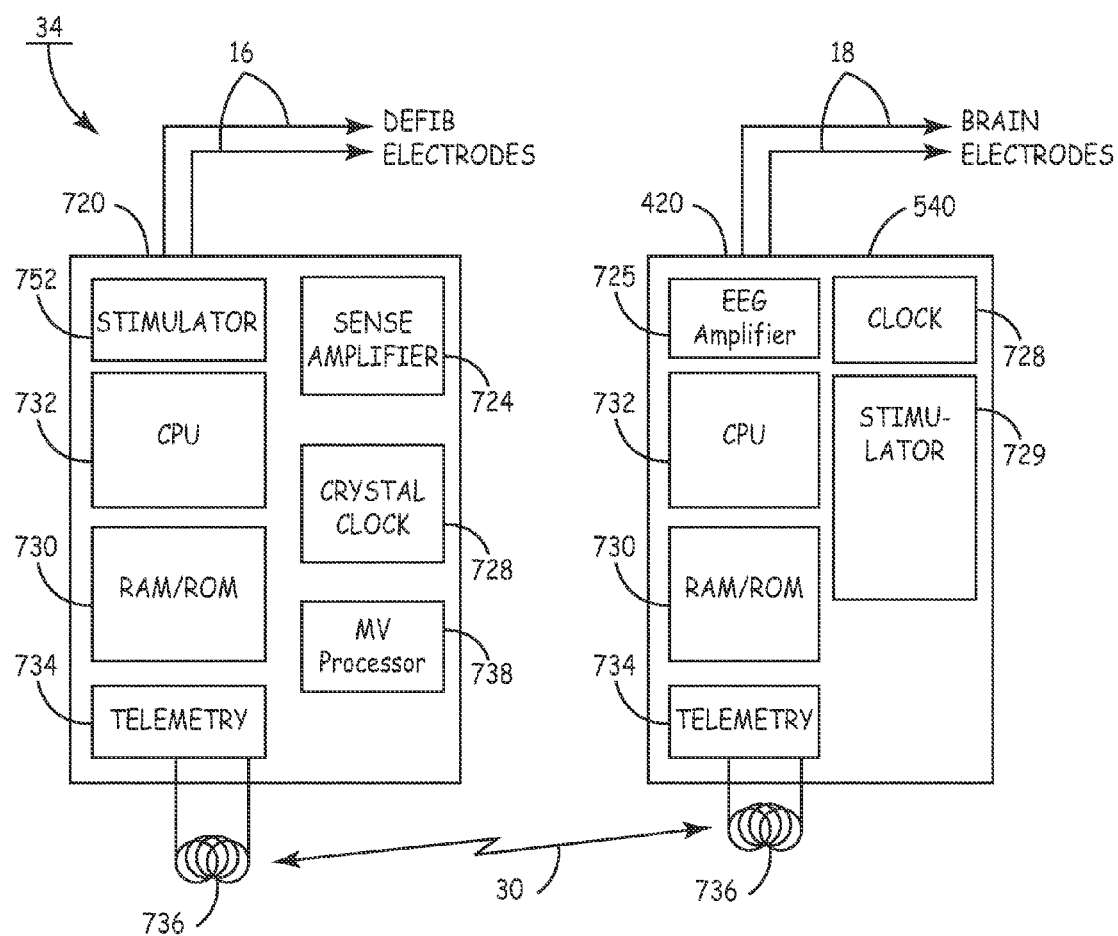

FIG. 53 is a simplified block diagram of a full monitor with brain and cardiac stimulation therapy as shown in FIGS. 22 and 23 above.

Figure 54:
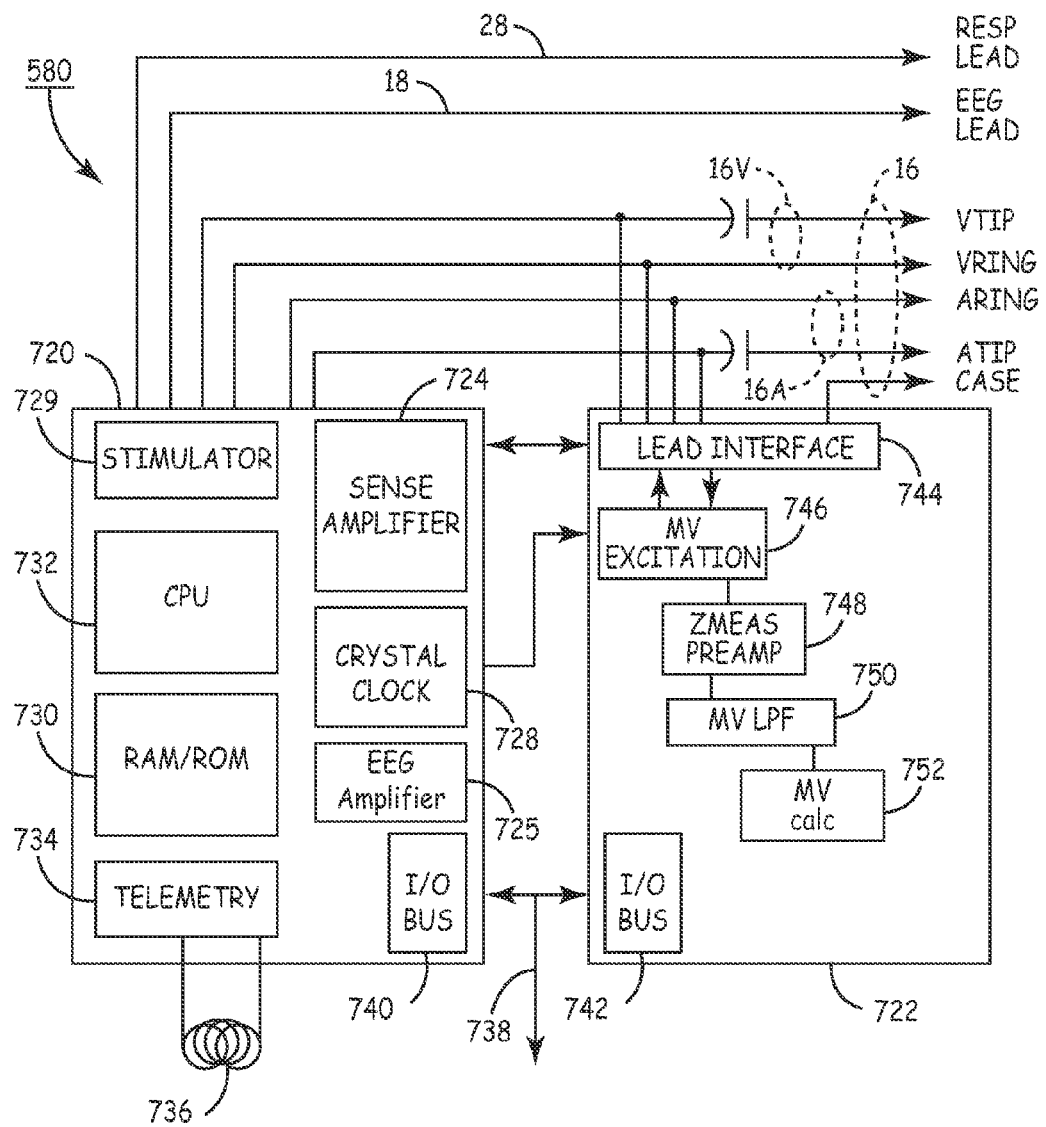

FIG. 54 is a simplified block diagram of a full monitor with brain, respiration and cardiac stimulation therapy as shown in FIG. 25A above.

Figure 55:
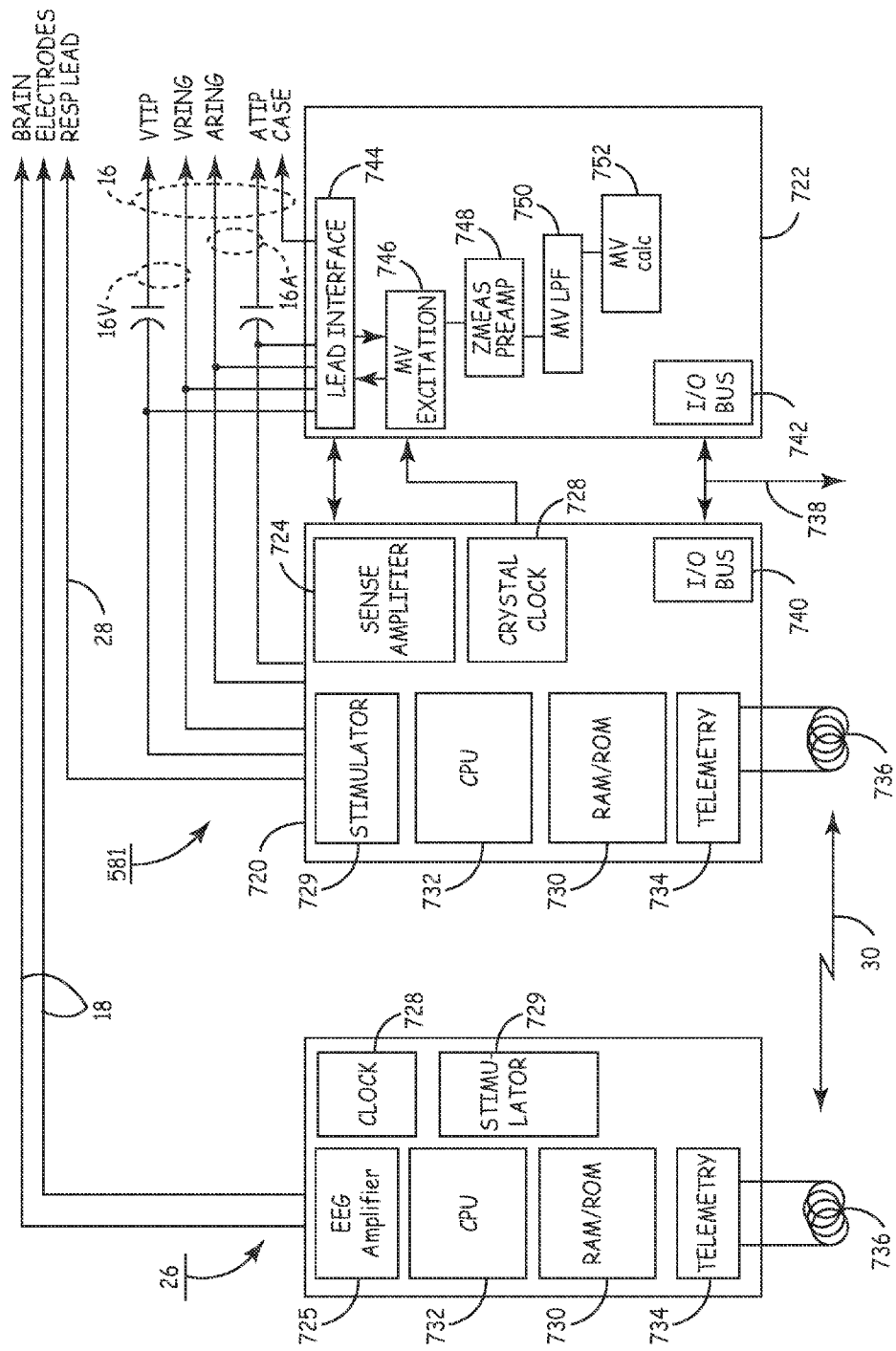

FIG. 55 is a simplified block diagram of a full monitor with brain, respiration and cardiac stimulation therapy as shown in FIG. 25B above.

Figure 56:
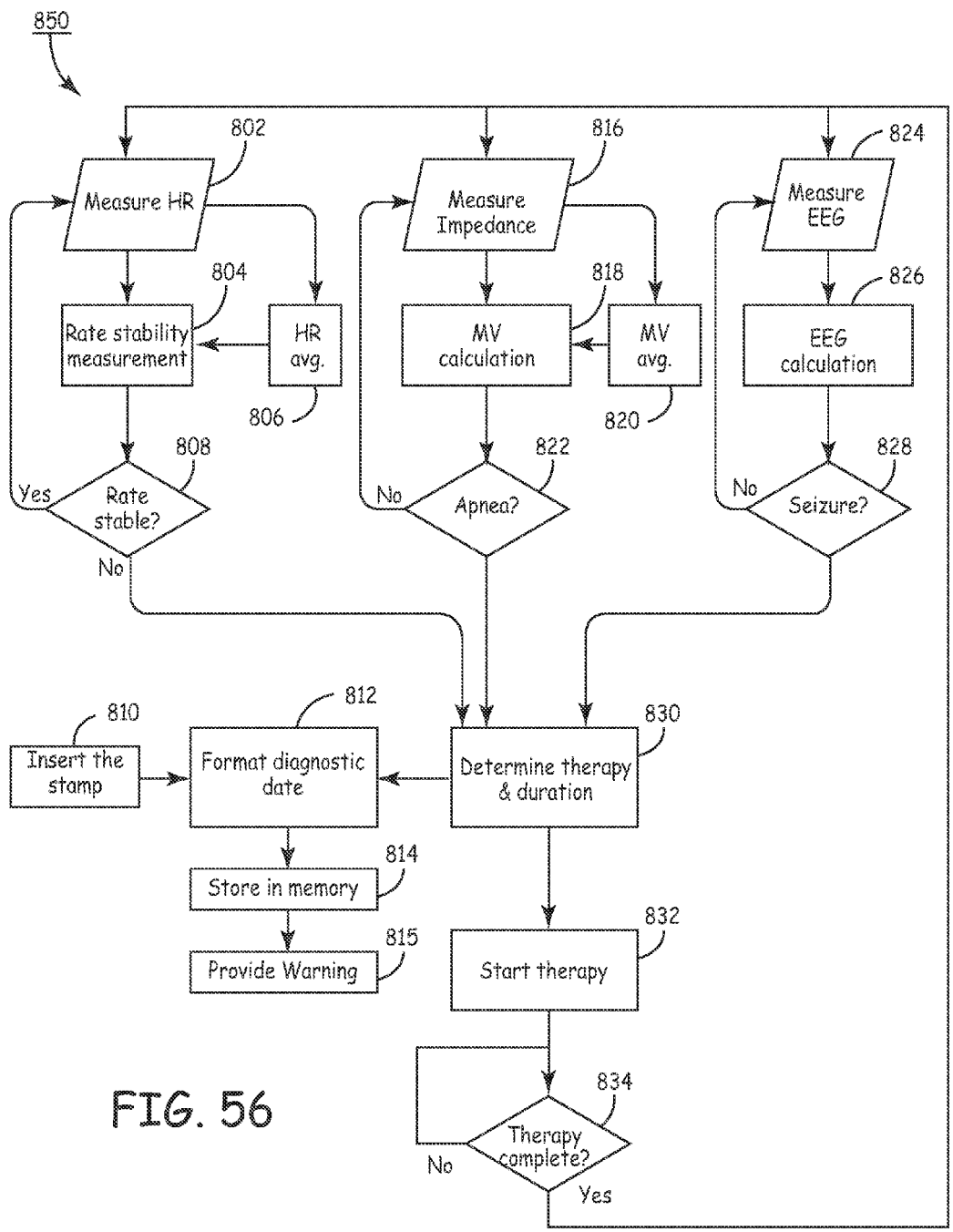

FIG. 56 is a flow diagram showing operation of a full monitor with therapy (including brain, respiration or cardiac stimulation therapy) as shown in FIG. 11-25 above.

Figure 57A:
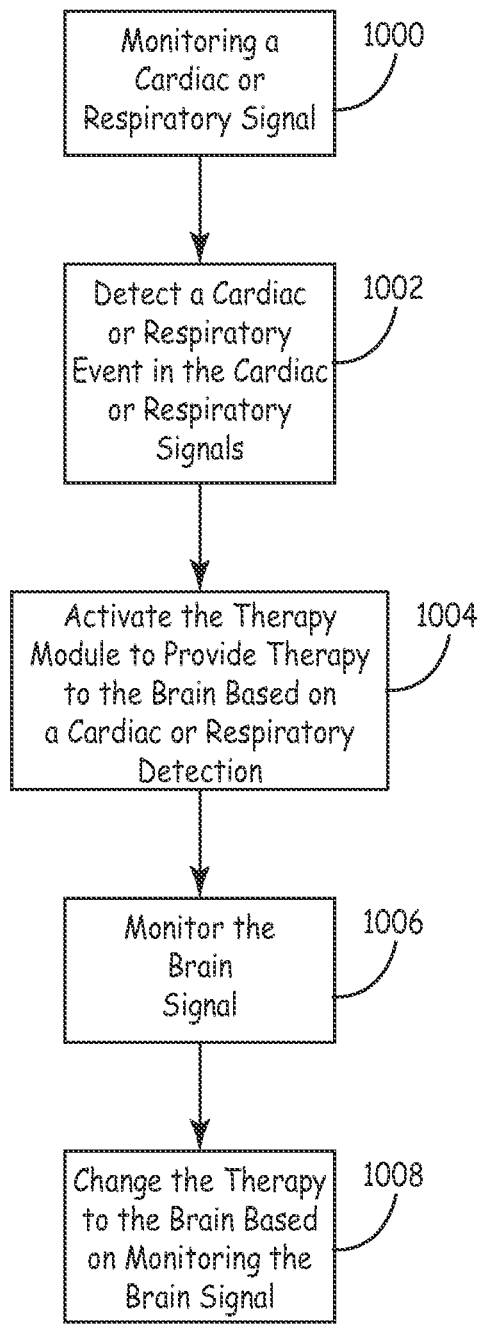

FIG. 57A is a flow diagram showing a process for enabling cardiac/respiratory detectors for neurological event detection and treatment including termination rules.

Figure 57B:
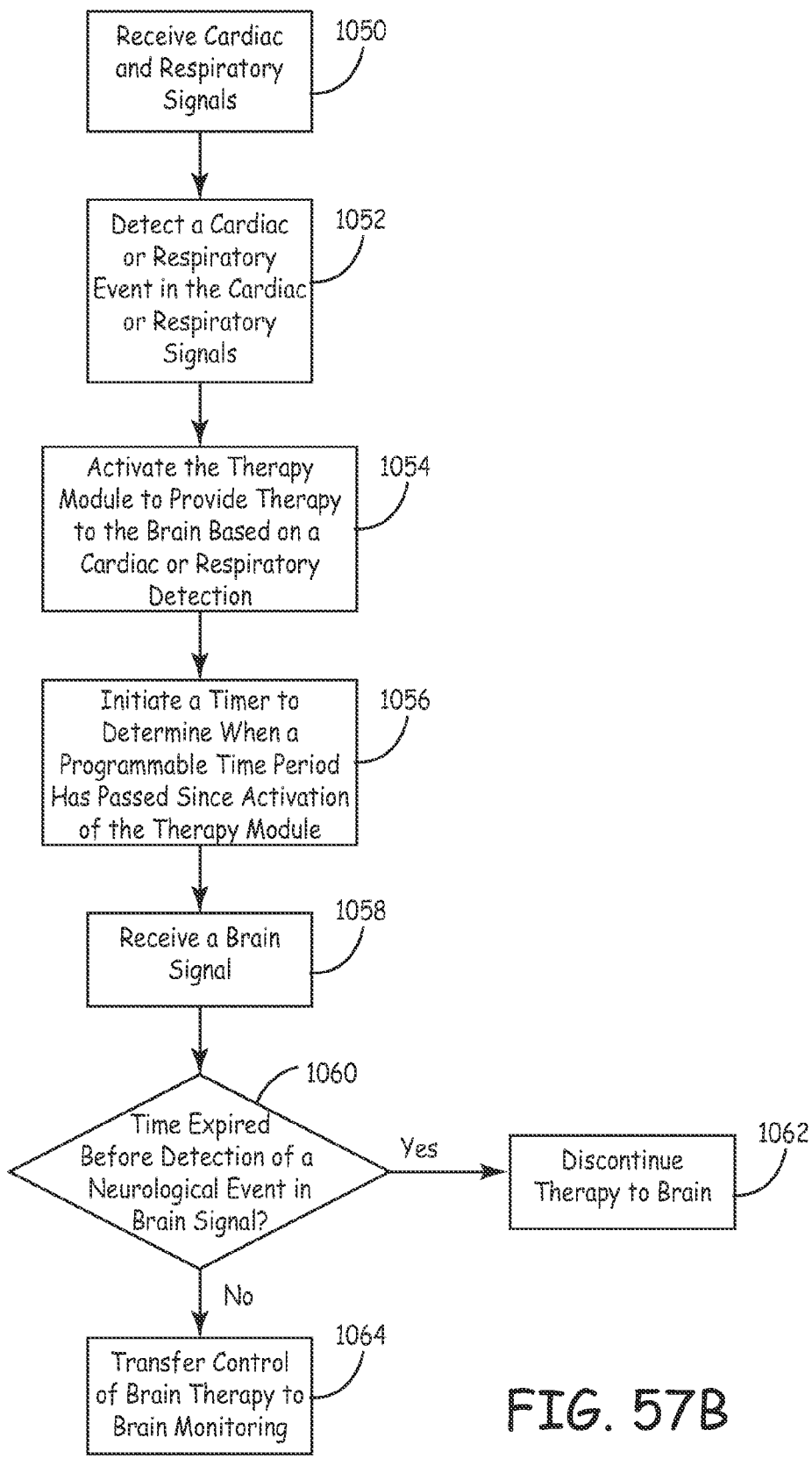

FIG. 57B is a flow diagram showing a process for enabling ECG/respiratory detectors for seizure detection and treatment including termination rules.

Figure 58:
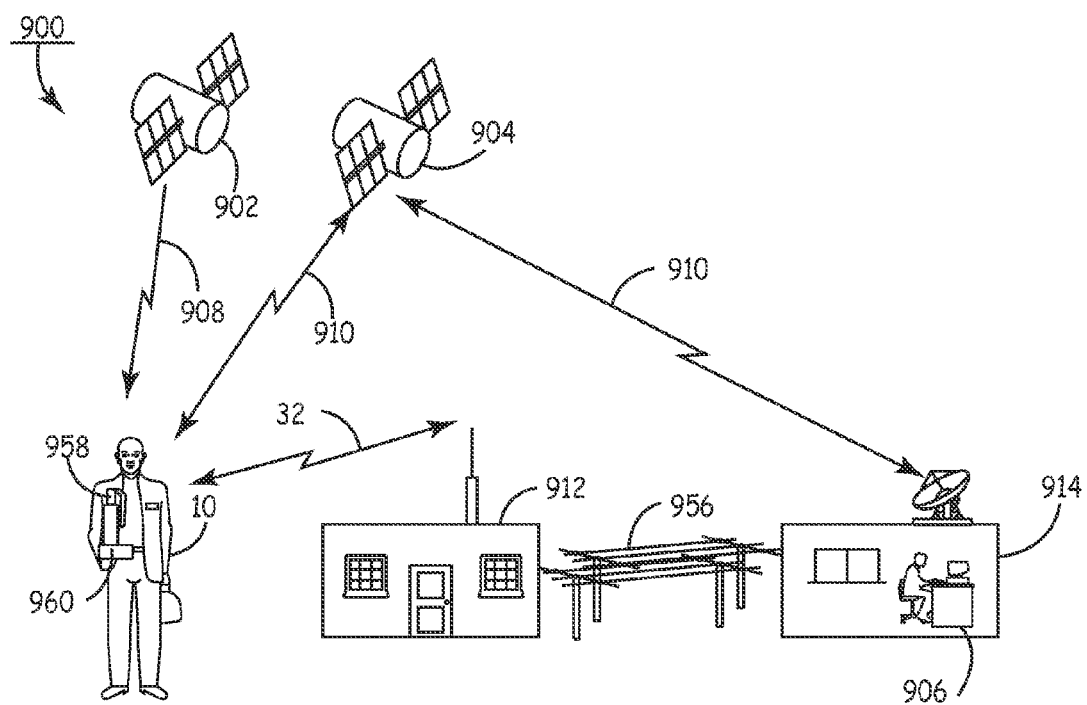

FIG. 58 is a schematic diagram of a system utilizing any of the above-described embodiments and allowing remote monitoring and diagnostic evaluation of at risk patients.

Figure 59:
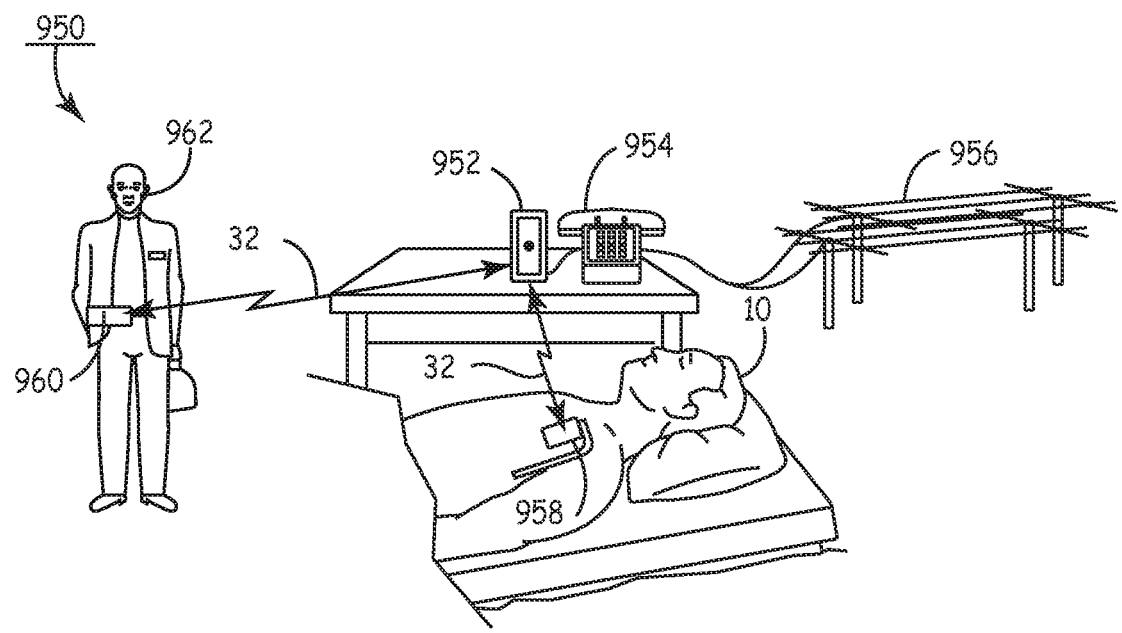

FIG. 59 is a schematic diagram of an alternative system utilizing any of the above-described embodiments and allowing remote monitoring and diagnostic evaluation of at risk patients.

DETAILED DESCRIPTION OF THE INVENTION

The term "brain monitoring element" used herein means any device, component or sensor that receives a physiologic signal from the brain or head of a patient and outputs a brain signal that is based upon the sensed physiologic signal. Some examples of a brain monitoring element include leads, electrodes, chemical sensors, biological sensors, pressure sensors, and temperature sensors. A monitoring element does not have to be located in the brain to be a brain monitoring element. The term brain monitoring element is not the same as the term "monitor" also used herein, although a brain monitoring element could be a part of a monitor.

The term "cardiac monitoring element" used herein means any device, component or sensor that receives or infers a physiological signal from the heart of a patient and outputs a cardiac signal that is based upon sensed physiologic signal. Some examples of cardiac monitoring elements include leads, electrodes, chemical sensors, biological sensor, pressure sensors and temperature sensors. A monitoring element does not have to be located in the heart or adjacent to the heart to be a cardiac monitoring element. For example, a sensor or electrode adapted for sensing a cardiac signal and placed on the housing of an implantable device is a cardiac monitoring element. Furthermore, a cardiac monitoring element could be an externally placed sensor such as a holter monitoring system. The term "cardiac monitoring element" is not the same as the term "monitor" also used herein although a cardiac monitoring element could be a part of a monitor.

The term "respiratory monitoring element" used herein means any device, component or sensor that receives a physiologic signal indicative of activity or conditions in the lungs of a patient and outputs a respiration signal that is based upon the sensed physiologic signal. Some examples of respiration monitoring elements are provided below. A monitoring element does not have to be located in the lungs or adjacent to the lungs to be a respiratory monitoring element. The term "respiratory monitoring element" is not the same as the term "monitor" also used herein although a respiratory monitoring element could be a part of a monitor.

It is noted that many embodiments of the invention may reside on any hardware embodiment currently understood or conceived in the future. Many example hardware embodiments are provided in this specification. These examples are not meant to be limiting of the invention.

Core Monitor

Cardiopulmonary monitoring in the Core Monitor device (as described below in more detail in conjunction with FIGS. 1-4 and 26-30) monitors cardiac (e.g., ECG, blood pressure) or respiration signals continuously and records these signals in a loop recorder either automatically or manually when the patient indicates they have had a neurological event such as a seizure. Real-time analysis of the ECG signal evaluates rate disturbances (e.g., bradycardia; tachycardia; asystole) as well as any indications of cardiac ischemia (e.g., ST segment changes; T wave inversion, etc.). Real-time analysis of the respiration signal evaluates respiration disturbances (e.g., respiration rate, minute ventilation, apnea, prolonged pauses).

Abnormalities detected during real-time analysis will lead to an immediate patient alert. This alert can be audible (beeps, buzzers, tones, spoken voice, etc.), light, tactile, or other means.

Automatic loop recording may save the data for a programmable period of time. For example, the device may be programmed to save a period of time before a cardiac detection (e.g., 30 seconds of ECG raw or processed data before detection) and a second period of time after the detection (e.g., 3 minutes of ECG raw or processed data after detection).

The medical device system may also include a manual activation mode in which the patient provides an indication (e.g., push a button on a holter, patient programmer or other external patient activator device) when a neurological event is occurring or has just occurred. In manual activation mode, to allow for the fact that the patient may not mark the neurological event until the neurological event has ended, the ECG loop recording may begin a longer time period before the event is marked. For example, the medical device system may save ECG data beginning 15 minutes before the patient mark. This time period may be programmable. Post-processing of this saved signal will analyze the data to evaluate heart rate changes during the neurological event, heart rate variability and changes in ECG waveforms. Manual patient indication of a neurological event will be done through the patient external activator device 22. The patient (or caregiver) will push a button on the external device, while communicating with the implanted device. This will provide a marker and will initiate a loop recording. In addition, prolonged ECG loop recordings are possible (e.g., in the case of SUDEP, recording all data during sleep since the incidence of SUDEP is highest in patients during sleep).

Post-processing of the signal can occur in the implanted device, the patient's external device or in the clinician external device. Intermittently (e.g., every morning, once/week, following a neurological event), the patient may download data from the implantable device to the patient external device. This data will then be analyzed by the external device (or sent through a network to the physician) to assess any ECG or respiratory abnormalities. If an abnormality is detected, the device will notify the patient/caregiver. At that time, the patient/caregiver or device can inform the healthcare provider of the alert to allow a full assessment of the abnormality. The clinician external device is also capable of obtaining the data from the implanted device and conducting an analysis of the stored signals. If a potentially life-threatening abnormality is detected, the appropriate medical treatment can be prescribed (e.g., cardiac abnormality: a pacemaker, an implantable defibrillator, or a heart resynchronization device may be indicated or respiration abnormality: CPAP, patient positioning, or stimulation of respiration may be indicated).

FIG. 1 is a simplified schematic view of one embodiment of a core Monitor 100 implanted in a patient 10. Monitor 100 continuously senses and monitors the cardiac and respiration function of patient 10 via one or more monitoring elements 14 (e.g., cardiac electrodes) to allow detection of neurological events, the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data.

Monitor 100, as stated above, typically includes one or more monitoring elements 14 such as several subcutaneous spiral electrodes that are embedded individually into three or four recessed casings placed in a compliant surround that is attached to the perimeter of implanted monitor 100 as substantially described in U.S. Pat. Nos. 6,512,940 "Subcutaneous Spiral Electrode for Sensing Electrical Signals of the Heart" to Brabec, et al and 6,522,915 "Surround Shroud Connector and Electrode Housings for a Subcutaneous Electrode Array and Leadless ECGS" to Ceballos, et al. These electrodes are electrically connected to the circuitry of the implanted Monitor 100 to allow the detection of cardiac depolarization waveforms (as substantially described in U.S. Pat. No. 6,505,067 "System and Method for Deriving a Virtual ECG or EGM Signal" to Lee, et al.) that may be further processed to detect cardiac electrical characteristics (e.g., heart rate, heart rate variability, arrhythmias, cardiac arrest, sinus arrest and sinus tachycardia). Further processing of the cardiac signal amplitudes may be used to detect respiration characteristics (e.g., respiration rate, minute ventilation, and apnea).

To aid in the implantation of Monitor 100 in a proper position and orientation, an implant aid may be used to allow the implanting physician to determine the proper location/orientation as substantially described in U.S. Pat. No. 6,496,715 "System and Method for Noninvasive Determination of Optimal Orientation of an Implantable Sensing Device" to Lee, et al.

FIG. 2 is a simplified schematic view of a second embodiment core Monitor 120 implanted in a patient 10. Monitor 120 continuously senses and monitors cardiac and respiration function of patient 10 via cardiac lead(s) 16 to allow detection of neurological events and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Monitor 120 senses both cardiac signals and respiration parameters via standard cardiac leads implanted in the heart. Monitor 120 measures intra-cardiac impedance, varying both with the intrathoracic pressure fluctuations during respiration and with cardiac contraction is representative of the pulmonary activity and of the cardiac activity as substantially described in U.S. Pat. No. 5,003,976 "Cardiac and Pulmonary Physiological Analysis via Intracardiac Measurements with a Single Sensor" to Alt. Cardiac leads 16 may consist of any typical lead configuration as is known in the art, such as, without limitation, right ventricular (RV) pacing or defibrillation leads, right atrial (RA) pacing or defibrillation leads, single pass RA/RV pacing or defibrillation leads, coronary sinus (CS) pacing or defibrillation leads, left ventricular pacing or defibrillation leads, pacing or defibrillation epicardial leads, subcutaneous defibrillation leads, unipolar or bipolar lead configurations, or any combinations of the above lead systems.

FIG. 3 is a simplified schematic view of a third embodiment core Monitor 140 implanted in a patient 10. Monitor 140 continuously senses and monitors cardiac and respiration function of patient 10 via an electrode (not shown) located distally on sensor stub 20 which is inserted subcutaneously in the thoracic area of the patient to allow detection of neurological events and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Monitor 140 senses cardiac signals between an electrode on the distal end of the sensor stub and the monitor case as described in conjunction with the embodiment shown in FIG. 5 in U.S. Pat. No. 5,987,352 "Minimally Invasive Implantable Device for Monitoring Physiologic Events" to Klein, et al. Monitor 140 also senses respiration parameters such as respiration rate, minute ventilation and apnea via measuring and analyzing the impedance variations measured from the implanted monitor 140 case to the electrode (not shown) located distally on sensor stub lead 20 as substantially described in U.S. Pat. Nos. 4,567,892 "Implantable Cardiac Pacemaker" and 4,596,251 "Minute Ventilation Dependent Rate Responsive Pacer" both to Plicchi, et al.

FIG. 4 is a simplified schematic view of a fourth embodiment core Monitor 160 attached to a patient 10. External patch Monitor 160 continuously senses and monitors cardiac and respiration function of patient 10 to allow detection of neurological events and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Also optionally, a button 38 on the external patch monitor 160 may be activated by the patient 10 to manually activate diagnostic data recording.

External patch Monitor 160 consists of a resilient substrate affixed to the patient's skin with the use of an adhesive which provides support for an amplifier, memory, microprocessor, receiver, transmitter and other electronic components as substantially described in U.S. Pat. No. 6,200,265 "Peripheral Memory Patch and Access Method for Use With an Implantable Medical Device" to Walsh, et al. The substrate flexes in a complimentary manner in response to a patient's body movements providing patient comfort and wearability. The low profile external patch Monitor 160 is preferably similar in size and shape to a standard bandage, and may be attached to the patient's skin in an inconspicuous location. Uplinking of stored physiologic telemetry data from the internal memory of external patch Monitor 160 may be employed to transfer information between the monitor and programmer 12.

Full Monitor

The term "full monitor" is used to describe a monitor that is capable of monitoring the brain (such as by monitoring a brain signal such as an electroencephalogram (EEG)) and additionally the heart or pulmonary system or both. This will allow the full monitor to collect neurological signals and at least one of the cardiovascular and respiratory signals in close proximity to neurological events detected (such as seizures) as well as notifying the patient/caregiver of a prolonged neurological event (such as status epilepticus). Cardiovascular and respiratory monitoring may occur around a neurological event (in the case of a seizure this is called peri-ictal). In distinction from the core monitor, in which patients/caregivers must notify the device that a neurological event has occurred, the full monitor device will detect the neurological event (based on the brain signal) and will automatically analyze the peri-ictal signals and initiate the loop recording. Monitoring of more than one physiologic signal allows for greater understanding of the total physiologic condition of the patient. For example, prolonged or generalized seizures put patients at higher risk for SUDEP, the EEG monitoring may be programmed to provide alerts when a neurological event has exceeded a pre-determined duration or severity.

FIG. 5 is a simplified schematic view of a full Monitor 200 implanted in a patient 10. Monitor 200 continuously senses and monitors cardiac, brain and respiration function of patient 10 via one or more brain monitoring elements 18 and one or more cardiac monitoring elements 14 or one or more respiratory monitoring elements 15. Brain monitoring elements 18 may be for example, one or more brain leads with one or more electrodes. Such a brain lead may be any lead capable of sensing brain activity such as EEG. For example, brain monitoring element 18 may be a deep brain lead, a cortical lead or an electrode placed on the head externally. Cardiac monitoring elements 14 may be cardiac leads or other types of sensors or electrodes capable of picking up cardiac signals. These monitoring elements allow detection of a neurological event and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. An implant aid may be used with Monitor 200 to ensure a proper position and orientation during implant as described above in connection with the system of FIG. 1.

FIG. 6 is a simplified schematic view of a second embodiment of a full Monitor 220 implanted in a patient 10. Monitor 220 continuously senses and monitors cardiac, brain and respiration function of patient 10 via cardiac lead(s) 16 and a brain lead 18 to allow detection of a neurological event and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data.

FIG. 7 is a simplified schematic view of a third embodiment of a full Monitor 240 implanted in a patient 10. Monitor 240 continuously senses and monitors cardiac, brain and respiration function of patient 10 via sensor stub 20 and brain lead 18 to allow detection of a neurological event and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data.

FIG. 8 is a simplified schematic view of a fourth embodiment of a full Monitor 260 implanted in a patient 10. Monitor 260 in combination with external patch 160 continuously senses and monitors cardiac, brain and respiration function of patient 10 to allow detection of a neurological event and the recording of data and signals pre and post event. A 2-way wireless telemetry communication link 30 connects the Monitor unit 260 and external patch 160. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Also optionally, a button 38 on the external patch monitor 160 may be activated by the patient 10 to manually activate diagnostic data recording.

An alternative embodiment of the system of FIG. 8 consists of software "patches" or programs downloaded from a wearable patch 38 into an implanted neurostimulator, drug pump or monitor to allow research evaluation of new therapies, detection algorithms, clinical research and data gathering and the use of the patient as their own "control" by randomly downloading or enabling a new detection algorithm or therapy and gathering the resultant clinical data (as substantially described in U.S. Pat. No. 6,200,265 "Peripheral Memory Patch and Access Method for Use with an Implantable Medical Device" to Walsh, et al). The clinical and diagnostic data may be uploaded into the memory of the patch for later retrieval and review by the patient's physician or device clinical manager. This embodiment also allows the upgrading of the existing implant base with temporary new or additional therapeutic and diagnostic features.

FIG. 9 is a simplified schematic view of a fifth embodiment of a full Monitor 280 implanted in a patient 10. Monitor 280 continuously senses and monitors cardiac, brain and respiration function of patient 10 via brain lead 18 with integrated electrode 24 to allow detection of a neurological event and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Integrated electrode 24 senses ECG signals as described above in the referenced Klein '352 patent and respiration signals as described above in the referenced Plicchi '892 and '251 patents.

FIG. 10 is a simplified schematic view of a sixth embodiment of a full Monitor 26 implanted cranially in a patient 10. Monitor 26 continuously senses and monitors cardiac, brain and respiration function of patient 10 to allow detection of a neurological event and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data. Monitor 26 may be constructed as substantially described in US Publication No. 20040176817 "Modular implantable medical device" to Wahlstrand et al. or U.S. Pat. Nos. 5,782, 891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads.

ECG sensing in the cranium may be accomplished by leadless ECG sensing as described in the above Brabec '940, Ceballos '915 and Lee '067 referenced patents. Alternatively, ECG rate and asystole may be inferred (along with a blood pressure signal) from a capacitive dynamic pressure signal (ie, dP/dt) as substantially described in U.S. Pat. No. 4,485, 813 "Implantable Dynamic Pressure Transducer System" to Anderson, et al. ECG rate and asystole may be inferred by monitoring an acoustic signal (i.e., sound) as substantially described in U.S. Pat. No. 5,554,177 "Method and Apparatus to Optimize Pacing Based on Intensity of Acoustic Signal" to Kieval, et al. The sensed acoustic signal is low pass filtered to limit ECG signals to 0.5-3 Hz while filtering out speech, swallowing and chewing sounds. ECG rate and asystole may be inferred (along with a blood saturation measurement) by monitoring a reflectance oximetry signal (i.e., $O_2$sat) as substantially described in U.S. Pat. No. 4,903,701 "Oxygen Sensing Pacemaker" to Moore, et al. ECG rate and asystole may be inferred by monitoring a blood temperature signal (i.e., dT/dt) as substantially described in U.S. Pat. No. 5,336,244 "Temperature Sensor Based Capture Detection for a Pacer" to Weijand. ECG rate and asystole may be inferred (along with an arterial flow measurement) by monitoring a blood flow signal (from an adjacent vein via impedance plethysmography, piezoelectric sensor or Doppler ultrasound) as substantially described in U.S. Pat. No. 5,409,009 "Methods for Measurement of Arterial Blood Flow" to Olson. ECG rate and asystole may be inferred (along with a blood pressure measurement) by monitoring a blood pressure signal utilizing a strain gauge substantially described in U.S. Pat. No. 5,168,759 "Strain Gauge for Medical Applications" to Bowman. ECG rate and asystole may be inferred by monitoring a blood parameter sensor (such as oxygen, pulse or flow) located on a V-shaped lead as substantially described in U.S. Pat. No. 5,354,318 "Method and Apparatus for Monitoring Brain Hemodynamics" to Taepke.

Monitor 26 may warn or alert the patient 10 via an annunciator such as buzzes, tones, beeps or spoken voice (as substantially described in U.S. Pat. No. 6,067,473 "Implantable Medical Device Using Audible Sound Communication to Provide Warnings" to Greeninger, et al.) via a piezo-electric transducer incorporated in the housing of monitor 26 and transmitting sound to the patient's 10 inner ear.

Monitor+Treatment (Brain)

FIG. 11 is a simplified schematic view of a full Monitor/Brain Therapy unit 300 implanted in a patient 10. Monitor/Brain Therapy unit 300 continuously senses and monitors cardiac, brain and respiration function of patient 10 via monitoring elements 14 and 18. Such monitoring elements may be subcutaneous electrodes and a brain lead to allow detection of a neurological event, the recording of data and signals pre and post event, and the delivery of therapy via brain lead. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. An implant aid may be used with Monitor/Brain Therapy device 300 to assist with positioning and orientation during implant as described above in connection with the system of FIG. 1.

FIG. 12A is a simplified schematic view of a second embodiment of a full Monitor/Brain Therapy unit 320 implanted in a patient 10. Monitor/Brain Therapy unit 320 continuously senses and monitors cardiac, brain and respiration function of patient 10 via cardiac lead(s) 16 and a brain lead 18 to allow detection of a neurological event, the recording of data and signals pre and post event, and the delivery of therapy via brain lead 18. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy.

FIG. 12B is a simplified schematic view of a third embodiment of a full Monitor/Brain Therapy system consisting of a thoracically implanted Monitor unit 321 in combination with a cranially implanted brain Monitor/Therapy unit 26. Monitor unit 321 continuously senses and monitors the cardiac and respiration function of patient 10 via cardiac lead(s) 16 to allow detection of a neurological event, the recording of data and signals pre and post event, and the delivery of therapy via Monitor/Therapy unit 26. A 2-way wireless telemetry communication link 30 connects the Monitor/Therapy unit 26 and cardiac/respiration monitor 321. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor 26 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing and brain stimulation is accomplished by the use of integrated electrodes in the housing of Monitor/Therapy unit 26 or, alternatively, by cranially implanted leads (not shown in FIG. 12B). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy.

FIG. 13 is a simplified schematic view of a fourth embodiment of a full Monitor/Brain Therapy unit 340 implanted in a patient 10. Monitor/Brain Therapy unit 340 continuously senses and monitors cardiac, brain and respiration function of patient 10 via sensor stub 20 and a brain lead 18 to allow detection of a neurological event such as a neurological event, the recording of data and signals pre and post event, and the delivery of therapy via brain lead 18. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy.

FIG. 14 is a simplified schematic view of a fifth embodiment of a full Monitor/Brain Therapy unit 360 implanted in a patient 10. Monitor/Brain Therapy unit 360 in combination with external patch 160 continuously senses and monitors cardiac, brain and respiration function of patient 10 via external patch 160 and a brain lead 18 to allow detection of neurological events, the recording of data and signals pre and post event, and the delivery of therapy via brain lead 18. A 2-way wireless telemetry communication link 30 connects the Monitor/Brain Therapy unit 360 and external patch 160. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Also optionally, a button 38 on the external patch monitor 160 may be activated by the patient 10 to manually activate diagnostic data recording and therapy delivery.

FIG. 15 is a simplified schematic view of a sixth embodiment of a full Monitor/Brain Therapy unit 380 implanted in a patient 10. Monitor/Brain Therapy unit 380 continuously senses and monitors cardiac, brain and respiration function of patient 10 via a brain lead 18 with integrated electrode 24 to allow detection of neurological events, the recording of data and signals pre and post event, and the delivery of therapy via brain lead 18. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Integrated electrode 24 senses ECG signals as described above in the referenced Klein '352 patent and respiration signals as described above in the referenced Plicchi '892 and '251 patents.

FIG. 20 is a simplified schematic view of a seventh embodiment of a full Monitor/Brain Therapy unit 26 implanted cranially in a patient 10. Monitor/Brain Therapy unit 26 in combination with leadless Monitor 400 continuously senses and monitors cardiac, brain and respiration function of patient 10 to allow detection of neurological events, the recording of data and signals pre and post event, and the delivery of therapy via brain lead 18. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. A 2-way wireless telemetry communication link 30 connects the Monitor/Therapy unit 26 and leadless Monitor 400. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). An implant aid may be used with Monitor device 400 to ensure a proper position and orientation during implant as described above in connection with the system of FIG. 1. Monitor 26 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads.

Monitor 26 may warn/alert the patient 10 via an annunciator such as, but not limited to, buzzes, tones, beeps or spoken voice (as substantially described in U.S. Pat. No. 6,067,473 "Implantable Medical Device Using Audible Sound Communication to Provide Warnings" to Greeninger, et al.) via a piezo-electric transducer incorporated in the housing of monitor 26 and transmitting sound to the patient's 10 inner ear.

FIG. 21 is a simplified schematic view of an eighth embodiment of a full Monitor/Brain Therapy unit 420 implanted cranially in a patient 10. Monitor/Brain Therapy unit 400 in combination with external patch core monitor 160 continuously senses and monitors cardiac, brain and respiration function of patient 10 to allow detection of neurological events, the recording of data and signals pre and post event, and the delivery of therapy via brain lead 18. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. A 2-way wireless telemetry communication link 30 connects the Monitor/Therapy unit 26 and leadless Monitor 400. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke).

Monitor 26 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads.

Monitor 26 may warn/alert the patient 10 via an annunciator such as, but not limited to, buzzes, tones, beeps or spoken voice (as substantially described in U.S. Pat. No. 6,067,473 "Implantable Medical Device Using Audible Sound Communication to Provide Warnings" to Greeninger, et al.) via a piezo-electric transducer incorporated in the housing of monitor 26 and transmitting sound to the patient's 10 inner ear.

Monitor+Treatment (Brain+Respiration)

FIG. 16A is a simplified schematic view of a full Monitor/Brain and Respiration Therapy unit 440 implanted in a patient 10. Monitor/Brain and Respiration Therapy unit 440 continuously senses and monitors cardiac, brain and respiration function of patient 10 via cardiac lead(s) 16 and a brain lead 18 to allow detection of neurological events, the recording of data and signals pre and post event, and the delivery of therapy via brain lead 18 and phrenic nerve lead 28. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation.

FIG. 16B is a simplified schematic view of a second embodiment of a full Monitor/Brain and Respiration Therapy system consisting of a thoracically implanted Monitor/Respiration Therapy unit 441 in combination with a cranially implanted brain Monitor/Therapy unit 26. Monitor unit 441 continuously senses and monitors the cardiac and respiration function of patient 10 via cardiac lead(s) 16 to allow detection of neurological events, the recording of data and signals pre and post event, the delivery of respiration therapy via phrenic nerve lead 28 and the delivery of brain stimulation via Monitor/Therapy unit 26. A 2-way wireless telemetry communication link 30 connects the Monitor/Therapy unit 26 and cardiac/respiration monitor and respiration therapy unit 441.

The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor 26 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing and brain stimulation is accomplished by the use of integrated electrodes in the housing of monitor 26 or, alternatively, by cranially implanted leads (not shown in FIG. 16B). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation.

FIG. 17 is a simplified schematic view of a third embodiment of a full Monitor/Brain and Respiration Therapy unit 460 implanted in a patient 10. Monitor/Brain and Respiration Therapy unit 460 continuously senses and monitors cardiac, brain and respiration function of patient 10 via sensor stub 20 and a brain lead 18 to allow detection of neurological events, the recording of data and signals pre and post event, and the delivery of therapy via brain lead 18 and phrenic nerve lead 28. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation.

FIG. 18 is a simplified schematic view of a fourth embodiment of a full Monitor/Brain and Respiration Therapy unit 480 implanted in a patient 10. Monitor/Brain and Respiration Therapy unit 480 continuously senses and monitors cardiac, brain and respiration function of patient 10 via a brain lead 18 with integrated electrode 24 to allow detection of neurological events, the recording of data and signals pre and post event, and the delivery of therapy via brain lead 18 and phrenic nerve lead 28. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation. Integrated electrode 24 senses ECG signals as described above in the referenced Klein '352 patent and respiration signals as described above in the referenced Plicchi '892 and '251 patents.

FIG. 19 is a simplified schematic view of a fifth embodiment of a full Monitor/Brain and Respiration Therapy unit 500 implanted in a patient 10. Monitor/Brain and Respiration Therapy unit 500 continuously senses and monitors cardiac, brain and respiration function of patient 10 via brain lead 18 and respiration lead 28 with integrated electrode 24 to allow detection of neurological events, the recording of data and signals pre and post event, and the delivery of therapy via brain lead 18 and phrenic nerve lead 28. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation. Integrated electrode 24 senses ECG signals as described above in the referenced Klein '352 patent and respiration signals as described above in the referenced Plicchi '892 and '251 patents.

Monitor+Treatment (Brain+Cardiac)

FIG. 24A is a simplified schematic view of a full Monitor/Brain and Cardiac Therapy unit 520 implanted in a patient 10. Monitor/Brain and Cardiac Therapy unit 520 continuously senses and monitors cardiac, brain and respiration function of patient 10 via cardiac lead(s) 16 and a brain lead 18 to allow detection of neurological events, the recording of data and signals pre and post event, and the delivery of therapy via brain lead 18 and cardiac lead(s) 16. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy.

FIG. 24B is a simplified schematic view of a second embodiment of a full Monitor/Brain and Cardiac Therapy system consisting of a thoracically implanted Monitor/Therapy unit 521 implanted in patient 10 in combination with a cranially implanted brain Monitor/Therapy unit 26. Monitor/Therapy unit 521 continuously senses and monitors the cardiac and respiration function of patient 10 via cardiac lead(s) 16 to allow detection of neurological events, the recording of data and signals pre and post event, the delivery of cardiac therapy via Monitor/Therapy unit 521 and the delivery of therapy via Monitor/Therapy unit 26. A 2-way wireless telemetry communication link 30 connects the Monitor/Therapy unit 26 and cardiac/respiration Monitor/Therapy unit 521. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor 26 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing and brain stimulation is accomplished by the use of integrated electrodes in the housing of monitor 26 or, alternatively, by cranially implanted leads (not shown in FIG. 24B). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy.

FIG. 22 is a simplified schematic view of a third embodiment of a full Monitor/Brain and Cardiac Therapy unit 540 implanted cranially in a patient 10. Monitor/Brain and Cardiac Therapy unit 540 in combination with external patient worn vest 34 continuously senses and monitors cardiac, brain and respiration function of patient 10 to allow detection of neurological events, the recording of data and signals pre and post event, and the delivery of therapy via brain lead 18 and vest 34. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. A 2-way wireless telemetry communication link 30 connects the monitor/therapy unit 540 and patient worn vest 34. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke).

Monitor/Therapy unit 540 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing is accomplished by the use of integrated electrodes in the housing of Monitor/Therapy unit 540 or, alternatively, by cranially implanted leads.

Monitor/Therapy unit 540 may warn/alert the patient 10 via an annunciator such as, but not limited to, buzzes, tones, beeps or spoken voice (as substantially described in U.S. Pat. No. 6,067,473 "Implantable Medical Device Using Audible Sound Communication to Provide Warnings" to Greeninger, et al.) via a piezo-electric transducer incorporated in the housing of monitor 26 and transmitting sound to the patient's 10 inner ear.

FIG. 23 is a simplified schematic view of a fourth embodiment of a full Monitor/Brain and Cardiac Therapy unit 560 implanted cranially in a patient 10. Monitor/Brain and Cardiac Therapy unit 560 in combination with leadless defibrillator 36 continuously senses and monitors cardiac, brain and respiration function of patient 10 to allow detection of neurological events, the recording of data and signals pre and post event, and the delivery of therapy via brain lead 18 and defibrillator 36. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. A 2-way wireless telemetry communication link 30 connects the monitor/therapy unit 560 and leadless defibrillator 36. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke).

Monitor/Therapy unit 560 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing is accomplished by the use of integrated electrodes in the housing of Monitor/Therapy unit 560 or, alternatively, by cranially implanted leads.

Monitor/Therapy unit 560 may warn/alert the patient 10 via an annunciator such as, but not limited to, buzzes, tones, beeps or spoken voice (as substantially described in U.S. Pat. No. 6,067,473 "Implantable Medical Device Using Audible Sound Communication to Provide Warnings" to Greeninger, et al.) via a piezo-electric transducer incorporated in the housing of Monitor/Therapy unit 560 and transmitting sound to the patient's 10 inner ear.

Monitor+Treatment (Brain+Respiration+Cardiac)

FIG. 25A is a simplified schematic view of a full Monitor/Brain, Respiration and Cardiac Therapy unit 580 implanted in a patient 10. Monitor/Brain, Respiration and Cardiac Therapy unit 580 continuously senses and monitors cardiac, brain and respiration function of patient 10 via cardiac lead(s) 16 and a brain lead 18 to allow detection of neurological events, the recording of data and signals pre and post event, and the delivery of therapy via brain lead 18, cardiac lead(s) 16 and phrenic nerve lead 28. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation.

FIG. 25B is a simplified schematic view of a second embodiment of a full Monitor/Brain, Respiration and Cardiac Therapy system consisting of a thoracically implanted Monitor/Respiration Therapy unit 581 in combination with a cranially implanted brain Monitor/Therapy unit 26. Monitor/Therapy unit 581 continuously senses and monitors the cardiac and respiration function of patient 10 via cardiac lead(s) 16 to allow detection of neurological events, the recording of data and signals pre and post event, the delivery of respiration therapy via phrenic nerve lead 28 and the delivery of brain stimulation via Monitor/Therapy unit 26. A 2-way wireless telemetry communication link 30 connects the Monitor/Therapy unit 26 and cardiac/respiration monitor/therapy unit 581. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor 26 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing and brain stimulation is accomplished by the use of integrated electrodes in the housing of monitor 26 or, alternatively, by cranially implanted leads (not shown in FIG. 25B). Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data and delivery of therapy. Optionally, lead 28 may connect to the diaphragm to provide direct diaphragmatic stimulation.

Core Monitor Design

Turning now to FIG. 26, there is shown a block diagram of the electronic circuitry that makes up core Monitor 100 (FIG. 1) in accordance with one embodiment of the invention. As can be seen from FIG. 26, Monitor 100 comprises a primary control circuit 720. Much of the circuitry associated with primary control circuit 720 is of conventional design, in accordance, for example, with what is disclosed in U.S. Pat. No. 5,052,388 to Sivula et al, entitled "Method and Apparatus for Implementing Activity Sensing in a Pulse Generator." To the extent that certain components of Monitor 100 are purely conventional in their design and operation, such components will not be described herein in detail, as it is believed that design and implementation of such components would be a matter of routine to those of ordinary skill in the art. For example, primary control circuit 720 in FIG. 26 includes sense amplifier circuitry 724, a crystal clock 728, a random-access memory and read-only memory (RAM/ROM) unit 730, a central processing unit (CPU) 732, a MV Processor circuit 738 and a telemetry circuit 734, all of which are well-known in the art.

Monitor 100 preferably includes internal telemetry circuit 734 so that it is capable of being programmed by means of external programmer/control unit 12 via a 2-way telemetry link 32 (shown in FIG. 1). Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn. Various telemetry systems for providing the necessary communications channels between an external programming unit and an implanted device have been developed and are well known in the art. Telemetry systems believed to be suitable for the purposes of practicing the present invention are disclosed, for example, in the following U.S. Patents: U.S. Pat. No. 5,127,404 to Wyborny et al. entitled "Telemetry Format for Implanted Medical Device"; U.S. Pat. No. 4,374, 382 to Markowitz entitled "Marker Channel Telemetry System for a Medical Device"; and U.S. Pat. No. 4,556,063 to Thompson et al. entitled "Telemetry System for a Medical Device".

Typically, telemetry systems such as those described in the above referenced patents are employed in conjunction with an external programming/processing unit. Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modeled as an air-core coupled transformer. An example of such a telemetry system is shown in the above-referenced Thompson et al. '063 patent.

In order to communicate digital data using RF telemetry, a digital encoding scheme such as is described in the above-referenced Wyborny et al. '404 patent can be used. In particular, for downlink telemetry a pulse interval modulation scheme may be employed, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encode a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen-position data frame may be defined, wherein a pulse in one of the time slots represents a unique four-bit portion of data.

As depicted in FIG. 26, programming units such as the above-referenced Medtronic Models 9790 and CareLink® programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

As previously noted, primary control circuit 720 includes central processing unit 732 which may be an off-the-shelf programmable microprocessor or microcontroller, but in the presently preferred embodiment of the invention is a custom integrated circuit. Although specific connections between CPU 732 and other components of primary control circuit 720 are not shown in FIG. 26, it will be apparent to those of ordinary skill in the art that CPU 732 functions to control the timed operation of sense amplifier circuit 724 under control of programming stored in RAM/ROM unit 730. It is believed that those of ordinary skill in the art will be familiar with such an operative arrangement.

With continued reference to FIG. 26, crystal oscillator circuit 728, in the presently preferred embodiment a 32,768-Hz crystal controlled oscillator, provides main timing clock signals to primary control circuit 720.

It is to be understood that the various components of monitor 100 depicted in FIG. 26 are powered by means of a battery (not shown), which is contained within the hermetic enclosure of monitor 100, in accordance with common practice in the art. For the sake of clarity in the figures, the battery and the connections between it and the other components of monitor 100 are not shown.

With continued reference to FIG. 26, sense amplifier 724 is coupled to monitoring elements 14 such as subcutaneous electrodes. Cardiac intrinsic signals are sensed by sense amplifier 724 as substantially described in U.S. Pat. No. 6,505,067 "System and Method for Deriving a Virtual ECG or EGM Signal" to Lee, et al. Further processing by CPU 732 allows the detection of cardiac electrical characteristics/anomalies (e.g., heart rate, heart rate variability, arrhythmias, cardiac arrest, sinus arrest and sinus tachycardia) that would be a matter of routine to those of ordinary skill in the art.

Further processing of the cardiac signal amplitudes may be used to detect respiration characteristics/anomalies (e.g., respiration rate, tidal volume, minute ventilation, and apnea) in MV Processor 738. FIG. 27 shows the intracardiac signals 770 presented to sense amplifier 724 from monitoring elements 14. Note the amplitude variation of cardiac signals caused by the change in thoracic cavity pressure due to respiration (ie, inspiration and expiration). By low pass filtering the cardiac signals 770, a signal representing minute ventilation may be obtained as depicted in waveform 772 (FIG. 27). This respiration signal may further be examined to detect respiration rate and reduced or absence of inspiration and expiration (central apnea) by CPU 732 and software resident in RAM/ROM 730.

Upon detection of either a cardiac or respiration anomaly, CPU 732, under control of computer executable instruction in firmware resident in RAM/ROM 730, will initiate recording of the appropriate diagnostic information into RAM of RAM/ROM 730, initiate a warning or alert to the patient, patient caregiver, or remote monitoring location. See flow diagram and description as described below in association with FIG. 31.

Turning now to FIG. 28, there is shown a block diagram of the electronic circuitry that makes up core Monitor 120 (FIG. 2) in accordance with another disclosed embodiment of the invention. As can be seen from FIG. 28, Monitor 120 comprises a primary control circuit 720 and a minute ventilation circuit 722. Much of the circuitry associated with primary control circuit 720 is of conventional design, in accordance, for example, with what is disclosed in U.S. Pat. No. 5,052,388 to Sivula et al, entitled "Method and Apparatus for Implementing Activity Sensing in a Pulse Generator." To the extent that certain components of Monitor 120 are purely conventional in their design and operation, such components will not be described herein in detail, as it is believed that design and implementation of such components would be a matter of routine to those of ordinary skill in the art. For example, primary control circuit 720 in FIG. 28 includes sense amplifier circuitry 724, a crystal clock 728, a random-access memory and read-only memory (RAM/ROM) unit 730, a central processing unit (CPU) 732, and a telemetry circuit 734, all of which are well-known in the art.

Monitor 120 preferably includes internal telemetry circuit 734 so that it is capable of being programmed by means of external programmer/control unit 12 via a 2-way telemetry link 32 (shown in FIG. 2). Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn. Various telemetry systems for providing the necessary communications channels between an external programming unit and an implanted device have been developed and are well known in the art. Telemetry systems believed to be suitable for the purposes of practicing the present invention are disclosed, for example, in the following U.S. Patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device".

Typically, telemetry systems such as those described in the above referenced patents are employed in conjunction with an external programming/processing unit. Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modeled as an air-core coupled transformer. An example of such a telemetry system is shown in the above-referenced Thompson et al. '063 patent.

In order to communicate digital data using RF telemetry, a digital encoding scheme such as is described in the above-reference Wyborny et al. '404 patent can be used. In particular, for downlink telemetry a pulse interval modulation scheme may be employed, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encode a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen-position data frame may be defined, wherein a pulse in one of the time slots represents a unique four-bit portion of data.

As depicted in FIG. 28, programming units such as the above-referenced Medtronic Models 9790 and CareLink® programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

With continued reference to FIG. 28, Monitor 120 is coupled to leads 16 which, when implanted, extend transvenously between the implant site of Monitor 120 and the patient's heart (not shown). For the sake of clarity, the connections between leads 16 and the various components of Monitor 120 are not shown in FIG. 28, although it will be clear to those of ordinary skill in the art that, for example, leads 16 will necessarily be coupled, either directly or indirectly, to sense amplifier circuitry 724 in accordance with common practice, such that cardiac electrical signals may be conveyed to sensing circuitry 724, via leads 16. Cardiac leads 16 may consist of any typical lead configuration as is known in the art, such as, without limitation, right ventricular (RV) pacing or defibrillation leads, right atrial (RA) pacing or defibrillation leads, single pass RA/RV pacing or defibrillation leads, coronary sinus (CS) pacing or defibrillation leads, left ventricular pacing or defibrillation leads, pacing or defibrillation epicardial leads, subcutaneous defibrillation leads, unipolar or bipolar lead configurations, or any combinations of the above lead systems.

Sensed cardiac events are evaluated by CPU 732 and software stored in RAM/ROM unit 730. Cardiac anomalies detected include heart rate variability, QT variability, $QT_C$, sinus arrest, syncope, ST segment elevation and various arrhythmias such as sinus, atrial and ventricular tachycardias.

Heart rate variability may be measured by the method and apparatus as described in U.S. Pat. No. 5,749,900 "Implantable Medical Device Responsive to Heart Rate Variability Analysis" to Schroeppel, et al and U.S. Pat. No. 6,035,233 "Implantable Medical Device Responsive to Heart Rate Variability Analysis" to Schroeppel, et al. Schroeppel '900 and '233 patents describe an implantable cardiac device that computes time intervals occurring between successive heartbeats and then derive a measurement of heart rate variability from epoch data for predetermined time periods. The Schroeppel device then compares measurement of heart rate variability with previously stored heart rate variability zones, which define normal and abnormal heart rate variability.

QT variability may be measured by the method and apparatus as described in U.S. Pat. No. 5,560,368 "Methodology for Automated QT Variability Measurement" to Berger. The Berger '368 patent utilizes a "stretchable" QT interval template started at the beginning of the QRS complex and terminating on the T-wave to determine beat-to-beat variability.

$QT_C$ may be measured by the method and apparatus as described in U.S. Pat. No. 6,721,599 "Pacemaker with Sudden Rate Drop Detection Based on QT Variations" to de Vries. The de Vries '599 patent measures QT interval real time and compares the instantaneous value to a calculated mean via a preprogrammed threshold change value.

Syncope may be detected by the methods and apparatus as described in U.S. Pat. No. 6,721,599 "Pacemaker with Sudden Rate Drop Detection Based on QT Variations" to de Vries. The de Vries '599 patent utilizes a sudden rate change and a real time QT interval measurement compared to a QT mean to detect sudden rate drop and neurally mediated syncope.

ST segment elevation (an indicator of myocardial ischemia) may be detected by the methods and apparatus as described in U.S. Pat. No. 6,128,526 "Method for Ischemia Detection and Apparatus for Using Same" to Stadler, et al and U.S. Pat. No. 6,115,630 "Determination of Orientation of Electrocardiogram Signal in Implantable Medical devices" to Stadler, et al. The Stadler '526 and '630 patents describe a system that compares a sampled data point prior to an R-wave complex peak amplitude to multiple samples post R-wave event to detect ST segment elevation.

Arrhythmias such as sinus, atrial and ventricular tachycardias may be detected by the methods and apparatus as described in U.S. Pat. No. 5,545,186 "Prioritized Rule Based Method and Apparatus for Diagnosis and Treatment of Arrhythmias" to Olson, et al.

Sinus arrest may be detected by the methods and apparatus as described above in the Olson '186 patent.

In the presently disclosed embodiment, two leads are employed—an atrial lead 16A having atrial TIP and RING electrodes, and a ventricular lead 16V having ventricular TIP and RING electrodes. In addition, as noted above, the conductive hermetic canister of Monitor 120 serves as an indifferent electrode.

As previously noted, primary control circuit 720 includes central processing unit 732 which may be an off-the-shelf programmable microprocessor or microcontroller, but in the presently preferred embodiment of the invention is a custom integrated circuit. Although specific connections between CPU 732 and other components of primary control circuit 720 are not shown in FIG. 28, it will be apparent to those of ordinary skill in the art that CPU 732 functions to control the timed operation of sense amplifier circuit 724 under control of programming stored in RAM/ROM unit 730. It is believed that those of ordinary skill in the art will be familiar with such an operative arrangement.

With continued reference to FIG. 28, crystal oscillator circuit 728, in the presently preferred embodiment a 32,768-Hz crystal controlled oscillator, provides main timing clock signals to primary control circuit 720 and to minute ventilation circuit 722.

It is to be understood that the various components of Monitor 120 depicted in FIG. 28 are powered by means of a battery (not shown), which is contained within the hermetic enclosure of Monitor 120, in accordance with common practice in the art. For the sake of clarity in the figures, the battery and the connections between it and the other components of Monitor 120 are not shown.

As shown in FIG. 28, primary control circuit 720 is coupled to minute ventilation circuit 722 by means of multiple signal lines, designated collectively as 738 in FIG. 28. An I/O interface 740 in primary control circuit 720 and a corresponding I/O interface 742 in minute ventilation circuit 722, coordinate the transmission of signals between the two units via control lines 738.

Minute ventilation circuit 722 measures changes in transthoracic impedance, which has been shown to be proportional to minute ventilation. Minute ventilation is the product of tidal volume and respiration rate, and as such is a physiologic indicator of changes in metabolic demand.

Monitor 120, in accordance with the presently disclosed embodiment of the invention, measures transthoracic impedance using a bipolar lead 16 and a tripolar measurement system. As will be hereinafter described in greater detail, minute ventilation circuit 722 delivers 30-microSec biphasic current excitation pulses of 1-mA (peak-to-peak) between a RING electrode of bipolar lead 16 and the conductive canister of monitor 120, functioning as an indifferent electrode CASE, at a rate of 16-Hz. The resulting voltage is then measured between a TIP electrode of lead 16 and the monitor 120 CASE electrode. Such impedance measurement may be programmed to take place in either the atrium or ventricle of the patient's heart.

The impedance signal derived by minute ventilation circuit 722 has three main components: a DC offset voltage; a cardiac component resulting from the heart's function; and a respiratory component. The frequencies of the cardiac and respiratory components are assumed to be identical to their physiologic origin. Since the respiratory component of the impedance signal derived by minute ventilation circuit 722 is of primary interest for this aspect of the present invention, the impedance signal is subjected to filtering in minute ventilation low-pass filter (MV LPF) 750 having a passband of 0.05- to 0.8-Hz (corresponding to 3-48 breaths per minute) to remove the DC and cardiac components.

With continuing reference to FIG. 28, minute ventilation circuit 722 includes a Lead Interface circuit 744 which is essentially a multiplexer that functions to selectively couple and decouple minute ventilation circuit 722 to the VTIP, VRING, ATIP, ARING, and CASE electrodes, as will be hereinafter described in greater detail.

Coupled to lead interface circuit 744 is a minute ventilation (MV) Excitation circuit 746 which functions to deliver the biphasic constant-current pulses between various combinations of lead electrodes (VTIP, VRING, etc.) for the purpose of measuring cardiac impedance. In particular, MV Excitation circuit 746 delivers biphasic excitation pulses (at a rate of 16-Hz between the ventricular ring electrode VRING and the pacemaker canister CASE) of the type delivered in accordance with the method and apparatus described in U.S. Pat. No. 5,271,395 "Method and Apparatus for Rate Responsive Cardiac Pacing" to Wahlstrand et al.

To measure cardiac impedance, minute ventilation circuit 722 monitors the voltage differential present between pairs of electrodes as excitation pulses are being injected as described above. Again, the electrodes from which voltage differentials are monitored will vary depending upon whether atrial or ventricular measurements are being made. In one embodiment of the invention, the same electrodes (i.e., VRING and CASE for ventricular, ARING and CASE for atrial) are used for both delivery of excitation pulses and voltage differential monitoring. It is contemplated, however, that the electrode combinations for excitation and measurement may be among the programmable settings, which may be altered post-implant with the programming system.

With continued reference to FIG. 28, the 16-Hz sampled output voltages from ZMEAS PREAMP circuit 748 are presented to the minute ventilation low-pass filter circuit MV LPF 750, which has a passband of 0.05-0.8 Hz in the presently preferred embodiment of the invention. Again, it is believed that the design and implementation of MV LPF circuit 750 would be a matter of routine engineering to those of ordinary skill in the art. The output from MV LPF circuit 750 is a voltage waveform whose level at any given time is directly proportional to cardiac impedance measured between the selected electrodes. Thus, the MV LPF output signal will be referred to herein as an impedance waveform. MV Calculation 752 analyzes the impedance waveform to determine/detect respiration rate, tidal volume, minute ventilation and presence of apnea.

The circuit of FIG. 28 may additionally monitor pulmonary edema by measuring the DC impedance between the distal electrodes of cardiac leads 16 and the case of core monitor 120. Measurement technique may be as substantially described in U.S. Pat. No. 6,512,949 "Implantable Medical Device for Measuring Time Varying Physiologic Conditions Especially Edema and for Responding Thereto" by Combs, et al.

Upon detection of a cardiac or respiration anomaly, CPU 732, under control of firmware resident in RAM/ROM 730, will initiate recording of the appropriate diagnostic information into RAM of RAM/ROM 730, initiate a warning or alert to the patient, patient caregiver, or remote monitoring location. See flow diagram and description as described below in association with FIG. 31.

Turning now to FIG. 29, there is shown a block diagram of the electronic circuitry that makes up core Monitor 140 with sensor stub 20 (FIG. 3) in accordance with another disclosed embodiment of the invention. As can be seen from FIG. 29, Monitor 140 comprises a primary control circuit 720 and a minute ventilation circuit 722, the function of which has been described in detail above in conjunction with the system of FIG. 28. Monitor 140 measures thoracic impedance from the case of monitor 140 to the distal end of a sensor stub lead 20 (a subcutaneously implanted sensor lead) via an impedance/voltage converter using a sampling frequency of approximately 16 Hz as substantially described in U.S. Pat. No. 4,596,251 "Minute Ventilation Dependant Rate Responsive Pacer" to Plicchi, et al. Respiration parameters are evaluated by CPU 732 and software resident in RAM/ROM 730.

Cardiac signals are sensed by sense amplifier 724 and evaluated by CPU 732 and software resident in RAM/ROM 730.

Upon detection of either/or a cardiac or respiration anomaly, CPU 732, under control of firmware resident in RAM/ROM 730, will initiate recording of the appropriate diagnostic information into RAM of RAM/ROM 730, initiate a warning or alert to the patient, patient caregiver, or remote monitoring location. See flow diagram and description as described below in association with FIG. 31.

Turning now to FIG. 30, there is shown a block diagram of the electronic circuitry that makes up external patch core Monitor 160 (FIG. 4) in accordance with another disclosed embodiment of the invention. As can be seen from FIG. 30, Monitor 160 comprises a primary control circuit 720 and a minute ventilation circuit 722, the function of which has been described in detail above in conjunction with the system of FIG. 28. Intrinsic cardiac signals are sensed by electrodes 161 affixed to the patient's skin, amplified by amplifier 724 and processed by CPU 732 and software program resident in RAM/ROM 730. Cardiac anomalies are detected such as heart rate variability, QT variability, $QT_C$, sinus arrest, and various arrhythmias such as sinus, atrial and ventricular tachycardias. Respiration sensing is accomplished by low pass filtering the sensed and amplified intrinsic cardiac signals as shown in FIG. 27. Respiration anomalies (such as reduced or cessation of tidal volume and apnea) are evaluated and detected by CPU 732 and software resident in RAM/ROM 730.

Upon detection of either/or a cardiac or respiration anomaly, CPU 732, under control of firmware resident in RAM/ROM 730, will initiate recording of the appropriate diagnostic information into RAM of RAM/ROM 730, initiate a warning or alert to the patient, patient caregiver, or remote monitoring location. See flow diagram and description as described below in association with FIG. 31.

FIG. 31 is a flow diagram 800 showing operation of a core Monitor sensing/monitoring cardiac and respiration parameters for the detection of neurological events as shown and described in embodiments in FIG. 1-4 above. Beginning at block 802, the interval between sensed cardiac signals are measured. At block 804, a rate stability measurement is made on each cardiac interval utilizing a heart rate average from block 806. At block 808, a rate stable decision is made based upon preprogrammed parameters. If YES, the flow diagram returns to the HR Measurement block 802. If NO, the rate stability information is provided to Format Diagnostic Data block 812.

At block 816, thoracic impedance is continuously measured in a sampling operation. At block 818, a MV and respiration rate calculation is made. At block 822, a pulmonary apnea decision is made based upon preprogrammed criteria. If NO, the flow diagram returns to MV Measurement block 816. If YES, the occurrence of apnea and MV information is provided to Format Diagnostic Data block 812. Format Diagnostic Data block 812 formats the data from the cardiac and respiration monitoring channels, adds a time stamp (ie, date and time) and provides the data to block 814 where the data is stored in RAM, SRAM or MRAM memory for later retrieval by a clinician via telemetry. Optionally, block 812 may add examples of intrinsic ECG or respiration signals recorded during a sensed episode/seizure. Additionally, optionally, block 815 may initiate a warning or alert to the patient, patient caregiver, or remote monitoring location (as described in U.S. Pat. No. 5,752,976 "World Wide Patient Location and Data Telemetry System for Implantable Medical Devices" to Duffin, et al.

Full Monitor Design

FIG. 32 is a block diagram of the electronic circuitry that makes up full Monitor 200 (FIG. 5) in accordance with the presently disclosed alternative embodiment of the invention. As can be seen from FIG. 32, Monitor 200 includes a primary control circuit 720 that is described herein above in conjunction with FIG. 26. In addition the full monitor of FIG. 30 also includes an amplifier 725 to amplify and sense EEG signals from a cranially implanted lead 18. The CPU 732, in conjunction with a software program resident in RAM/ROM 730, evaluates the information from the sensed cardiac, respiration and EEG signals, detects the onset of cerebral, cardiac or respiratory anomalies, may perform one or more algorithms or methods as described in this specification (such as determination of concordance between EEG and cardiac or respiratory signals, comparison of heart rates associated with certain neurological event time periods, etc.), formats and stores diagnostic data for later retrieval by the patient's clinician and, optionally, may warn or alert the patient, patient caregiver or remote monitoring location. See flow diagram and description below in association with FIG. 37.

FIG. 33 is a block diagram of the electronic circuitry that makes up full Monitor 220 with brain 18 and cardiac 16 leads (FIG. 6) in accordance with the presently disclosed alternative embodiment of the invention. As can be seen from FIG. 33, Monitor 220 comprises a primary control circuit 720 and MV circuit 722 that are described herein above in conjunction with FIG. 28. In addition, the full Monitor 220 of FIG. 33 also includes an amplifier 725 to amplify and sense EEG signals from a cranially implanted lead 18. The CPU 732, in conjunction with a software program resident in RAM/ROM 730, integrates the information from the sensed cardiac, respiration and EEG signals, detects the onset of cerebral, cardiac or respiratory anomalies, formats and stores diagnostic data for later retrieval by the patient's clinician and, optionally, may warn or alert the patient, patient caregiver or remote monitoring location. See flow diagram and description as described below in association with FIG. 37.

FIG. 34 is a block diagram of the electronic circuitry that makes up full Monitor 240 with a brain lead 18 and sensor stub 20 (FIG. 7) in accordance with the presently disclosed alternative embodiment of the invention. As can be seen from FIG. 34, Monitor 240 comprises a primary control circuit 720 and MV circuit 722 that are described herein above in conjunction with FIG. 28. In addition, the full Monitor 240 of FIG. 34 also includes an amplifier 725 to amplify and sense EEG signals from a cranially implanted lead 18. The CPU 732, in conjunction with a software program resident in RAM/ROM 730, integrates the information from the sensed cardiac, respiration and EEG signals, detects the onset of cerebral, cardiac or respiratory anomalies, formats and stores diagnostic data for later retrieval by the patient's clinician and, optionally, may warn or alert the patient, patient caregiver or remote monitoring location. See flow diagram and description as described below in association with FIG. 37.

FIG. 35 is a block diagram of the electronic circuitry that makes up external patch 160/full Monitor 260 with a brain lead 18 (FIG. 8) in accordance with the presently disclosed alternative embodiment of the invention. As can be seen from FIG. 35, Monitor 260 comprises a primary control circuit 720 and external patch comprises a cardiac/MV (minute ventilation) circuit 160, the functions of which have been described in detail above in conjunction with the system of FIG. 28. Intrinsic cardiac signals are sensed by electrodes affixed to the patient's skin, amplified by amplifier 724, sent to primary control circuit 720 and processed by CPU 732 and software program resident in RAM/ROM 730. Cardiac anomalies are detected such as heart rate variability, QT variability, $QT_C$, sinus arrest, and various arrhythmias such as sinus, atrial and ventricular tachycardias. Respiration sensing is accomplished by low pass filtering the sensed and amplified intrinsic cardiac signals as shown in FIG. 27 or, alternatively, by using the MV/Z measurement circuitry of external patch 160 as described above in connection with FIG. 28. Respiration anomalies (such as reduced or cessation of tidal volume and apnea) are evaluated and detected by CPU 732 and software resident in RAM/ROM 730.

The CPU 732, in conjunction with a software program resident in RAM/ROM 730, integrates the information from the sensed cardiac, respiration and EEG signals, detects the onset of cerebral, cardiac or respiratory anomalies, formats and stores diagnostic data for later retrieval by the patient's clinician and, optionally, may warn or alert the patient, patient caregiver or remote monitoring location. See flow diagram and description as described below in association with FIG. 37.

The circuitry and function of the device 240 shown in FIG. 34 and described herein above may also be used for the full Monitor 280 with integrated electrode 24 brain lead 18 (FIG. 9). As described above in association with core Monitor 240, thoracic impedance via impedance/voltage converter as measured from the case of monitor 240 to the sensor stub 20 using a sampling frequency of approximately 16 Hz as substantially described in U.S. Pat. No. 4,596,251 "Minute Ventilation Dependant Rate Responsive Pacer" to Plicchi, et al. The Monitor 280 of this alternative embodiment utilizes the same circuitry of Monitor 240 but connected to the integrated electrode 24 on brain lead 18 instead of the sensor stub of Monitor 240.

Upon detection of either/or a cardiac or respiration anomaly, CPU 732, under control of firmware resident in RAM/ROM 730, will initiate recording of the appropriate diagnostic information into RAM of RAM/ROM 730, initiate a warning or alert to the patient, patient caregiver, or remote monitoring location. See flow diagram and description as described below in association with FIG. 37.

FIG. 36 is a block diagram of the electronic circuitry that makes up full Monitor 26 (FIG. 10) in accordance with the presently disclosed alternative embodiment of the invention. As can be seen from FIG. 32, Monitor 26 comprises a primary control circuit 720 whose function is described herein above in conjunction with FIG. 26. In addition the full Monitor 26 of FIG. 32 also includes an EEG amplifier 725 to amplify and sense EEG signals from a cranially implanted lead 18 or, alternatively, device mounted electrodes. Additionally, Sensor Interface 727 powers up, amplifies and senses the cardiac and respiratory signals from anyone or more of the following cranially implanted sensors. ECG sensing in the cranium may be accomplished by leadless ECG sensing as described in the above Brabec '940, Ceballos '915 and Lee '067 referenced patents. Alternatively, cardiac rate and asystole may be inferred from a dP/dt signal described above in the Anderson '813 patent; an acoustic signal described above in the Kieval '177 patent; an $O_2$sat signal described above in Moore '701 patent; a dT/dt signal described above in the Weijand '244 patent; a flow signal described above in the Olson '009; a strain gauge signal described above in the Bowman '759 patent; and a blood parameter sensor (such as oxygen, pulse or flow) located on a V-shaped lead described in the Taepke '318 patent.

The CPU 732, in conjunction with a software program resident in RAM/ROM 730, integrates the information from the sensed cardiac, respiration and EEG signals, detects the onset of cerebral, cardiac or respiratory anomalies, formats and stores diagnostic data for later retrieval by the patient's clinician and, optionally, may warn or alert the patient, patient caregiver or remote monitoring location. See flow diagram and description as described below in association with FIG. 37.

FIG. 37 is a flow diagram 840 showing operation of a full monitor sensing and monitoring cardiac, respiration and electroencephalogram parameters for the detection of neurological events as shown and described in embodiments in FIG. 5-10 above. Beginning at block 802, the interval between sensed cardiac signals are measured. At block 804, a rate stability measurement is made on each cardiac interval utilizing a heart rate average from block 806. At block 808, a rate stable decision is made based upon preprogrammed parameters. If YES, the flow diagram returns to the HR Measurement block 802. If NO, the rate stability information is provided to Format Diagnostic Data block 812.

At block 816, thoracic impedance is continuously measured in a sampling operation. At block 818, a MV and respiration rate calculation is made. At block 822, a pulmonary apnea decision is made based upon preprogrammed criteria. If NO, the flow diagram returns to MV Measurement block 816. If YES, the occurrence of apnea and MV information is provided to Format Diagnostic Data block 812.

At block 824, the electroencephalogram is sensed and measured. An EEG seizure determination is performed at block 826 as described in US published application 2004/0138536 "Clustering of Recorded Patient Neurological Activity to Determine Length of a Neurological Event" to Frei, et al incorporated herein by reference. At block 828, a seizure cluster episode is determined. If NO, the flow diagram returns to EEG Measurement block 824. If YES, the occurrence of a seizure cluster is provided to Format Diagnostic Data block 812. Format Diagnostic Data block 812 formats the data from the cardiac, respiration and EEG monitoring channels, adds a time stamp (ie, date and time) and provides the data to block 814 where the data is stored in RAM memory for later retrieval by a clinician via telemetry. Optionally, block 812 may add examples of intrinsic ECG, respiration or EEG signals recorded during a sensed episode/seizure. Additionally, optionally, block 815 may initiate a warning or alert to the patient, patient caregiver, or remote monitoring location (as described in U.S. Pat. No. 5,752,976 "World Wide Patient Location and Data Telemetry System for Implantable Medical Devices" to Duffin, et al.

FIG. 38 is a diagram 850 of exemplary physiologic data from a patient 10 with a full monitor as described herein above showing an EEG signal 852 and an ECG signal 854. A first epileptic seizure is shown at 856 (pre-ictal segment 851, ictal segment 853 and post-ictal segment 855) and detected at 864 and a second seizure is shown at 858 (pre-ictal segment 857, ictal segment 859 and post-ictal segment 861) and detected at 866 by the full monitor. The ECG signal 854 shows a first arrhythmic episode at 860 and detected at 868 and a second arrhythmic episode at 862 and detected at 870 by the full monitor. Note that the first epileptic seizure 864 and arrhythmic episode 868 are co-incident and "matched". Note that in the diagram 850 arrhythmic episode 870 and seizure episode 866 are not co-incident and are "unmatched".

Segmenting a Cardiac or Respiratory Signal According to Brain Detection Results.

One embodiment of the inventive system provides an automated method of processing cardiac signals in a full monitoring device for a nervous system disorder, to screen for cardiac abnormalities/heart rate changes and respiratory abnormalities during or within a specified time period of a neurological event. This embodiment medical device system and method reports a patient's heart or pulmonary condition for each neurological event detected in the brain signal.

In a monitoring device for epilepsy, brain signals are monitored/processed with a seizure detection algorithm; the cardiac and respiratory signals are passively recorded during the brain signal processing. When a seizure has been detected in the brain signal data stream, a recording containing a montage of brain, cardiac and respiratory signals is created. The signals in the recording are then post-processed to evaluate the patient's heart and pulmonary condition. A description of the post-processed design is shown in FIG. 39.

FIG. 39 shows a process 750 for identifying ECG and respiratory abnormalities recorded during detected seizures. At block 751, the full monitor monitors EEG and ECG or respiratory signals. At block 752, the monitor detects seizures in EEG signals. At block 753, seizure detection triggers recording of EEG, ECG and respiratory signals. After uplinking to a programmer, the ECG/respiratory signals are post processed. At block 755, ECG and respiratory signals are segmented into (a) pre-ictal, (b) ictal, and (c) post-ictal periods, as defined in the corresponding EEG for the detected seizure. The ictal periods are automatically derived from a seizure-detection algorithm operating on the EEG signals. For example, the beginning of the ictal period may be time-marked to detection cluster onset; the end of the ictal period by detection cluster offset (as described in published US Application No. 2004/0138536 "Clustering of Recorded Patient Neurological Activity to Determine Length of a Neurological Event" to Frei, et al incorporated herein by reference in its entirety). The durations of the pre-ictal and post-ictal periods are programmable. It may be desirable to program the pre-ictal period for purposes of a cardiac baseline or respiratory baseline as ending some period of time before the true ictal period as determined by the EEG detector. In this way a better baseline may be obtained that is not distorted by changes in cardiac or respiratory activity near in time to the neurological event.

At block 756, the loop-recorded data is screened for abnormalities. After the ECG and respiratory signals are segmented, the different intervals of ECG and respiratory data are separately processed to detect events reflected in those signals. For example, detection of a cardiac event may include computation of indices of heart rate (HR) (i.e., mean, median, max, std. dev., etc.) or indications of an some abnormal heart activity such as an arrhythmia which are displayed in the physician programmer for each detected event. A respiratory event may be determined from many signals including, but not limited to, minute ventilation, respiration rate, apnea, or edema, which are displayed in the physician programmer for each detected event. To monitor changes in cardiovascular and pulmonary function that may arise from or cause seizures, percentage of change between indices is calculated. For example, to indicate magnitude of change in heart rate from a baseline to seizure state, the percentage of change between the pre-ictal (baseline) and ictal (seizure) periods is computed/displayed.

% Chg. Detect Onset=(Ictal HR indices−Base HR indices)/Base HR indices

Comparison between the post-ictal and baseline periods is also performed to evaluate if and when a return to baseline is achieved.

% Chg. Detect End=(Post-Ictal HR indices−Base HR indices)/Base HR indices

During processing, the time at which the post-ictal heart rate returns to baseline, relative to the end of the ictal period, is identified. The physician may choose to increase the duration of the post-ictal period if, during detected seizures, the patient's HR indices do not consistently return to baseline levels.

At block 757, detection times for arrhythmic and respiratory anomalies are determined. The ECG and respiratory signals are further processed, via an arrhythmia/abnormality detection algorithm, to identify ECG and respiratory abnormalities (bradycardia, tachycardia, asystole, ST segment depression, QTc prolongation, apnea, edema, etc.). Such events may occur in different periods of data, and cross ictal boundaries (e.g., a tachy event may begin prior to seizure onset, and continue well after seizure termination, resulting in a detection that includes all intervals of data). Thus, during screening the entire ECG and respiration signals in the loop recording data is processed in a single step, without segmentation. The start and end times for each identified arrhythmia/ abnormality in the loop recording data is stored and later retrieved for analysis.

The physician runs a matching test (EEG detections versus ECG or respiratory detections) at block 758. The matching test is run to compare the EEG detections and ECG/respiratory detections in the loop recording data. The matching test reports whether each ECG/respiratory abnormality is coincident with (i.e., matched), or is temporally separated from, the detected seizure (i.e., unmatched). In the case of a match, the time difference between EEG detection onset and ECG/respiratory detection onset is computed.

At block 759, the matching test results are evaluated to determine if the seizure is associated with an arrhythmia or respiratory anomaly. At block 760, additional seizures are determined. If NO, block 761 reports results of ECG/respiratory screening procedures for each seizure. At block 760, if the result is YES the flow diagram returns to block 752.

ECG/respiratory post-processing may occur in the implantable device, after the loop recorded data has been stored to memory. Alternatively, the post-processing may occur on loop-recorded data transmitted to an external wearable device or physician programmer or other computer.

Determination of Improvements in Neurological Event Detection Using Cardiac or Respiratory Input Another embodiment of the invention is a medical device system and method for determining whether cardiac or respiratory signals may be used to improve neurological event detection. This medical device system includes a brain monitoring element (e.g., lead 18, external electrode), a cardiac monitoring element (e.g., lead 16, sensor stub 20, sensor 14, integrated electrode 24, external electrode, etc.) or respiratory monitoring element (e.g., lead 16, sensor stub 20, sensor 14, integrated electrode 24, external electrode, etc.) and a processor (e.g., CPU 732 or any other processor or combination of processors implanted or external). This determination of whether cardiac or respiratory signals may be used to improve neurological event detection may be very beneficial to understanding a patient's condition and that in turn is helpful to determining appropriate treatment or prevention options. The medical device system may include the ability to determine relationships between brain and heart only, brain and respiratory only, or both. Once these relationships are better understood, they may be utilized to make decisions about enabling the use of cardiac signals or cardiac detections or respiratory signals or respiratory detections in the monitoring or treatment of the neurological disorder. Note that this medical device system and method may be performed by many different types of hardware embodiments including the example hardware embodiments provided in this specification as well as in an external computer or programmer. The executable instructions executed by a processor may be stored in any computer readable medium such as, for example only, RAM 730.

The determination of improvements in neurological event detection using cardiac or respiratory input includes determination of concordance between brain and cardiac signals or between brain and respiratory signals, determination of detection latency, and the false positive rate in the cardiac or respiratory signal relative to a neurological event detected in the brain signal.

An example of the usefulness of this determination is provided here. If it is determined that a patient with epilepsy has improvement in neurological event detection based on a cardiac signal it may be desirable to enable the use of a cardiac activity detection algorithm to trigger application of therapy to the brain. Another example of the benefit of concordance information is that a high concordance between brain and heart (including perhaps concordance with a particular type of cardiac event) for an individual with epilepsy, may mean that the patient is more susceptible to SUDEP. Perhaps steps can be taken such as use or implantation of a heart assist device such as a pacemaker or defibrillator for this patient to reduce the likelihood of death. There are of course many other examples of situations that may be discovered by operation of this concordance system and method that result in better health care.

The medical device system with concordance capability may include a brain monitoring element 18 (e.g., EEG lead with one or more electrodes) for sensing activity of the brain and outputting a brain signal, and a cardiac or respiratory monitoring element 14 (e.g., electrodes or other sensors) or both, for sensing a cardiac or respiratory activity and outputting a cardiac or respiratory signal, and a processor. The processor is configured to receive the brain signal and one or more of the cardiac and respiratory signals and to compare the brain signal and one of the cardiac or respiratory signals to each other.

Comparison of the brain and cardiac signals to each other may take many different forms. In one embodiment, the processor is configured to obtain information identifying one or more neurological events in the brain signal, and to also obtain information identifying one or more cardiac events in the cardiac signal. "Obtain" means 1) automatically generating the information by executing an algorithm that evaluates the signal, or 2) receiving the information from a user such as a physician reviewing the brain and cardiac signals (this second aspect of obtain is hereinafter referred to as "manual identification of events"). The algorithm or physician may create or generate various features of the neurological event such as a determination of when the event begins and ends and hence a duration of the event. For example automatic generation of the information may be performed by a seizure detection algorithm such as described in US published application 2004/0138536 "Clustering of Recorded Patient Neurological Activity to Determine Length of a Neurological Event" to Frei, et al. Likewise in the case of a cardiac signal, any algorithm that evaluates a cardiac signal and outputs information about cardiac activity or abnormalities would be an automatic generation of the information. Some examples are presented above in the discussion of the core monitor. An example of a manual identification of an event includes a physician indicating to a physician programmer the temporal location of a neurological event and also indicating the temporal location of cardiac or respiratory events. This temporal location of an event may include marking of the beginning and end of the event.

In the case of manual identification of an event, the medical device system may include a user interface (for example, on a programmer or computer), for display of the brain, cardiac and respiration signals. The user, such as a physician, may mark events on the programmer. For example, the physician could mark the location by clicking a cursor over the location on the monitor. In another example, the physician could mark a location with a stylus on a touch sensitive screen. The physician markings may include marks that indicate the beginning and the end of an event.

In a more specific embodiment, the comparison of the brain signal to the cardiac or respiration signal includes for each neurological event, determining whether the neurological event is within a specified time period of one of the one or more cardiac or respiratory events, and for each of the one or more cardiac or respiratory events determining whether the cardiac or respiratory event is within a specified time period of one of the one or more neurological events. Two events are "within a specified time period" of each other if the two events are overlapping in time or the amount of time between two reference points of the two events is less than a time period that is previously determined and set in the device or that has been programmed or may be programmed into the device. Reference points of an event are some measure or indication of the temporal position of the event. For example, the two reference points may be the end of the first of the events to end and the beginning of the other event. Other reference points may be used such as, but not limited to, the midpoints of each of the events. An example of a specified time period that could be programmed into the device is 10 seconds. So in this example, the neurological event and the cardiac event would be within the specified time period of each other if a chosen reference point for the cardiac event (e.g., end of the cardiac event) was within 10 seconds of a chosen reference point (e.g., beginning of the neurological event) for the neurological event.

The comparison of brain signal to cardiac signal may include the following: determining the number of neurological events that are matched with a cardiac event (i.e., within a specified time period of a cardiac event); determining the number of neurological events that are matched with a cardiac event (i.e., not within the specified time period of a cardiac event); and determining the number of cardiac events that are not within the specified time period of a neurological event (the false positive rate in the ECG signal). The same steps may be applied in the case of comparison of a brain signal to a respiratory signal.

Furthermore for matched events (events that are within the specified time period of each other), the processor may determine the temporal relationship of the neurological event and the matched cardiac event or between the neurological event and the matched respiratory event. Because matched events may overlap or they may not overlap, the temporal relationship may be defined or described in many different ways. One embodiment of determining the temporal relationship is determining the temporal order (which event is first to occur) of the matched events. In order to determine the temporal order between two events, a reference point must be determined. As mentioned earlier the reference point may be the end, start or midpoint of an event, or the reference point may be computed in some other way. In general a reference point indicates some temporal information about the event. The reference points may then be compared to determine which occurred first. The event associated with the first to occur reference point is then the first to occur event.

In another embodiment of comparing the brain signal to a cardiac or respiratory signal, the processor is configured to compute a rate of concordance between the neurological events and the cardiac or respiratory events. In this embodiment, the processor is configured to categorize the neurological event as cardiac matched when there is a cardiac event within a specified time period of the neurological event. The processor computes the rate of concordance between the neurological events and the cardiac events based on the number of cardiac matched events and the number of neurological events. For example, the processor may compute the rate of concordance by calculating the number of cardiac matched events divided by the number of neurological events. The more matches the greater the concordance.

In another embodiment the processor is further configured to perform the following: dividing the neurological event into at least two segments; and assigning the cardiac event to one or more of the segments according to when the cardiac event occurred relative to the segments. For example, if the neurological event is a seizure, then there may be three segments: a pre-ictal segment, an ictal segment, and a post ictal segment. Various methods may be used to assign a cardiac event to one of these segments. For example, an algorithm executed by the processor (e.g., any of the processors of the many hardware embodiments in this application such as cpu 732, or a processor in a programmer or other computer external to the body) may determine when the cardiac event started relative to the three segments and assign the cardiac event to the segment in which it started. Of course other methods, more complex or simple may be used to make this assignment.

The ECG algorithm may be automatically enabled/disabled for use in monitoring or treatment (as described herein below) if concordance, detection latency and false positive rates meet selected and programmable criteria, indicating an improvement in neurological event detection performance. Alternatively, the patient's clinician may choose to review matching results and manually enable/disable the ECG detector based on information provided. For example, detection of a cardiac event may result in turning a neurostimulator or drug delivery device on to prevent the onset of a seizure. Alternatively, detection of a cardiac event may result in modification of therapy parameters. In another alternative, the ECG detector may be enabled for purposes of recording ECG, EEG or some other data.

In the embodiment that includes therapeutic output, the medical device system further includes a neurological therapy delivery module configured to provide a therapeutic output to treat a neurological disorder when the cardiac event detection algorithm detects a cardiac event. A neurological therapy delivery module may be any module capable of delivery a therapy to the patient to treat a neurological disorder. For example, but not limited to, a neurological therapy delivery module may be an electrical stimulator (e.g., stimulator 729), drug delivery device, therapeutic patch, brain cooling module.

Depending on the individual patient, and depending on the particular neurological disorder of concern, there may be different levels of concordance between different types of cardiac events and the neurological events. Therefore, in another embodiment, the processor is further configured to obtain information categorizing each cardiac event as one or more of two or more types of cardiac events. Types of cardiac events are known by different signals or aspects of signals coming from the heart. Examples of different types of cardiac events include: tachyrhythmia, ST segment elevation, bradycardia, asystole. In this embodiment, the processor may then determine concordance between each type of cardiac event or subset of cardiac events and neurological events. One embodiment of such determination is a processor configured to categorize each neurological event as first type cardiac matched when there is a first type cardiac event within a specified time period of the neurological event. The processor further categorizes the neurological event as second type cardiac matched when there is a second type cardiac event within a specified time period of the neurological event. The processor further computes a first rate of concordance between the neurological events and the first type cardiac events based on the number of first type cardiac matched events and the number of neurological events. The processor also computes a second rate of concordance between the neurological events and the second type cardiac events based on the number of second type cardiac matched events and the number of neurological events. This computation of rate of concordance may be performed as many times as there are types of cardiac events. The categorization of events as well as the various computed rates of concordance may be stored in memory.

In the embodiment allowing for computation of specific type of cardiac event rates of concordance, the medical device system may further include the capability to enable the use of detection of a particular type of cardiac event to affect the provision of therapy to the patient for the neurological disorder. For example, if it is determined that a high rate of concordance exists between tachyarrhythmia and seizure, the enablement of cardiac detection for affecting seizure therapy may be limited to the detection of tachyarrythmia. In this case the seizure therapy will not be affected by other types of cardiac events.

It is noted that the medical device system may be external to the patient's body, implanted or some combination. The processor itself may be either external or implanted. For example, the processor may be in a handheld unit such as a programmer, or the processor could be in a general purpose computer.

The various processor operations described above may be embodied in executable instructions and stored in a computer readable medium. The processor then operates to perform the various steps via execution of these instructions. At one level, the executable instructions cause the processor to receive a brain signal from a brain monitoring element, receive a cardiac signal from a hear monitoring element, and compare the brain signal to the cardiac signal.

As described above, in a full monitor device for epilepsy, EEG, respiratory and cardiac (ECG) physiologic signals are simultaneously monitored and processed by different algorithms. A seizure-detection algorithm detects seizure activity in the EEG signals. A second algorithm detects heart-rate changes, ECG abnormalities, or unique waveform patterns in the ECG signals, which may or may not be coincident with seizures. Additionally, a third algorithm detects minute ventilation, respiration rate and apnea, which also may or may not be coincident with seizures.

By default, the EEG is considered a 'primary signal'—detections from this signal are used to represent seizure. The ECG and respiratory signals are 'secondary signals'—it is not initially known whether events detected in these two signals are useful for seizure detection. In a treatment setting, the patient's clinician considers the stored signals and data to determine if processing the ECG and respiratory signals provides added benefit in improving detection performance.

To make this determination, the patient is monitored until a sufficient number of detections in one or both of the data streams are observed (number of required events is programmable). Events detected in the EEG data stream may be classified by the user, via the programmer interface, to indicate whether they are clinical seizures (TP-C), sub-clinical seizures (TP-N), or false positive detections (FP). Likewise, events detected in the ECG and respiratory signals may be classified to indicate type of abnormality detected.

The concordance between the EEG seizure detections and ECG and respiratory signals is then evaluated. This is accomplished in one of two ways:

The relation between the EEG and ECG detections is initially unknown. Determination of the relationship between EEG and ECG may be performed with post processing or in real time.

In the post processing embodiment, automated matching tests are performed to identify the temporal relationship of detections in the different data streams. The matching tests identify the number of EEG detections that are within a specified time period with ECG or respiratory abnormalities (EEG-ECG Match or EEG-Respiratory Match, see 864 and 868 FIG. 38), and those that are not (EEG detect-ECG Normal or EEG detect-Respiratory Normal). For matched detections, the time difference between EEG detection onset and ECG or respiratory detection onset is computed (detection latency). The number of detected events in the ECG or respiratory signals, independent of EEG triggered events, are also computed (ECG Un-matched or Respiratory Un-Matched, see 870 FIG. 38).

With the real time implementation, the device controls a flag set by the seizure-detection algorithm operating on EEG signals. The flag is a real-time indicator of the subject's seizure state (1=in EEG detection state; 0=out of EEG detection state). In real-time, the device monitors the co-occurrence of the EEG and ECG/respiratory detection states.

The following conditions are assessed:

Brain-Cardiac Match—The EEG event (e.g., seizure) is classified as matched with ECG event if the ECG detection state occurs during an EEG detection state or within a specified time period of an EEG detection state.

Brain-Respiratory Match—The EEG event (e.g., seizure) is classified as matched with respiratory event if the respiratory detection state occurs during an EEG detection state or within a specified time period of an EEG detection state.

Brain Detect-Cardiac Normal—The EEG event (e.g., seizure) is classified as matched with normal ECG if no ECG detection state occurs during an EEG detection state or within a specified time period of an EEG detection state.

Brain Detect-Respiratory Normal—The EEG event (e.g., seizure) is classified as matched with normal respiration if no respiratory detection state occurs during an EEG detection state or within a specified time period of the EEG detection state.

Cardiac Un-Matched—An ECG event is classified as un-matched to EEG event (e.g., seizure) if no EEG detection state occurs during the ECG detection state or within a specified time period of an ECG detection state.

Respiratory Un-Matched—A respiratory event is classified as un-matched to EEG event (e.g., seizure) if no EEG detection state occurs during the respiratory detection state or within a specified time period of the respiratory detection state.

After EEG-ECG or EEG-respiratory matching has been performed, the physician programmer indicates whether the following conditions are true: (1) a high rate of concordance between detections in the EEG and ECG data streams (or between the EEG and respiratory data streams); (2) earlier detection in the ECG signal (or respiratory signal) relative to neurological event onset as indicated in the EEG signal; and (3) a low rate of FP's in the ECG signal (or in the respiratory signal). If these conditions are all true, this may indicate that the ECG signal (or respiratory signal) provides value in neurological event detection (e.g., seizure detection).

Using this information, the physician may choose to activate the ECG algorithm or activate the respiration algorithm—that is, enable it as a primary signal for use in neurological event detection. Determination of whether to "add in" the ECG or respiratory signals (activate it in combination with the EEG signal) for seizure monitoring or treatment is based on satisfying one or more of the above stated conditions. This process can be automated by defining programmable threshold values for each of the stated conditions.

Note that ECG detection and respiratory detection may both be enabled or activated for neurological event detection if they both meet the conditions above.

The physician may decide not to enable the ECG/respiratory algorithms if the matching tests show no additional improvements in detection performance using the ECG or respiratory signals, or if specificity in the ECG/respiratory signals is low. In such cases, the physician may enable a mode of passive ECG recording, with the intended use of documenting cardiovascular changes during ictal periods in the EEG.

FIG. 40A shows a process 971 for determining whether to enable the cardiac or respiratory detection algorithms for neurological event detection. At block 974 the medical device system monitors a brain signal and, cardiac or respiratory signals. At block 975 detections in any of the 3 signals (brain, cardiac, respiratory) triggers loop recording. Determination of the bounds of the neurological, cardiac and respiratory events may be performed in various ways. In one embodiment this determination of the bounds of events may be performed by a physician. In another embodiment, such determination of the bounds of the events may be performed by detection algorithms executed by a processor. Block 991 represents this choice between physician marked events and algorithm marked events. In the physician marking embodiment, the loop recording stored data must be uplinked to an external device such as a programmer or other computer. Upon uplinking the loop recording stored data, the physician may score the onset, offset or other reference points in the brain signal at block 976. The physician may also classify the events as related or not to the particular neurological event being targeted. A matching test (brain detections versus cardiac or respiratory detections) is executed at block 977. The brain inputs to the matching test may be either physician markings (e.g., onset, offset of neurological event) or the automated scores from the neurological event detection algorithm. The matching test results from block 977 result in a summary of comparisons made between the brain and cardiac detections (or between the brain and respiratory detections). At block 978 the matching test results are evaluated. The evaluation at block 978 includes blocks 979, 980 and 981 (i.e., blocks 979, 980 and 981 are components of block 978. At block 979 concordance between brain and cardiac/respiratory detections is determined. At block 980 a cardiac or respiratory false positive rate (relative to the neurological signal) is evaluated using the cardiac un-matched events or the respiratory un-matched events in the cardiac or respiratory signals. At block 981 cardiac/respiratory latency is evaluated for the matched detections. At block 982, neurological event detection improvement using cardiac or respiration signals is considered based upon the above determinations. If use of cardiac signals or respiratory signals does not improve neurological event detection ("NO" condition), then the physician or other user may maintain or disable the cardiac event detection algorithm monitoring at block 983. If at block 982 the result is YES, the cardiac or respiratory signal is activated for neurological event monitoring or treatment.

Process 871 in FIG. 40B is one specific embodiment of process 971 in FIG. 40A. Process 871 is a process for determining whether to enable the ECG or respiratory detection algorithms for seizure detection. At block 874 the full monitor monitors EEG and ECG or respiratory signals. At block 875 detections in any of the 3 signals (EEG, ECG or respiratory) triggers loop recording. Determination of the bounds of the seizure, ECG and respiratory events may be performed in various ways. In one embodiment this determination of the bounds of a seizure may be performed by a physician. In another embodiment, such determination of the bounds of the events may be performed by detection algorithms executed by a processor. Block 891 represents this choice between physician marked events and algorithm marked events. In the physician marking embodiment, the loop recording stored data must be uplinked to an external device such as a programmer or other computer. Upon uplinking the loop recording stored data, the physician may score the onset, offset or other reference points in the EEG signal at block 876. The physician may also classify the events as seizure related or not. A matching test (EEG detections versus ECG or respiratory detections) is executed at block 877. The EEG inputs to the matching test may be either physician scores (e.g., onset, offset of seizure) or the automated scores from the neurological event detection algorithm. The matching test results from block 877 result in a summary of comparisons made between the EEG and ECG detections (or between the EEG and respiratory detections). At block 878 the matching test results are evaluated. The evaluation at block 878 includes blocks 879, 880 and 881 (i.e., blocks 879, 880 and 881 are components of block 878. At block 879 concordance between EEG and ECG/respiratory detections is determined. At block 880 an ECG false positive rate (relative to the neurological signal) is evaluated using the un-matched events in the ECG or respiratory signals. At block 881 ECG/respiratory latency is evaluated for the matched detections. At block 882, seizure detection improvement using ECG or respiration signals is considered based upon the above determinations. If use of ECG signals or respiratory signals does not improve seizure detection ("NO" condition), then the physician or other user may maintain or disable the ECG algorithm monitoring at block 883. The monitor begins monitoring or treatment at block 885. If at block 882 the result is YES, the ECG or respiratory signal is activated for seizure monitoring.

Monitor+Treatment (Brain)

FIG. 41 is a block diagram of the electronic circuitry that makes up full Monitor/Brain Therapy device 300 (FIG. 11) in accordance with the presently disclosed alternative embodiment of the invention. As can be seen from FIG. 41, Monitor/Brian Therapy device 300 comprises a primary control circuit 720 that is described herein above in conjunction with FIG. 26. In addition the Monitor/Brain Therapy device 300 of FIG. 41 also includes an amplifier 725 to amplify and sense EEG signals from a cranially implanted lead (one embodiment of a brain monitoring element 18) and a therapy module for providing therapy to the brain. The therapy module may be a drug delivery pump or an electrical stimulator or a brain cooling mechanism or other components depending on the treatment modality. In the embodiment of FIG. 41, the therapy module is an output stimulator 729 for stimulation of the brain. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via a brain lead that may be the same as monitoring element 18, formats and stores diagnostic data for later retrieval by the patient's clinician and, optionally, may warn or alert the patient, patient caregiver or remote monitoring location. See flow diagram and description as described below in association with FIG. 56.

FIG. 42 is a block diagram of the electronic circuitry that makes up full Monitor/Brain Therapy device 320 (FIG. 12A) in accordance with the presently disclosed alternative embodiment of the invention. As can be seen from FIG. 42, Monitor/Brain Therapy device 320 comprises a primary control circuit 720 and MV circuit 722 that are described herein above in conjunction with FIG. 28. In addition the Monitor/Brain Therapy device of FIG. 42 also includes an amplifier 725 to amplify and sense EEG signals from a cranially implanted monitoring element 18 and an output stimulator 729 to provide brain stimulation. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via a lead that may be the same as brain monitoring element 18, formats and stores diagnostic data for later retrieval by the patient's clinician and, optionally, may warn or alert the patient, patient caregiver or remote monitoring location. See flow diagram and description as described below in association with FIG. 56.

FIG. 43 is a block diagram of the electronic circuitry that makes up full Monitor/Brain Therapy device 321 (FIG. 12B) in accordance with the presently disclosed alternative embodiment of the invention. As can be seen from FIG. 43, Monitor/Brain Therapy device 321 in combination with a cranially implanted Monitor/Brain Therapy unit 26 in a patient 10 includes a primary control circuit 720 and MV circuit 722 that are described herein above in conjunction with FIG. 28. A 2-way wireless telemetry communication link 30 connects the Monitor/Therapy unit 26 and Monitor/Brain Therapy unit 321 via antennas 736. The wireless communication link 30 may consist of an RF link (such as described in U.S. Pat. No. 5,683,432 "Adaptive Performance-Optimizing Communication System for Communicating with an Implantable Medical Device" to Goedeke, et al, an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor/Brain Therapy unit 26 contains an amplifier 725 to amplify and sense EEG signals from a cranially implanted brain monitoring element 18 such as a lead and an output stimulator 729 for stimulation of the brain. Monitor 26 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing is accomplished by the use of integrated electrodes in the housing of monitor 26 or, alternatively, by a brain monitoring element 18 such as a cranially implanted leads.

Specifically, CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via a lead or other therapy delivery device (that could be the same as brain monitoring element 18), formats and stores diagnostic data for later retrieval by the patient's clinician and, optionally, may warn or alert the patient, patient caregiver or remote monitoring location. See flow diagram and description as described below in association with FIG. 56.

FIG. 44 is a block diagram of one embodiment of the electronic circuitry that makes up full Monitor/Brain Therapy device 340 with a brain monitoring element 18 (e.g., lead) and cardiac or respiratory monitoring element 14 such as sensor stub 20 (FIG. 13) in accordance with the presently disclosed alternative embodiment of the invention. As can be seen from FIG. 44, Monitor/Brain Therapy device 340 comprises a primary control circuit 720 and MV circuit 722 that were described herein above in conjunction with FIG. 28. In addition, the full Monitor/Brain Therapy device 340 of FIG. 44 also includes an amplifier 725 to amplify and sense EEG signals from a brain monitoring element 18 such as a cranially implanted lead. Additionally, the full Monitor/Brain Therapy device 340 of FIG. 44 also includes a stimulator 729 for providing stimulation to the brain through brain monitoring element 18 such as a cranially implanted lead. The CPU 732, in conjunction with a software program resident in RAM/ROM 730, integrates the information from the sensed cardiac, respiration and EEG signals, detects the onset of cerebral, cardiac or respiratory anomalies, provides preprogrammed stimulation therapy to the patient's brain via a therapeutic element such as brain monitoring element 18 which may be a lead, formats and stores diagnostic data for later retrieval by the patient's clinician and, optionally, may warn or alert the patient, patient caregiver or remote monitoring location. See flow diagram and description as described below in association with FIG. 56.

FIG. 45 is a block diagram of one embodiment of the electronic circuitry that makes up external patch 160/full Monitor/Brain Therapy device 360 with a brain monitoring element 18 that may be used for sensing and application of therapy (in the case of therapy being electrical stimulation) (FIG. 8) in accordance with the presently disclosed alternative embodiment of the invention. As can be seen from FIG. 45, Monitor/Brain Therapy device 360 comprises a primary control circuit 720 and external patch comprises a cardiac/MV (minute ventilation) circuit 160, the functions of which have been described in detail above in conjunction with the system of FIG. 28. Intrinsic cardiac signals are sensed by electrodes affixed to the patient's skin, amplified by amplifier 724, sent to primary control circuit 720 and processed by CPU 732 and software program resident in RAM/ROM 730. Cardiac anomalies are detected such as heart rate variability, QT variability, $QT_C$, sinus arrest, and various arrhythmias such as sinus, atrial and ventricular tachycardias. Respiration sensing is accomplished by low pass filtering the sensed and amplified intrinsic cardiac signals as shown in FIG. 27 or, alternatively, by using the MV/Z measurement circuitry of external patch 160 as described above in connection with FIG. 28. Respiration anomalies (such as reduced or cessation of tidal volume and apnea) are evaluated and detected by CPU 732 and software resident in RAM/ROM 730.

The CPU 732, in conjunction with a software program resident in RAM/ROM 730, integrates the information from the sensed cardiac, respiration and EEG signals, detects the onset of cerebral, cardiac or respiratory anomalies, provides preprogrammed stimulation therapy to the patient's brain via lead 18, formats and stores diagnostic data for later retrieval by the patient's clinician and, optionally, may warn or alert the patient, patient caregiver or remote monitoring location. See flow diagram and description as described below in association with FIG. 56.

The circuitry and function of the device 340 shown in FIG. 44 and described herein above may also be used for the full Monitor/Brain Therapy device 380 with integrated electrode 24 brain lead 18 (FIG. 15). As described above in association with core Monitor 340, thoracic impedance via impedance/voltage converter as measured from the case of monitor 340 to the integrated electrode 24 using a sampling frequency of approximately 16 Hz as substantially described in U.S. Pat. No. 4,596,251 "Minute Ventilation Dependant Rate Responsive Pacer" to Plicchi, et al. The Monitor 380 of this alternative embodiment utilizes the same circuitry of Monitor 340 but connected to the integrated electrode 24 on brain lead 18 instead of the sensor stub of Monitor 340.

Upon detection of either/or a cardiac or respiration anomaly, CPU 732, under control of firmware resident in RAM/ROM 730, will initiate recording of the appropriate diagnostic information into RAM of RAM/ROM 730, provides preprogrammed stimulation therapy to the patient's brain via lead 18, formats and stores diagnostic data for later retrieval by the patient's clinician and, optionally, may warn or alert the patient, patient caregiver or remote monitoring location. See flow diagram and description as described below in association with FIG. 56.

FIG. 46 is a block diagram of the electronic circuitry that makes up full Monitor/Brain Therapy device 400 (FIG. 20) in accordance with the presently disclosed alternative embodiment of the invention. As can be seen from FIG. 46, Monitor/Brian Therapy device 400 comprises a primary control circuit 720 (sensing cardiac and respiration parameters) that is described herein above in conjunction with FIG. 26. In addition the Monitor/Brain Therapy device 400 connects via a 2-way wireless communication link 30 to a cranially implanted EEG sensor and brain stimulator 26. EEG sensor and brain stimulator 26 contains an amplifier 725 to amplify and sense EEG signals from a cranially implanted lead 18 and an output stimulator 729 for stimulation of the brain. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18, formats and stores diagnostic data for later retrieval by the patient's clinician and, optionally, may warn or alert the patient, patient caregiver or remote monitoring location. See flow diagram and description as described below in association with FIG. 56.

FIG. 47 is a block diagram of the electronic circuitry that makes up full Monitor/Brain Therapy device 420 (FIG. 21) in accordance with the presently disclosed alternative embodiment of the invention. As can be seen from FIG. 47, Monitor/Brian Therapy device 420 comprises a primary control circuit 720 (sensing cardiac and respiration parameters) that is configured as an external patch affixed to a patient and whose function is described herein above in conjunction with FIG. 26. In addition, the Monitor/Brain Therapy device 420 comprises to a cranially implanted EEG sensor and brain stimulator 26 connected to the primary control circuit 720 via a 2-way wireless communication link 30. The wireless communication link 30 may consist of an RF link (such as described in U.S. Pat. No. 5,683,432 "Adaptive Performance-Optimizing Communication System for Communicating with an Implantable Medical Device" to Goedeke, et al.), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). EEG sensor and brain stimulator 26 contains an amplifier 725 to amplify and sense EEG signals from a cranially implanted lead 18 and an output stimulator 729 for stimulation of the brain. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18, formats and stores diagnostic data for later retrieval by the patient's clinician and, optionally, may warn or alert the patient, patient caregiver or remote monitoring location. See flow diagram and description as described below in association with FIG. 56.

Monitor+Treatment (Brain+Respiration)

FIG. 48 is a block diagram of the electronic circuitry that makes up full Monitor/Brain and Respiration Therapy device 440 (FIG. 16A) in accordance with the presently disclosed alternative embodiment of the invention. As can be seen from FIG. 48, Monitor/Brain and Respiration Therapy device 440 comprises a primary control circuit 720 and MV circuit 722 whose function was described herein above in conjunction with FIG. 28. In addition the Monitor/Brain and Respiration Therapy device of FIG. 48 also includes an amplifier 725 to amplify and sense EEG signals from a cranially implanted lead 18 and an output stimulator 729 to provide brain stimulation via cranially implanted lead 18 and phrenic nerve stimulation via respiration lead 28. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and stimulation of the patient's phrenic nerve via respiration lead 28, formats and stores diagnostic data for later retrieval by the patient's clinician and, optionally, may warn or alert the patient, patient caregiver or remote monitoring location. Optionally, lead 28 may connect to the diaphragm to provide direct diaphragmatic stimulation. See flow diagram and description as described below in association with FIG. 56.

FIG. 49 is a block diagram of the electronic circuitry that makes up full Monitor/Brain and Respiration Therapy device 441 (FIG. 16B) in accordance with the presently disclosed alternative embodiment of the invention. As can be seen from FIG. 49, Monitor/Brain and Respiration Therapy device 441 in combination with a cranially implanted Monitor/Brain Therapy unit 26 in a patient 10 includes a primary control circuit 720 and MV circuit 722 that are described herein above in conjunction with FIG. 28. A 2-way wireless telemetry communication link 30 connects the Monitor/Therapy unit 26 and Monitor/Brain and Respiration Therapy unit 441 via antennas 736. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor/Brain Therapy unit 26 contains an amplifier 725 to amplify and sense EEG signals from a cranially implanted lead 18 and an output stimulator 729 for stimulation of the brain. Monitor 26 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads 18.

Specifically, CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and to the phrenic nerve via respiration lead 28, formats and stores diagnostic data for later retrieval by the patient's clinician and, optionally, may warn or alert the patient, patient caregiver or remote monitoring location. Optionally, lead 28 may connect to the diaphragm to provide direct diaphragmatic stimulation. See flow diagram and description as described below in association with FIG. 56.

FIG. 50 is a block diagram of the electronic circuitry that makes up full Monitor/Brain and Respiration Therapy device 460 with a brain lead 18, phrenic nerve lead 28 and sensor stub 20 (FIG. 17) in accordance with the presently disclosed alternative embodiment of the invention. As can be seen from FIG. 50, Monitor/Brain and Respiration Therapy device 460 comprises a primary control circuit 720 and MV circuit 722 whose function was described herein above in conjunction with FIG. 28. In addition, the full Monitor/Brain and Respiration Therapy device 460 of FIG. 50 also includes an amplifier 725 to amplify and sense EEG signals from a cranially implanted lead 18. Additionally, the full Monitor/Brain Therapy device 340 of FIG. 44 also includes a stimulator 729 for providing stimulation to the brain through cranially implanted lead 18 and phrenic nerve stimulation via respiration lead 28. The CPU 732, in conjunction with a software program resident in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and stimulation of the patient's phrenic nerve via respiration lead 28, formats and stores diagnostic data for later retrieval by the patient's clinician and, optionally, may warn or alert the patient, patient caregiver or remote monitoring location. See flow diagram and description as described below in association with FIG. 56.

The circuitry and function of the device 460 shown in FIG. 50 and described herein above may also be used for the full Monitor/Brain and Respiration Therapy device 480 with integrated electrode 24 brain lead 18 and phrenic nerve lead 28 (FIG. 18). As described above in association with Monitor/Brain and Respiration Therapy device 460, thoracic impedance via impedance/voltage converter as measured from the case of monitor 480 to the integrated electrode 24 using a sampling frequency of approximately 16 Hz as substantially described in U.S. Pat. No. 4,596,251 "Minute Ventilation Dependant Rate Responsive Pacer" to Plicchi, et al. The Monitor/Brain and Respiration Therapy device 480 of this alternative embodiment utilizes the same circuitry of Monitor/Brain and Respiration Therapy device 460 but connected to the integrated electrode 24 on brain lead 18 instead of the sensor stub 20 of Monitor/Brain and Respiration Therapy device 340.

Upon detection of either/or a cardiac or respiration anomaly, CPU 732, under control of firmware resident in RAM/ROM 730, will initiate recording of the appropriate diagnostic information into RAM of RAM/ROM 730, provides preprogrammed stimulation therapy to the patient's brain via lead 18 and stimulation of the patient's phrenic nerve via respiration lead 28, formats and stores diagnostic data for later retrieval by the patient's clinician and, optionally, may warn or alert the patient, patient caregiver or remote monitoring location. See flow diagram and description as described below in association with FIG. 56.

The circuitry and function of the device 460 shown in FIG. 50 and described herein above may also be used for the full Monitor/Brain and Respiration Therapy device 500 with brain lead 18 and integrated electrode 24 phrenic nerve lead 28 (FIG. 19). As described above in association with Monitor/Brain and Respiration Therapy device 460, thoracic impedance via impedance/voltage converter as measured from the case of monitor 500 to the integrated electrode 24 using a sampling frequency of approximately 16 Hz as substantially described in U.S. Pat. No. 4,596,251 "Minute Ventilation Dependant Rate Responsive Pacer" to Plicchi, et al. The Monitor/Brain and Respiration Therapy device 500 of this alternative embodiment utilizes the same circuitry of Monitor/Brain and Respiration Therapy device 460 but connected to the integrated electrode 24 on phrenic nerve lead 28 instead of the sensor stub 20 of Monitor/Brain and Respiration Therapy device 340.

Upon detection of either/or a cardiac or respiration anomaly, CPU 732, under control of firmware resident in RAM/ROM 730, will initiate recording of the appropriate diagnostic information into RAM of RAM/ROM 730, provides preprogrammed stimulation therapy to the patient's brain via lead 18 and stimulation of the patient's phrenic nerve via respiration lead 28, formats and stores diagnostic data for later retrieval by the patient's clinician and, optionally, may warn or alert the patient, patient caregiver or remote monitoring location. See flow diagram and description as described below in association with FIG. 56.

Monitor+Treatment (Brain+Cardiac)

FIG. 51 is a block diagram of the electronic circuitry that makes up full Monitor/Brain and Cardiac Therapy device 520 (FIG. 24A) in accordance with the presently disclosed alternative embodiment of the invention. As can be seen from FIG. 51, Monitor/Brain and Cardiac Therapy device 520 comprises a primary control circuit 720 and MV circuit 722 whose function is described herein above in conjunction with FIG. 28 and U.S. Pat. No. 5,271,395 "Method and Apparatus for Rate Responsive Cardiac Pacing" to Wahlstrand et al. In addition, the Monitor/Brain and Cardiac Therapy device of FIG. 51 also includes an amplifier 725 to amplify and sense EEG signals from a cranially implanted lead 18 and an output stimulator 729 to provide brain stimulation. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and stimulation to the patient's heart via cardiac lead(s) 16, formats and stores diagnostic data for later retrieval by the patient's clinician and, optionally, may warn or alert the patient, patient caregiver or remote monitoring location. See flow diagram and description as described below in association with FIG. 54.

FIG. 52 is a block diagram of the electronic circuitry that makes up full Monitor/Brain and Cardiac Therapy device 521 (FIG. 24B) in accordance with the presently disclosed alternative embodiment of the invention. As can be seen from FIG. 52, Monitor/Brain and Cardiac Therapy device 521 in combination with a cranially implanted Monitor/Brain Therapy unit 26 in a patient 10 includes a primary control circuit 720 and MV circuit 722 that are described herein above in conjunction with FIG. 28. A 2-way wireless telemetry communication link 30 connects the Monitor/Therapy unit 26 and Monitor/Brain and Cardiac Therapy unit 521 via antennas 736. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859

"Acoustic Body Bus Medical Device Communication System" to Funke). Monitor/Brain Therapy unit 26 contains an amplifier 725 to amplify and sense EEG signals from a cranially implanted lead 18 and an output stimulator 729 for stimulation of the brain. Monitor 26 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads 18.

Specifically, CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and cardiac stimulation via cardiac leads 16, formats and stores diagnostic data for later retrieval by the patient's clinician and, optionally, may warn or alert the patient, patient caregiver or remote monitoring location. See flow diagram and description as described below in association with FIG. 56.

Alternatively, the device as described above in connection to the Monitor and Treatment (Brain and Cardiac) system of FIG. 52 may include a pacemaker/cardioverter/defibrillator (PCD) to enable the termination of cardiac arrhythmias during, or prior to, neurological events. The PCD may be of the type as substantially described in U.S. Pat. No. 5,545,186 "Prioritized Rule Based Method and Apparatus for Diagnosis and Treatment of Arrhythmias" to Olson; U.S. Pat. No. 5,354,316 "Method and Apparatus for Detection and Treatment of Tachycardia and fibrillation" to Kiemel or U.S. Pat. No. 5,314,430 "Atrial Defibrillator Employing Transvenous and Subcutaneous Electrodes and Method of Use" to Bardy. In one embodiment of the present invention, the PCD arrhythmia detection circuitry/algorithms are enabled upon the sensing of the onset or impending onset of a seizure. Upon seizure termination, the arrhythmia detection circuitry/algorithms are turned off.

FIG. 53 is a block diagram of the electronic circuitry that makes up full Monitor/Brain and Cardiac Therapy device 540 (FIG. 22) in accordance with the presently disclosed alternative embodiment of the invention. The system as shown in FIG. 53 is used for patients temporarily at risk of sudden death, for example, while the patient's physician is trying different epileptic drugs and titrating dosages to eliminate/minimize seizures or their severity. As can be seen from FIG. 53, Monitor/Brain and Cardiac Therapy device 540 comprises patient worn vest defibrillator 34 containing primary control circuit 720 whose function is described herein above in conjunction with FIG. 26 and in more detail in U.S. Pat. No. 6,280,461 "Patient-Worn Energy Delivery Apparatus'" to Glegyak, et. In addition the Monitor/Brain and Cardiac Therapy device connects via a 2-way wireless communication link 30 to a cranially implanted brain stimulator 540. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). EEG sensor and brain stimulator 540 contains an amplifier 725 to amplify and sense EEG signals from a cranially implanted lead 18 and an output stimulator 729. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and defibrillation therapy via patient worn vest 34, formats and stores diagnostic data for later retrieval by the patient's clinician and, optionally, may warn or alert the patient, patient caregiver or remote monitoring location. See flow diagram and description as described below in association with FIG. 56.

The circuitry and function of the device 540 shown in FIG. 53 and described herein above may also be used for the full Monitor/Brain and Cardiac Therapy device 560 with a cranially implanted stimulator in 2-way communication with an leadless subcutaneous implantable defibrillator 36 (ie, "lifeboat", FIG. 23). The system described in connection with this embodiment is used for patients temporarily at risk of sudden death, for example, while the patient's physician is trying different epileptic drugs and titrating dosages to eliminate/minimize seizures or their severity. As described above in conjunction with FIG. 53, Monitor/Brian and Cardiac Therapy device 560 comprises a leadless defibrillator 36 containing primary control circuit 720 whose function is described herein above in conjunction with FIG. 26 and in more detail in U.S. Pat. No. 6,647,292 "Unitary Subcutaneous only Implantable Cardioverter-Defibrillator and Optional Pacer" to Bardy.

The Monitor/Brain and Cardiac Therapy device connects via a 2-way wireless communication link 30 to a cranially implanted brain stimulator 560. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). EEG sensor and brain stimulator 560 contains an amplifier 725 to amplify and sense EEG signals from a cranially implanted lead 18 and an output stimulator 729. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18 and defibrillation therapy via implanted defibrillator 36, formats and stores diagnostic data for later retrieval by the patient's clinician and, optionally, may warn or alert the patient, patient caregiver or remote monitoring location. See flow diagram and description as described below in association with FIG. 56.

Monitor+Treatment (Brain+Respiration+Cardiac)

FIG. 54 is a block diagram of the electronic circuitry that makes up full Monitor/Brain, Respiration and Cardiac Therapy device 580 (FIG. 25A) in accordance with the presently disclosed alternative embodiment of the invention. As can be seen from FIG. 54, Monitor/Brain, Respiration and Cardiac Therapy device 580 comprises a primary control circuit 720 and MV circuit 722 whose function was described herein above in conjunction with FIG. 28. In addition the Monitor/Brain, Respiration and Cardiac Therapy device of FIG. 54 also includes an amplifier 725 to amplify and sense EEG signals from a cranially implanted lead 18 and an output stimulator 729 to provide brain stimulation via cranially implanted lead 18 and phrenic nerve stimulation via respiration lead 28. The CPU 732, in conjunction with software program in RAM/ROM 730, integrates the information from the sensed cardiac, respiration and EEG signals, detects the onset of cerebral, cardiac or respiratory anomalies, provides preprogrammed stimulation therapy to the patient's brain via lead 18, stimulation of the patient's phrenic nerve via respiration lead 28 and stimulation of the patient's heart via cardiac leads 16, formats and stores diagnostic data for later retrieval by the patient's clinician and, optionally, may warn or alert the patient, patient caregiver or remote monitoring location. Optionally, lead 28 may connect to the diaphragm to provide direct diaphragmatic stimulation. See flow diagram and description as described below in association with FIG. 56.

FIG. 55 is a block diagram of the electronic circuitry that makes up full Monitor/Brain, Respiration and Cardiac Therapy device 581 (FIG. 25B) in accordance with the presently disclosed alternative embodiment of the invention. As can be seen from FIG. 55, Monitor/Brain, Respiration and Cardiac Therapy device 581 in combination with a cranially implanted Monitor/Brain Therapy unit 26 in a patient 10 includes a primary control circuit 720 and MV circuit 722 that are described herein above in conjunction with FIG. 28. A 2-way wireless telemetry communication link 30 connects the Monitor/Therapy unit 26 and Monitor/Brain, Respiration and Cardiac Therapy unit 581 via antennas 736. The wireless communication link 30 may consist of an RF link (such as described in U.S. Pat. No. 5,683,432 "Adaptive Performance-Optimizing Communication System for Communicating with an Implantable Medical Device" to Goedeke, et al), an electromagnetic/ionic transmission (such as described in U.S. Pat. No. 4,987,897 "Body Bus Medical Device Communication System" to Funke) or acoustic transmission (such as described in U.S. Pat. No. 5,113,859 "Acoustic Body Bus Medical Device Communication System" to Funke). Monitor/Brain Therapy unit 26 contains an amplifier 725 to amplify and sense EEG signals from a cranially implanted lead 18 and an output stimulator 729 for stimulation of the brain. Monitor 26 may be constructed as substantially described in US Publication No. 20040176817 "Modular implantable medical device" to Wahlstrand et al. or U.S. Pat. Nos. 5,782,891 "Implantable Ceramic Enclosure for Pacing, Neurological and Other Medical Applications in the Human Body" to Hassler, et al or 6,427,086 "Means and Method for the Intracranial Placement of a Neurostimulator" to Fischell. et al. EEG sensing is accomplished by the use of integrated electrodes in the housing of monitor 26 or, alternatively, by cranially implanted leads 18.

Specifically, CPU 732, in conjunction with software program in RAM/ROM 730, integrates the information from the sensed cardiac, respiration and EEG signals, detects the onset of cerebral, cardiac or respiratory anomalies, provides pre-programmed stimulation therapy to the patient's brain via lead 18, to the phrenic nerve via respiration lead 28 and to the heart via cardiac leads 16, formats and stores diagnostic data for later retrieval by the patient's clinician and, optionally, may warn or alert the patient, patient caregiver or remote monitoring location. Optionally, lead 28 may connect to the diaphragm to provide direct diaphragmatic stimulation. See flow diagram and description as described below in association with FIG. 56.

FIG. 56 is a flow diagram 850 showing operation of a full monitor/therapy sensing and monitoring cardiac, respiration and electroencephalogram parameters for the detection of neurological events as shown and described in embodiments in FIG. 11-25 above. The blocks 802-808 relating to the identification of cardiac activity, and blocks 816-822 relating to identification of respiratory activity, may be activated or deactivated according to the determination of whether they improve the detection of the neurological disorder (see for example the discussion regarding determining concordance). It is noted that the particular detection scheme used for each of the physiologic signals (brain, heart, respiratory) is not restricted to the examples provided here.

In one embodiment, beginning at block 802, the interval between sensed cardiac signals are measured. At block 804, a rate stability measurement is made on each cardiac interval utilizing a heart rate average from block 806. At block 808, a rate stable decision is made based upon preprogrammed parameters. If YES (heart rate is determined to be stable), the flow diagram returns to the HR Measurement block 802. If NO, the rate stability information is provided to Determine Therapy and Duration block 830.

At block 816, thoracic impedance is continuously measured in a sampling operation. At block 818, a MV and respiration rate calculation is made. At block 822, a pulmonary apnea decision is made based upon preprogrammed criteria. If NO (no apnea detected), the flow diagram returns to MV Measurement block 816. If YES, the occurrence of apnea and MV information is provided to Determine Therapy and Duration block 830.

At block 824, the electroencephalogram is sensed and measured. An EEG calculation is performed at block 826. The seizure detection algorithm is executed at block 826. At block 828, a seizure episode is determined. If NO (no seizure detected), the flow diagram returns to EEG Measurement block 824. If YES, the occurrence of a seizure is provided to Determine Therapy and Duration block 830.

Based upon the data presented to it, Determine Therapy and Duration block 830 determines the type of therapy and the duration to block 832, which controls the start of the therapy by evaluating the severity and ranking of each event (i.e., maximum ratio, duration of seizure detection, spread, number of clusters per unit time, number of detections per cluster, duration of an event cluster, duration of a detection, and inter-seizure interval) per co-pending U.S. patent application Publication No. 20040133119 "Scoring of sensed neurological signals for use with a medical device system" to Osorio, et al incorporated herein by reference in its entirety. Block 834 monitors the completion of the determined therapy. If the therapy is not complete, control returns to block 834. If the therapy is determined to be complete, block 834 returns the flow diagram to blocks 802 (Measure HR), 816 (Measure Impedance) and 824 (Measure EEG) to continue the monitoring of cardiac, respiratory and brain signal parameters.

Therapy may consist of neural stimulation, cardiac pacing, cardioversion/defibrillation, and drug delivery via a pump, brain cooling, or any combination of therapies.

When block 830 determines that a therapy is to be initiated Format Diagnostic Data block 812 formats the data from the cardiac, respiration and EEG monitoring channels, adds a time stamp (ie, date and time), type and duration of therapy and provides the data to block 814 where the data is stored in RAM memory for later retrieval by a clinician via telemetry. Optionally, block 812 may add examples of intrinsic ECG, respiration or EEG signals recorded during a sensed episode/seizure.

The physician may program the devices shown above in relation to FIGS. 11-25 and 41-55 to allow the ECG/respiratory detectors be enabled to trigger the delivery of therapy (i.e., stimulation or drug delivery) to the patient's brain, with goal of aborting seizures earlier or limiting their severity than if using EEG signal detection alone. Either EEG, respiratory or ECG detections may trigger therapy to the brain, depending on which occurs first. The physician may choose the type of ECG or respiratory event to use for triggering therapy to the brain.

Application of Therapy to the Brain Based on Cardiac or Respiratory Signals and Termination of Such Therapy In the present invention of the devices shown above in relation to FIGS. 11-25 and 41-55, the device is able to terminate or change the cardiac/respiratory initiated treatment, directed at the brain, if a neurological event is not entered within an expected time frame following cardiac detection. This feature allows the device to begin treating a patient's neurological event before its detection in the brain signal. These termination conditions are defined at block 990 of FIGS. 40A and 890 of FIG. 40B.

If the cardiac/respiratory initiated brain therapy has been ongoing for some time, and polling of the brain signal (i.e., processing the brain signal with a neurological event detection algorithm) has indicated the patient is not in a neurological event, then the following may be true:
1. Cardiac/respiratory triggered therapy was successful in aborting the neurological event, and therefore, the neurological event is not detectable in the brain signal.
2. The cardiac/respiratory event was not associated with a neurological event.

In either case, it would be appropriate to change (adjust or terminate) cardiac/respiratory initiated therapy directed specifically at aborting a neurological event. FIG. 57A is a flow chart illustrating the processing steps executed by a processor (e.g., CPU 732 or any other processor). At block 1000 the processor monitors the cardiac or respiratory signals. At block 1002, the processor detects a cardiac or respiratory event in the cardiac or respiratory signals. Based upon a cardiac or respiratory event detection at block 1002, the processor activates the therapy module to provide therapy to the brain at block 1004. The brain signal is monitored at block 1006. This may be a continuation of monitoring of the brain that was already ongoing or it may be initiation of brain monitoring. Once the therapy has been initiated from a cardiac or respiratory detection, the therapy may be changed at block 1008 based on the monitoring of the brain signal.

One embodiment of the process of FIG. 57A is illustrated in FIG. 57B. The processor receives the cardiac or respiratory signals at block 1050. A cardiac or respiratory event is detected at block 1052. The therapy module is activated at block 1054 to provide therapy to the brain based on a cardiac or respiratory detection. Once therapy has been initiated from a cardiac/respiratory detection, the device monitors the amount of time therapy has been delivered at block 1056. This time period is programmable. The processor continues to receive a brain signal at block 1058. At decision block 1060 the processor determines when the programmed time period has been exceeded without detection of a neurological event in the brain signal. If the answer is "Yes" (i.e., the cardiac or respiratory initiated brain therapy has been ongoing for the programmed time period without the occurrence of a neurological event in the brain signal), then therapy to the brain is discontinued at block 1062. If the patient has entered a neurological event while receiving cardiac/respiratory initiated therapy, control of therapy is transferred to the monitoring of the brain by the neurological event detection algorithm, and therapy decisions are made using the brain signals at block 1064. At this point therapy may continue until the EEG detection algorithm determines that the neurological event has ended. Then therapy may be terminated based on the detected end of the neurological event based on the EEG detection algorithm output.

FIG. 40A discussed above shows a process 971 for determining whether to enable the cardiac or respiratory detectors for neurological event detection and treatment. Once the cardiac or respiratory signals have been enabled for neurological event detection monitoring and treatment at block 986 and the neurological event detection algorithm has been enabled for modulation or other input into cardiac or respiratory therapy, the cardiac/respiratory parameters for ictal/post-ictal treatment options are defined at block 987. At block 988, cardiac/respiratory events to treat when in a neurological state are defined. At block 989, cardiac/respiratory events to treat when outside a neurological event are defined. At block 990, therapy termination conditions (i.e., turn over control of brain therapy to the neurological event detection algorithm and terminate if a neurological event is not entered in a programmable period of time) are defined and the monitor starts monitoring or treatment at 985.

If the matching test of the flow diagram of FIG. 40A shows that one type of cardiac event (type 1) is associated with neurological event onset while other types of cardiac events (type 2) occur frequently, but have no temporal relationship to the neurological event, then the physician may chose to direct therapy to the Brain (or Brain and Heart) upon type 1 event detection or direct therapy to the Heart on type 2 detection.

In the present invention as described in relation to the devices shown above in FIGS. 11-25 and 41-55, the physician is able to selectively choose which cardiac and respiratory events to treat in seizure and non-seizure states. For example, the device may be programmed to treat incidences of tachycardia in non-seizure states, but not in seizure states, where this type of cardiac behavior is expected and considered normal. Also, the patient may experience certain ECG or respiratory abnormalities, which are seizure induced, but cause no complications or increased health risk to the patient. In such cases, the physician may decide to suppress treatment for these events if detected during a seizure. This cannot be accomplished with existing pacemaker technology, which operates on ECG signals only.

There are other instances in which a detected ECG or respiratory abnormality does pose a health risk, regardless of when it occurs and how it was induced. For these events, the physician may choose a mode of operation that treats the ECG/respiratory abnormality in both seizure and non-seizure states (i.e., asystole, apnea).

Additionally, the physician may choose to treat the same ECG/respiratory event in both seizure and non-seizure states, but may define different thresholds (i.e., duration or intensity) for treating the event. For example, during a seizure state, a higher heart rate or sustained occurrence of tachycardia may be required before cardiac treatment is initiated, relative to a non-seizure state. This feature would enable cardiac therapy during status epilepticus, which is a prolonged condition, but suppress it for typical seizure behaviors.

If the matching test of the flow diagram of FIG. 57 shows that the ECG or respiratory signals do not improve seizure detection, but patient is at cardiac risk, the physician may choose to enable the ECG/respiratory detector to deliver therapy to the heart or diaphragm.

If the matching test of the flow diagram of FIG. 57 shows that the ECG or respiratory signals improves seizure detection, but the patient is also at cardiac risk, the physician may choose to treat the brain (for seizures) with EEG, ECG or respiratory detection, and heart (for cardiac problems) with ECG detection.

Preventative Pacing Therapy

Optionally, the therapy systems of FIGS. 11-25 and 41-55 may also have pre-emptive or preventative pacing capabilities. For example, upon EEG detection of seizure onset or imminent seizure onset, the pacing systems described in conjunction with FIGS. 11-25 and 41-55 may begin preventative overdrive pacing to prevent or mitigate sleep apnea such as described in U.S. Pat. No. 6,126,611 "Apparatus for Management of Sleep Apnea" to Bourgeois. The '611 patent detects sleep apnea and begins to pace the heart at a rate of 70-100 PPM (overdrive pacing the sleep intrinsic rate of typically 30-55 BPM) causing arousal and elimination/prevention of sleep apnea. The herein described invention uses the detection of the onset or impending onset of a seizure to trigger sleep apnea overdrive pacing to preemptively prevent the initiation of apnea. Upon the sensing of seizure termination or a preprogrammed timeout, the sleep apnea prevention overdrive pacing is terminated/inactivated.

Alternatively, the pacing systems may begin ventricular pacing overdrive upon sensing a ventricular premature contraction to prevent the initiation of ventricular arrhythmias such as described in U.S. Pat. No. 4,503,857 "Programmable Cardiac Pacemaker with Microprocessor Control of Pacer Rate" to Boute, et al and 5,312,451 "Apparatus and Methods for Controlling a Cardiac Pacemaker in the Event of a Ventricular Extrasystole" to Limousin, et al. Upon detection of the onset or impending onset of a seizure ventricular extrasystole overdrive pacing may be initiated, and subsequent to the programmed number of cycles, a slowing of the ventricular rate until either the programmed base rate is reached or a sinus detection occurs. Upon the sensing of seizure termination or a preprogrammed timeout, the sleep apnea prevention overdrive pacing is terminated/inactivated.

Additionally, the pacing systems described in conjunction with FIGS. 11-25 and 41-55 may include AF preventative pacing therapies as described in U.S. Pat. No. 6,185,459 "Method and Apparatus for Prevention of Atrial Tachyarrhythmias" to Mehra, et al or 6,650,938 Method and System for Preventing Atrial Fibrillation by Rapid Pacing Intervention" to Boute. The '459 and '938 patents describe systems that sense premature atrial events and initiate overdrive pacing algorithms to prevent the initiation of atrial arrhythmias. In the present invention, upon detection of the onset or impending onset of a seizure, ventricular extrasystole AF overdrive pacing may be initiated, and subsequent to the programmed number of cycles, a slowing of the ventricular rate until either the programmed base rate is reached or a sinus detection occurs. Upon the sensing of seizure termination or a preprogrammed timeout, the sleep apnea prevention overdrive pacing is terminated/inactivated.

Signal Processing

The signal processing of cardiac, respiration or electroencephalogram signals of the above-described embodiments may include analog, continuous wave bandpass filtering as is well known in the art. Additionally, digital signal processing techniques as substantially described in U.S. Pat. No. 6,029,087 "Cardiac Pacing System with Improved Physiological Event Classification Based Upon DSP" to Wohlgemuth and 6,556,859 "System and Method for Classifying Sensed Atrial Events in a Cardiac Pacing System" to Wohlgemuth, et al may be used. Additionally, fuzzy logic processing techniques as described in U.S. Pat. No. 5,626,622 "Dual Sensor Rate Responsive Pacemaker" to Cooper and 5,836,988 "Rate Responsive Pacemaker with Exercise Recovery Using Minute Volume Determination" to Cooper, et al. may be used to determine/detect the occurrence or onset of seizures, respiratory or cardiac anomalies.

The devices of the above-described systems that contain 2 individual units in 2-way communication (e.g., the systems of FIG. 20-23) may optionally transmit events via the communication channel by one of several ways including, but not limited to, individual event logic signal, marker channel or processed signal.

Power Saving and Clock Synchronization

The devices of the above-described systems that contain 2 individual units in 2-way communication (e.g., the systems of FIG. 20-23, 43, 45-47, 49, 52, 53, 55) may optionally have a reduced power capability during communication. The devices may communicate at a predefined specific time interval with clocks in each unit of the system updated/resynchronized on each communication (as described in U.S. Pat. No. 6,083,248 "World Wide Patient Location and Data Telemetry System for Implantable Medical Devices" to Thompson. Optionally, a receiving unit may open a window at a period interval (e.g., 1 second) for a brief window (e.g., 100 mSec) to look for an incoming transmission from the other system unit.

Drug Pump

The therapy device in above devices as described in systems as described in conjunction with FIGS. 11-25 and 41-55 may optionally contain a drug pump to deliver liquid medicants in lieu of stimulation or in combination with stimulation. Medicants used could include epileptic drugs (examples of such drugs include, but are not limited to intrathecal delivery of CGX-1007 or Baclofen), mental health and mood disorder related drugs, cardiac drugs (examples of such drugs include, but are not limited to, pharmaceutical compositions comprising beta-adrenergic blocking agents, protain emide, type 1 antiarrhythmic agents such as disopyramide, class II agents such as propafenone, alphaagonists such as ephedrine and midodrine, and other antiarrhymic agents such as amiodarone, and combinations thereof) or respiratory drugs (examples of such drugs include, but are not limited to diuretics).

Remote Monitoring

The present invention also allows the residential, hospital or ambulatory monitoring of at-risk patients and their implanted medical devices at any time and anywhere in the world (see system 900 FIG. 58). Medical support staff 906 at a remote medical support center 914 may interrogate and read telemetry from the implanted medical device and reprogram its operation while the patient 10 is at very remote or even unknown locations anywhere in the world. Two-way voice communications 910 via satellite 904, cellular via link 32 or land lines 956 with the patient 10 and data/programming communications with the implanted medical device 958 via a belt worn transponder 960 may be initiated by the patient 10 or the medical support staff 906. The location of the patient 10 and the implanted medical device 958 may be determined via GPS 902 and link 908 and communicated to the medical support network in an emergency. Emergency response teams can be dispatched to the determined patient location with the necessary information to prepare for treatment and provide support after arrival on the scene. See for example, U.S. Pat. No. 5,752,976 "World Wide Patient Location and Data Telemetry System for Implantable Medical Devices" to Duffin et al.

An alternative or addition to the remote monitoring system as described above in conjunction with FIG. 58 is shown in the system 950 of FIG. 59, which shows a patient 10 sleeping with an implantable Monitor 958 or optional therapy device as described above in connection with the systems of FIG. 1-57. The implantable device 958, upon detection of a neurological event (such as a seizure), respiratory apnea or cardiac conduction anomaly (ie, heart rate variability, QT extension, arrhythmia) may alert a remote monitoring location via local remote box 952 (as described in U.S. Pat. No. 5,752,976 "World Wide Patient Location and Data Telemetry System for Implantable Medical Devices" to Duffin, et al.) telephone 954 and phone lines 956 or the patient's care provider via an RF link 32 to a pager-sized remote monitor 960 placed in other locations in the house or carried (ie, belt worn) by the care provider 962. The remote caregiver monitor 960 may include audible buzzes/tones/beeps, vocal, light or vibration to alert the caregiver 962 of patient's monitor in an alarm/alert condition. The RF link may include RF portable phone frequencies, power line RF links, HomeRF, Bluetooth, ZigBee, WIFI, MICS band (medical implant communications service), or any other interconnect methods as appropriate. Often the care provider 962 may be able to take some action to help the patient 10. For example, the care provider may arouse the patient 10 from a neurological event (such as a SUDEP episode) by shaking them, arousing them, reposition the patient, or the like.

Patient Alert

The monitor (and optionally therapy) devices as described in systems described above in conjunction with FIG. 1-57 may optionally allow a patient alert to allow the patient an early warning of impending seizure, respiratory or cardiac anomalies via vibration (e.g., piezo buzzer in implanted device, a vibrator as used in a cell phone or pager in a "silent ring" mode in vest, patch or patient activator), audible buzzing or tones (e.g., audible in cranial implant, audible via external patch, patient activator or vest), light (e.g., external vest or patient activator) or vocal (e.g., spoken word in cranial, vest, external patch, or patient activator) indicators of the monitor in an alarm/alert condition.

It will be apparent from the foregoing that while particular embodiments of the invention have been illustrated and described, various modifications can be made without departing from the spirit and scope of the invention. Accordingly, it is not intended that the invention be limited, except as by the appended claims.

What is claimed is:

1. A method for comparing a brain signal to a cardiac signal for use in detecting neurological events, the method comprising:
receiving a brain signal with a medical device system comprising processing circuitry for a period of time;
receiving a cardiac signal with the medical device system for a period of time;
obtaining information with the processing circuitry identifying one or more neurological events in the brain signal;
obtaining information with the processing circuitry identifying one or more cardiac events in the cardiac signal; and
comparing the brain signal and the cardiac signal with the processing circuitry to determine a temporal relationship between the one or more neurological events and the one or more cardiac events for determining whether neurological event detection is improved by using the cardiac signal, the comparing comprising
categorizing with the processing circuitry each of the identified neurological events as cardiac matched when there is a cardiac event within a specified time period of the neurological event; and
computing with the processing circuitry a rate of concordance between the neurological events and the cardiac events based on the number of cardiac matched events and the number of neurological events.

2. The method of claim 1, wherein computing the rate of concordance comprises determining with the processing circuitry the number of cardiac matched events divided by the number of neurological events.

3. The method of claim 1, wherein obtaining information identifying the one or more neurological events in the brain signal comprises applying with the processing circuitry a neurological event detection algorithm to the brain signal and wherein obtaining information identifying the one or more cardiac events in the cardiac signal comprises applying with the processing circuitry a cardiac event detection algorithm to the cardiac signal.

4. The method of claim 1, further comprising for each neurological event categorized as cardiac matched, determining with the processing circuitry the temporal order of the neurological event and the cardiac event that is within a specified time period of the neurological event.

5. The method of claim 4, further comprising categorizing with the processing circuitry each of the cardiac events as cardiac unmatched when there is no neurological event within a specified time period of the cardiac event.

6. The method of claim 5, wherein determining whether the neurological event detection is improved comprises considering the rate of concordance, the temporal order of the cardiac matched events, and the number of cardiac unmatched events.

7. The method of claim 4, further comprising activating with the processing circuitry a cardiac event detection algorithm for use in neurological event detection based on a determination that the neurological event detection is improved by using the cardiac signal.

8. The method of claim 7, wherein the neurological event to be detected by the cardiac event detection algorithm is a seizure.

9. A method for comparing a brain signal to a cardiac signal for use in detecting neurological events, the method comprising:
receiving a brain signal with a medical device system comprising processing circuitry for a period of time;
receiving a cardiac signal with the medical device system for a period of time;
obtaining information with the processing circuitry identifying one or more neurological events in the brain signal;
obtaining information with the processing circuitry identifying one or more cardiac events in the cardiac signal; and
comparing the brain signal and the cardiac signal with the processing circuitry to determine a temporal relationship between the one or more neurological events and the one or more cardiac events for determining whether neurological event detection is improved by using the cardiac signal,
wherein the comparing the brain signal and the cardiac signal further comprises:
obtaining information categorizing each cardiac event as one or more of a first type cardiac event and a second type cardiac event
categorizing with the processing circuitry the neurological event as first type cardiac matched when there is a first type cardiac event within a specified time period of the neurological event;
categorizing with the processing circuitry the neurological event as second type cardiac matched when there is a second type cardiac event within a specified time period of the neurological event;

computing with the processing circuitry a first rate of concordance between the neurological events and the first type cardiac events based on the number of first type cardiac matched events and the number of neurological events; and computing with the processing circuitry a second rate of concordance between the neurological events and the second type cardiac events based on the number of second type cardiac matched events and the number of neurological events.

10. The method of claim 9, wherein the first type cardiac event and the second type cardiac event are selected from the group consisting of bradycardia, asystole, tachyrhythmia, ST segment elevation.

11. The method of claim 9, further comprising enabling with the processing circuitry the use of detection of a first type cardiac event for detection of a neurological event based on the first rate of concordance.

\* \* \* \* \*